United States Patent
Miki et al.

(10) Patent No.: US 6,211,178 B1
(45) Date of Patent: Apr. 3, 2001

(54) TRIAZINE DERIVATIVE, PRODUCTION AND USE THEREOF

(75) Inventors: Hideki Miki; Koichi Iwanaga; Toshimi Matsuno, all of Osaka; Isao Aoki, Hyogo, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/335,918

(22) Filed: Jun. 18, 1999

Related U.S. Application Data

(62) Division of application No. 08/810,499, filed on Feb. 28, 1997, now Pat. No. 5,994,355, which is a continuation of application No. 08/755,059, filed on Nov. 22, 1996, now abandoned, which is a continuation-in-part of application No. 08/632,580, filed on Apr. 15, 1996, now abandoned, and a continuation-in-part of application No. 08/602,451, filed on Feb. 16, 1996, now abandoned, which is a continuation of application No. 08/322,489, filed on Oct. 14, 1994, now abandoned.

(30) Foreign Application Priority Data

Oct. 15, 1993 (JP) .................................................... 5-258654
Sep. 19, 1994 (JP) .................................................... 6-223761
Apr. 14, 1995 (JP) .................................................... 7-089786

(51) Int. Cl.$^7$ ........................ A61K 31/53; C07D 253/06; C07D 253/07
(52) U.S. Cl. .......................................... 514/242; 544/182
(58) Field of Search .............................. 544/182; 514/242

(56) References Cited

U.S. PATENT DOCUMENTS

| | | | |
|---|---|---|---|
| 3,773,938 | 11/1973 | Miller et al. ........................... | 544/182 |
| 4,631,278 | 12/1986 | Boeckx et al. ........................ | 514/242 |
| 4,782,056 | 11/1988 | Rosner et al. ........................ | 514/242 |
| 4,952,570 | 8/1990 | Boeckx et al. ........................ | 514/242 |
| 5,141,938 | 8/1992 | Lindner ................................ | 514/242 |
| 5,188,832 | 2/1993 | Mehlhorn et al. ................... | 424/405 |
| 5,256,631 | 10/1993 | Lindner ................................ | 504/229 |

FOREIGN PATENT DOCUMENTS

| | | |
|---|---|---|
| 25 32 363 | 2/1977 | (DE) . |
| 0 232 932 | 8/1987 | (EP) . |
| 0 383 285 | 8/1990 | (EP) . |
| 0 457 015 | 11/1991 | (EP) . |
| 0 476 439 | 3/1992 | (EP) . |
| 0 648 760 | 4/1995 | (EP) . |
| 1 562 363 | 3/1980 | (GB) . |
| WO86/00072 | 1/1986 | (WO) . |

OTHER PUBLICATIONS

Shinjikken Kagaku Koza, vol. 1, No. 14, p. 2555–2569, Jul. 20, 1978.

Hiyama, et al. "The Photoysis and Thermolysis of Ethyl Azidoformate in the Presence of Ketones", Bulletin of the Chemical Society of Japan, vol. 45:1863–1866 (1972).

Pugh et al. "Metabolism of 1–[(5–Nitrofurfurylidene-)amino]–2–imidazolidinone", Journal of Medicinal Chemistry, vol. 15, No. 3, pp. 270–273 (1972).

Daniel et al. "Cyclistation of Chlorosulfonyl Isocyanate with phenylhydrazones: A Synthetic Route to Triazinonoxathiazine–Dioxides and Triazinones"; Synthetic Communications, vol. 21, No. 15 & 16, 1991, pp. 1695–1703.

Abdel–Rahman et al. "Synthesis and biological activity of some new hetercylic systems derived from 2–carboxyhydrazide–5, 6–diphenyl–1,2,4–triazin–3–one", Indian Journal of Heterocyclic Chemistry, vol. 3, Oct.–Dec. 1993, pp. 121–126.

(List continued on next page.)

Primary Examiner—Richard L. Raymond
(74) Attorney, Agent, or Firm—Foley & Lardner

(57) ABSTRACT

The present invention provides a novel triazine derivative of the formula

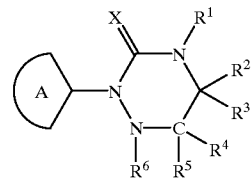

wherein ring A is an optionally substituted aromatic group which be;

X is an oxygen or sulfur atom;

$R^1$ and $R^6$ are each a hydrogen atom or an optionally substituted hydrocarbon residue or heterocyclic group which may bound through a hetero-atom;

$R^2$ and $R^3$ are each independently a hydrogen atom, a halogen atom, or a group bound through a carbon, oxygen or sulfur atom, or taken together, represent =S;

$R^4$ and $R^5$ are each independently a hydrogen atom, a halogen atom, or a group bound through a carbon, oxygen, nitrogen or sulfur atom;

$R^1$ and $R^2$, and $R^5$ and $R^6$, may each bind together to form a chemical bond; provided that where ring A is a phenyl group having at least a halogen atom in position-2 or 4 and X is an oxygen atom, $R^4$ and $R^5$ do not conjoinedly represent a chemical bond and an antiprotozoan composition containing the same or salt thereof.

21 Claims, No Drawings

OTHER PUBLICATIONS

Elghandour et al "Studies with polyfunctionally substituted heteroaromatics:synthesis of several new thiazoles, pyrazolo [5,1-c] triazines and of polyfunctionally substituted pyridines and pyrimidines"; *Tetrahedron*, vol. 48, No. 42, 1992, pp. 9295–9304.

Gnichtel et al. "Isomere Heterocyclen durch Cyclisierung von syn–und anti–alpha–Amiohydrazonen"; *Justus Liebeg Ann. Chem.*, vol. 12, 1978, pp 2033–2043.

Mustafa et al. "Das Verhalten von Oxazolionen–(5) und Thiazolinonen–(5) gegen N–Phenyl–hydroxylamin und Phenylhdrazin"; *Justus Liegib Ann. Chem.*, vol. 713, 1968, pp. 151–161.

Konz, et al. "2–Aryl–1,2,4–triazin–3 ones and 2–Aryl–1,2, 4–triazepin–3–ones", American Chemistry Society, pp. 122–129, (1987).

Miller et al. "Anticoccidal Derivative of 6–Azauracil. 2. Hiugh Potency ad Long Plasma Life of N1–Phenyl Structures", Journal of Medicinal Chemistry, vol. 22(12): 1483–1487, (1979).

McFarland et al, "Linear Discriminant and Multiple Regression Analyses of Anticoccidial Triazines" Journal of Medicinal Chemistry, vol. 34, pp. 1908–1911 (1991).

Palazzo et al., Chemical Abstracts, vol. 75, abstract 76749, 1971.*

* cited by examiner

TRIAZINE DERIVATIVE, PRODUCTION AND USE THEREOF

This application is a divisional of application Ser. No. 08/810,499, filed Feb. 28, 1997, now U.S. Pat. No. 5,994,355, which is a continuation of application Ser. No. 08/755,059, filed Nov. 22, 1996, now abandoned, which is a continuation-in-part of application Ser. No. 08/632,580, filed Apr. 15, 1996, now abandoned, and Ser. No. 08/602,451, filed Feb. 16, 1996, now abandoned, which in turn is a continuation of application Ser. No. 08/322,489, filed Oct. 14, 1994, now abandoned.

FIELD OF THE FIRST EMBODIMENT

The first embodiment relates to a novel triazine derivative or a salt thereof, an uses for them. More particularly, the first embodiment relates to the novel triazine derivatives or a salt thereof, which is useful for controlling parasitic protozoa, particularly for coccidia and the like, and an antiprotozoan composition comprising them.

BACKGROUND OF THE FIRST EMBODIMENT

Parasitic protozoa are parasites on a broad range of animals inclusive of mammals, birds, fishes and insects. The parasitic protozoa establish themselves in the internal organs or the external organs such as the skin and eye of the host animal. As such, these parasites give the hosts serious lesion and often infect the producing farmers of domestic animals, poultry and fish, causing great economic damage. Coccidiosis, which is one of the diseases causing the most serious economic damage to breeding, is mainly caused by several kinds of protozoa of the genus Eimeria, such as *E. tenella, E. necatrix, E. acervulira, E. maxima, E. brunetti* and *E. mivati*.

For example, *E. tenella* parasitizes the intestinal inner walls, such as that of the caecum, and often inflicts fatal damage on the host. Thus, the *E. tenella* infection produces several manifestations such as extensive erosion, inflammation and hemorrhage of the intestinal paries due to the development of the protozoa, caecal blood retention, and, hence, anaemia, retardation of growth or death of the host. Endoparastic protozoa are usually transmitted orally and as to coccidiosis in particular, even intensive disinfection with potassium dichromate solution fails to kill the oocysts. Moreover, since their life cycle is as short as about 7 days, one engaged in large-scale animal farming has to face the outbreak and spread of disease without an effective countermeasure.

As far as fishes are concerned, ectoparasitic protozoa are serious problems of concern. Their para-sitization damages the host's skin and gills, weakens the resistance of the host fish to infections and may occasionally be fatal. In large-scale fish farming, parasitic protozoa spread among the whole fish population on a farm and the resulting economic loss is too large to be overlooked.

A similar situation prevails for insects. Taking bees as an example, parasitic protozoan represented by *Nosema apis* are doing a great deal of harm to apiculture all over the world. *Nosema apis* destroys the internal organs to debilitate the host bee, and the host with accordingly decreased resistance tends to succumb to various other diseases.

Several drugs against parasitic protozoa have been proposed but most of them are limited in the indication and spectrum of activity and even protozoa with acquired resistance to certain drugs are already known. Furthermore, the weak activity of these drugs requires massive doses so that none are satisfactory enough from both economic and ecological points of view. Therefore, development of drugs which can be used broadly with sufficient effectiveness for control of such parasites in animals, poultry, fishes and insects are awaited in earnest.

As such drugs, 2-phenyl-6-azauracil derivatives were found to have an anticoccidial activity [J. Med. Chem. 22, 1483 (1979)] and a variety of 6-azauracil derivatives were synthesized and tested. However, these compounds were found to be teratogenic and, therefore, could not find application in the field. As compounds which overcame the problems related to the teratogenicity, 1,2,4-triazinediones are in use in some European countries, Australia and Hungary or South Africa as anticoccidial drugs. However, since these compounds remain in the body in long time their use is critically restricted and even banned in several countries including Japan.

In view of above state of the art, the present inventors have researched and found that a series of novel triazine derivatives have excellent activity against parasitic protozoa. Further intensive research led them to the discovery that this series of derivatives is suited for the control of a broad spectrum of parasitic protozoa encountered in rearing and raising animals such as mammals, birds, fish and insects under the usual husbandry and breeding conditions, are of low toxicity to animals, and exhibit remarkably high antiprotozoal activity even against strains resistant to the drugs heretofore available. This first embodiment has been brought into being on the basis of the above findings.

THE SUMMARY OF THE FIRST EMBODIMENT

The first embodiment is directed to:

(1) a triazine derivative of the formula

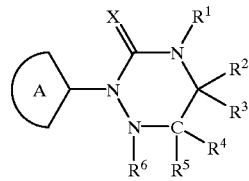

wherein ring A is an optionally substituted aromatic group;

X is an oxygen or sulfur atom;

$R^1$ and $R^6$ are each independently a hydrogen atom or an optionally substituted hydrocarbon residue or heterocyclic group which may bound through a hetero-atom;

$R^2$ and $R^3$ are each independently a hydrogen atom, a halogen atom, or a group bonding through a carbon, oxygen or sulfur atom, or, taken together, represent =S;

$R^4$ and $R^5$ are each independently a hydrogen atom, a halogen atom, or a group bound through a carbon, oxygen, nitrogen or sulfur atom;

$R^1$ and $R^2$, and $R^5$ and $R^6$ taken together may form a chemical bond; provided that where ring A is a phenyl group having at least a halogen atom in positions 2 or 4 and X is an oxygen atom, $R^5$ and $R^6$ do not bind together to form a chemical bond or salt thereof, (2) an antiprotozoan composition comprising an effective amount of the triazine derivative or salt mentioned above (1) and a physiologically acceptable carrier, excipient or diluent. (3) a feed additive which comprises the triazine derivatives or a salt thereof as mentioned above, and (4) a method of rearing and breeding animals which comprises administering an effective amount of the triazine derivatives or a salt mentioned above. The first embodiment also relates to (5) a method of preparing the triazine derivatives, or the antiprotozoal composition.

Referring to the above formula, the optionally substituted aromatic group, ring A, includes 5 to 6-membered homo- or hetero-aromatic groups which may have one or more substituents.

The carbocycle of said optionally substituted homoaromatic group may for example be benzene.

The heteroaromatic group includes 5- or 6-membered unsaturated heterocyclic groups containing 1 to 4 heteroatoms selected from among oxygen, sulfur, nitrogen and the like in addition to at least one carbon atom, for example 5-membered heterocyclic groups containing 1 to 4 heteroatoms selected from among oxygen, sulfur, nitrogen and the like in addition to at least one carbon atom, such as 2- or 3-thienyl, 2- or 3-furyl, 2- or 3-pyrrolyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, etc., and 6-membered heterocyclic groups containing 1 to 4 hetero-atoms selected from among oxygen, sulfur, nitrogen and the like in addition to at least one carbon atom, such as 2-, 3- or 4-pyridyl, N-oxide-2-, 3- or 4-pyridyl, 2-, 4- or 5-pyrimidinyl, N-oxide-2-, 4- or 5-pyrimidinyl, oxoimidazinyl, dioxotriazinyl, pyranyl, thiopyranyl, 1,4-oxazinyl, 1,4-thiazinyl, 1,3-thiazinyl, triazinyl, oxotriazinyl, 3- or 4-pyridazinyl, pyrazinyl, N-oxide-3- or 4-pyridazinyl, etc. Among them, 6-membered heterocyclic groups having one hetero-atom as a ring member are preferred and nitrogen-containing heterocyclic groups are particularly desirable.

Such a homo- or hetero-aromatic group may be substituted, in 1 to 5 or preferably 1 to 3 substitutable positions, by the following substituent groups, among others;

(1) $C_{1-4}$ alkyl, e.g. methyl, ethyl, propyl, isopropyl, butyl, isobutyl, sec-butyl, tert-butyl, etc.
(2) $C_{2-4}$ alkenyl, e.g. vinyl, 1-methylvinyl, 1-propenyl, allyl, etc.
(3) $C_{2-4}$ alkinyl, e.g. ethinyl, 1-propinyl, propargyl, etc.
(4) $C_{3-6}$ cycloalkyl, e.g. cyclopropyl, cyclobutyl, cyclopentyl, cyclohexyl, etc.
(5) $C_{5-7}$ cycloalkenyl, e.g. cyclopentenyl, cyclohexenyl, etc.
(6) $C_{7-11}$ aralkyl, e.g. benzyl, α-methylbenzyl, phenethyl, etc.
(7) phenyl
(8) $C_{1-6}$ alkoxy, e.g. methoxy, ethoxy, propoxy, isopropoxy, n-butoxy, iso-butoxy, sec-butoxy, tert-butoxy, etc.
(9) phenoxy
(10) $C_{1-6}$ alkanoyl, e.g. formyl, acetyl, propionyl, n-butyryl, iso-butyryl, etc.
(11) benzoyl
(12) $C_{1-6}$ alkanoyloxy, e.g. formyloxy, acetyloxy, propionyloxy, n-butyryloxy, iso-butyryloxy, etc. and benzoyloxy

(13) carboxyl
(14) $C_{2-7}$ alkoxycarbonyl, e.g. methoxycarbonyl, ethoxycarbonyl, n-propoxycarbonyl, iso-propoxycarbonyl, n-butoxycarbonyl, isobutoxycarbonyl, tert-butoxycarbonyl, etc.
(15) carbamoyl
(16) N-mono-$C_{1-4}$ alkylcarbamoyl, e.g. N-methylcarbamoyl, N-ethylcarbamoyl, N-propylcarbamoyl, N-isopropylcarbamoyl, N-butylcarbamoyl, etc.
(17) N-di-$C_{1-4}$ alkylcarbamoyl, e.g. N,N-dimethylcarbamoyl, N,N-diethylcarbamoyl, N,N-dipropylcarbamoyl, N,N-dibutylcarbamoyl, etc.
(18) cycloaminocarbonyl, e.g. 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, etc.
(19) halogens, e.g. F, Cl, Br, I,etc.
(20) mono-, di- or tri-halo-$C_{1-4}$ alkyl, e.g. chloromethyl, dichloromethyl, trifluoromethyl, trifluoroethyl, etc.
(21) oxo
(22) amidino
(23) imino
(24) optionally protected amino (the protected group for amino group is defined below)
(25) mono-$C_{1-4}$ alkylamino, e.g. methylamino, ethylamino, propylamino, isopropylamino, butylamino, etc.
(26) di-$C_{1-4}$ alkylamino, e.g. dimethylamino, diethylamino, dipropylamino, diisopropylamino, dibutylamino, etc.
(27) 3- to 6-membered cycloamino which may contain 1 to 3 hetero-atoms selected from among oxygen, sulfur, nitrogen, etc. in addition to at least one carbon atom and one nitrogen atom, such as aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl, etc.
(28) $C_{1-6}$ alkanamido such as formamido, acetamido, trifluoroacetamido, propionamido, butyrylamido, isobutyrylamido, etc.
(29) benzamido
(30) carbamoylamino
(31) N—$C_{1-4}$ alkylcarbamoylamino, e.g. N-methylcarbamoylamino, N-ethylcarbamoylamino, N-propylcarbamoylamino, N-isopropylcarbamoylamino, N-butylcarbamoylamino, etc.
(32) N-N-di-$C_{1-4}$ alkylcarbamoylamino, e.g. N,N-dimethylcarbamoylamino, N,N-diethylcarbamoylamino, N,N-dipropylcarbamoylamino, N,N-dibutylcarbamoylamino, etc.
(33) $C_{1-3}$ alkylenedioxy, e.g. methylenedioxy, ethylenedioxy, etc.
(34) —B(OH)$_2$
(35) hydroxy
(36) epoxy (—O—)
(37) nitro
(38) cyano
(39) mercapto

(40) sulfo
(41) sulfino
(42) phosphono
(43) dihydroxypolyol
(44) sulfamoyl
(45) $C_{1-6}$ monoalkylsulfamoyl, e.g. N-methylsulfamoyl, N-ethylsulfamoyl, N-propylsulfamoyl, N-isopropylsulfamoyl, N-butylsulfamoyl, etc.
(46) di-$C_{1-4}$ alkylsulfamoyl, e.g. N,N-dimethylsulfamoyl, N,N-diethylsulfamoyl, N,N-dipropylsulfamoyl, N,N-dibutylsulfamoyl, etc.
(47) $C_{1-6}$ alkylthio, e.g. methylthio, ethylthio, propylthio, isopropylthio, n-butylthio, sec-butylthio, tert-butylthio, etc.
(48) phenylthio
(49) $C_{1-6}$ alkylsulfinyl, e.g. methylsulfinyl, ethylsulfinyl, propylsulfinyl, butylsulfinyl, etc.
(50) phenylsulfinyl
(51) $C_{1-6}$ alkylsulfonyl, e.g. methylsulfonyl, ethylsulfonyl, propylsulfonyl, butylsulfonyl, etc.
(52) phenylsulfonyl and
(53) 5- or 6-membered heterocyclic groups containing 1 to 4 hetero-atoms selected from among oxygen, sulfur, nitrogen and the like in addition to at least one carbon atom, which may be bound through a one or two atom chain containing oxygen, sulfur, nitrogen, carbon or the like, for example 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxide-2-, 3- or 4-pyridyl, 2-, 4- or 5-pyrimidinyl, N-oxide-2-, 4- or 5-pyrimidinyl, oxoimidazinyl, dioxotriazinyl, pyranyl, thiopyranyl, 1,4-oxazinyl, 1,4-thiazinyl, 1,3-thiazinyl, triazinyl, oxotriazinyl, 3- or 4-pyridazinyl, pyrazinyl, N-oxide-3- or 4-pyridazinyl, and so on.

Of the above-mentioned groups, any group having a carbon chain of 2 or more C atoms or a cyclic group may be further substituted, in 1 or 2 substitutable positions, by such substituent groups as (a) halogens, e.g. Cl, F, etc.
(b) hydroxy,
(c) oxo,
(d) $C_{1-4}$ alkoxy, e.g. methoxy, ethoxy, etc.
(e) di-$C_{1-4}$ alkylamino, e.g. dimethylamino, diethylamino, etc.
(f) halo-$C_{1-4}$ alkyl, e.g. chloromethyl, trifluoromethyl, trifluoroethyl, etc.
(g) $C_{1-4}$ acyl, e.g. formyl, acetyl, etc.
(h) hydroxy-$C_{1-4}$ alkyl, e.g. hydroxymethyl, 2-hydroxyethyl, etc.
(i) $C_{1-4}$ alkoxy-$C_{1-4}$ alkyl, e.g. methoxymethyl, 2-ethoxyethyl etc.
(j) cyano
(k) thioxo and
(l) $C_{1-4}$ alkylthio, e.g. methylthio, ethylthio, propylthio, isopropylthio, n-butylthio, sec-butylthio, t-butylthio and so on.

Further, when the substitution exists on two ring-forming atoms adjacent to each other, they may bind together to form a ring. The condensed ring thus formed is a 8 to 10 membered bicyclic ring which includes bicyclic aryl group such as 1- or 2-pentalenyl, 1- or 2-indenyl (1H- or 2H-indenyl) or 1-or 2-naphthylyl, and bicyclic heterocyclic ring containing 1 to 4 hetero atom selected from among oxygen, sulfur, or nitrogen in addition to at least one carbon atom, such as indolyl, isoindolyl, benzofuryl, benzothiophenyl, benzothiazolyl, benzoxazolyl, tetrazolo[1,5-b]pyridazinyl, triazolo[4,5-b]pyridazinyl, benzimidazolyl, quinolyl, isoquinolyl, cinnolinyl, phthalazinyl, quinazolynyl, quinoxalinyl, indolidinyl, quinolidinyl, 1,8-naphthylidinyl, purinyl, putheridinyl, dibenzofuranyl, chromanyl, benzoxazinyl or like.

Among the above exemplified substituents, halogen atom, optionally substituted alkyl, especially $C_{1-4}$ alkyl group, haloalkyl group or optionally substituted aralkyl, especially phenyl $C_{1-4}$ alkyl group, a phenyl or heterocyclic group which may be bound through an atomic chain of 1 or 2 atoms such as phenoxy, phenylthio, benzoyl, benzoyloxy, phenylsulfonyl, benzomide and heterocyclic group optionally bound through an atomic chain of 1 or 2 atoms are preferable.

In regard to substitution topology, the benzene ring, for instance, may preferably be substituted in position 3 and/or 5, more preferably be substituted in position 4 in addition to the substitution in 3 and/or 5 but these are not exclusive choices, of course.

X represents an oxygen or sulfur atom and is preferably an oxygen atom.

Where $R^1$ and $R^6$ are the optionally substituted hydrocarbon residues each of which may be bound through a heteroatom, the particular hydrocarbon residue includes, among others, $C_{1-15}$ alkyl such as methyl, ethyl, propyl, isopropyl, butyl, isobutyl, s-butyl, t-butyl, pentyl hexyl, heptyl, octyl, nonyl, decyl, undecyl, dodecyl, tridecyl, tetradecyl, pentadecyl, etc., $C_{3-8}$ cycloalkyl such as cyclopropyl, cyclobutyl, cyclopentyl, cyclohexyl, etc., $C_{2-10}$ alkenyl such as vinyl, allyl, 2-methylallyl, 2-butenyl, 3-butenyl, 3-octenyl, etc., $C_{2-10}$ alkinyl such as ethinyl, 2-propinyl, 3-hexinyl, etc., $C_{3-10}$ cycloalkenyl such as cyclopropenyl, cyclopentenyl, cyclohexenyl, etc., $C_{6-14}$ aryl such as phenyl, naphthyl, etc., $C_{7-16}$ aralkyl such as benzyl, phenylethyl, etc. Among them alkyl, aryl and aralkyl group are preferable. Hydrocarbon residues having 1 to 7 carbon atoms are also preferable. Any of such hydrocarbon groups may have 1 to 5 substituent groups in substitutable positions as selected from among (1) nitro
(2) hydroxy
(3) oxo
(4) thioxo
(5) cyano
(6) carbamoyl
(7) carboxyl
(8) $C_{1-4}$ alkoxycarbonyl, e.g. methoxycarbonyl, ethoxycarbonyl, etc.
(9) sulfo
(10) halogens, e.g. F, Cl, Br, I, etc.
(11) $C_{1-4}$ lower alkoxy, e.g. methoxy, ethoxy, propoxy, isopropoxy, butoxy, isobutoxy, s-butoxy, t-butoxy, etc.
(12) phenoxy
(13) nalophenoxy, e.g. o-, m- or p-chlorophenoxy, o-, m- or p-bromophenoxy, etc.

(14) $C_{1-4}$ lower alkylthio, e.g. methylthio, ethylthio, n-propylthio, isopropylthio, n-butylthio, t-butylthio, etc.

(15) phenylthio

(16) $C_{1-4}$ lower alkylsulfinyl, e.g. methylsulfinyl, ethylsulfinyl, etc.

(17) $C_{1-4}$ lower alkylsulfonyl, e.g. methylsulfonyl, ethylsulfonyl, etc.

(18) amino

(19) $C_{1-6}$ lower acylamino, e.g. acetylamino, propionylamino, etc.

(20) mono- or di-$C_{1-4}$ alkylamino, e.g. methylamino, ethylamino, n-propylamino, isopropylamino, n-butylamino, dimethylamino, diethylamino, etc.

(21) $C_{1-4}$ lower acyl, e.g. formyl, acetyl, etc.

(22) benzoyl

(23) 5- or 6-membered heterocyclic groups containing 1 to 4 hetero-atoms selected from among oxygen, sulfur, nitrogen and the like in addition to at least one carbon atom, such as 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, isoquinolyl, indolyl, etc. which may be substituted by 1 to 4 substituents selected from among (a) halogens such as Br, Cl, F, etc., (b) $C_{1-4}$ lower alkyl such as methyl, ethyl, propyl, isopropyl, etc. and (c) halophenoxy such as o-, m- or p-chlorophenoxy, o-, m- or p-bromophenoxy, etc.

(24) $C_{1-10}$ haloalkyl, e.g. difluoromethyl, trifluoromethyl, trifluoroethyl, trichloroethyl, etc. Furthermore, where the hydrocarbon residue is cycloalkyl, cycloalkenyl, aryl or aralkyl, it may have 1 to 4 $C_{1-4}$ lower alkyl groups such as methyl, ethyl, propyl, isopropyl, butyl, etc as substituents.

Among the exemplified hydrocarbon residues, alky, aryl and aralkyl groups are preferable. The hydrocarbon residue having 1 to 8 is also preferable.

The acyl group of the hydrocarbon residue represented by $R^1$ or $R^6$ includes a group having a general formula of —$COR^2$, —$CONHR^2$, —$CSR^2$ or —$CSNHR^2$ wherein $R^2$ represents hydrogen or the above exemplified hydrocarbon group represented by $R^1$ or $R^6$. The hydrocarbon group of $R^2$ may have 1 to 2 substituents in substitutable position as selected from among the above exemplified group under (1) through (23). Among them, $C_{1-7}$ acyl group wherein $R^2$ is $C_{1-6}$ hydrocarbon group such as $C_{1-6}$ alkyl group (e.g. methyl, ethyl etc.), $C_{2-6}$ alkenyl group (e.g. vinyl), $C_{2-6}$ alkynyl group (e.g. ethynyl), $C_{3-6}$ cycloalkyl group (e.g. cyclohexyl), $C_{3-6}$ cycloalkenyl group (e.g. cyclohexenyl) or phenyl is preferable.

The oxycarbonyl group of the hydrocarbon residue represented by $R^1$ or $R^6$ includes a group having a general formula of —$COOR^2$ wherein $R^2$ is the same meaning definded above. The hydrocarbon group of $R^2$ may have 1 to 2 substituents in substitutable position as selected from among the above exemplified group under (1) through (23). Preferred, among the alkoxycarbonyl group, is the group wherein $R^2$ is $C_{1-6}$ hydrocarbon group such as $C_{1-6}$ alkyl group (e.g. methyl, ethyl etc.), $C_{2-6}$ alkenyl gorup (e.g. vinyl), $C_{2-6}$ alkynyl group (e.g. ethynyl), $C_{3-6}$ cycloalkyl group (e.g. cyclohexyl), $C_{3-6}$ cycloalkenyl group (e.g. cyclohexenyl) or phenyl.

The optionally substituted heterocyclic group which may be bound through a hetero-atom includes, among others, 5- to 8-membered heterocyclic groups or condensed heterocyclic groups derived therefrom containing 1 to 4 hetero-atoms selected from among oxygen, sulfur, nitrogen and the like in addition to at least one carbon atoms for example 5-membered hetero-cyclic groups containing 1 to 4 hetero-atoms selected from among oxygen, sulfur, nitrogen and the like in addition to at least one carbon atom, such as 2- or 3-thienyl, 2- or 3-furyl, 2- or 3-pyrrolyl, 2,3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, etc., 6-membered heterocyclic groups containing 1 to 4 hetero-atoms selected from among oxygen, sulfur, nitrogen and the like in addition to at least one carbon atom, such as N-oxide-2-, 3- or 4-pyridyl, 2-, 4- or 5-pyrimidinyl, N-oxide-2-, 4- or 5-pyrimidinyl, thiomorpholinyl, morpholinyl, oxoimidazinyl, dioxotriazinyl, pyrrolidinyl, piperidinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl, N-oxide-3- or 4-pyridazinyl, etc. and bicyclic or tricyclic condensed heterocyclic groups containing 1 to 4 hetero-atoms selected from among oxygen, sulfur, nitrogen and the like in addition to at least one carbon atom, such as benzofuryl, benzothiazolyl, benzoxazolyl, tetrazolo[1,5-b]pyridazinyl, triazolo[4,5-b]pyridazinyl, benzimidazolyl, quinolyl, isoquinolyl, cinnolinyl, phthalazinyl, quinazolynyl, quinoxalinyl, indolidinyl, quinolidinyl, 1,8-naphthylidinyl, purinyl, putheridinyl, dibenzofuranyl, carbazolyl, acrylidinyl, phenanthrydinyl, chromanyl, benzoxazinyl, phenazinyl, phenothiazinyl, phenoxazinyl, etc. Among them uncondensed heterocyclic rings, especially 5- or 6-membered rings, are preferable. Any of such heterocyclic groups may have 1 to 5 substituent groups selected from among (1) $C_{1-4}$ alkyl, e.g. methyl, ethyl, propyl, isopropyl, butyl, isobutyl, sec-butyl, ter-butyl, etc.

(2) $C_{2-4}$ alkenyl, e.g vinyl, 1-methylvinyl, 1-propenyl, allyl, etc.

(3) $C_{2-4}$ alkinyl, e.g. ethinyl, 1-propinyl, proparqyl, etc.

(4) $C_{3-6}$ cycloalkyl, e.g. cyclopropyl, cyclobutyl, cyclopentyl, cyclohexyl, etc.

(5) $C_{5-7}$ cycloalkenyl, e.g. cyclopentenyl, cyclohexenyl, etc.

(6) $C_{7-11}$ aralkyl, e.g. benzyl, α-methylbenzyl, phenethyl, etc.

(7) phenyl (8) $C_{1-6}$ alkoxy, e.g. methoxy, ethoxy, propoxy, isopropoxy, n-butoxy, iso-butoxy, sec-butoxy, tert-butoxy, etc.

(9) phenoxy

(10) $C_{1-6}$ alkanoyl, e.g. formyl, acetyl, propionyl, n-butyryl, iso-butyryl, etc.

(11) benzoyl

(12) $C_{1-6}$ alkanoyloxy, e.g. formyloxy, acetyloxy, propionyloxy, n-butyryloxy, iso-butyryloxy, etc., benzoyloxy

(13) carboxyl

(14) $C_{2-7}$ alkoxycarbonyl, e.g. methoxycarbonyl, ethoxycarbonyl, n-propoxycarbonyl, isopropoxycarbonyl, n-butoxycarbonyl, isobutoxycarbonyl, tert-butoxycarbonyl, etc.

(15) carbamoyl
(16) N-mono-$C_{1-4}$ alkylcarbamoyl, e.g. N-methylcarbamoyl, N-ethylcarbamoyl, N-propylcarbamoyl, N-isopropylcarbamoyl, N-butylcarbamoyl, etc.
(17) N,N-di-$C_{1-4}$ alkylcarbamoyl, e.g. N,N-dimethylcarbamoyl, N,N-diethylcarbamoyl, N,N-dipropylcarbamoyl, N,N-dibutylcarbamoyl, etc.
(18) cycloaminocarbonxl, e.g. 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, etc.
(19) halogens, e.g. F, Cl, Br, I, etc.
(20) mono-, di- or tri-halo-$C_{1-4}$ alkyl, e.g. chloromethyl, dichloromethyl, trifluoromethyl, trifluoroethyl, etc.
(21) oxo
(22) amidino
(23) imino
(24) amino
(25) mono-$C_{1-4}$ alkylamino, e.g. methylamino, ethylamino, propylamino, isopropylamino, butylamino, etc.
(26) di-$C_{1-4}$ alkylamino, e.g. dimethylamino, diethylamino, dipropylamino, diisopropylamino, dibutylamino, etc.
(27) 3- to 6-membered cycloamino containing 1 to 3 hetero-atoms selected from among oxygen, sulfur, nitrogen and the like in addition to at least one carbon atom and one nitrogen atom, such as aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl, N-ethylpiperazinyl, etc.
(28) $C_{1-6}$ alkanoylamido, e.g. formamido, acetamido, trifluoroacetamido, propionylamido, butyrylamido, iso-butyrylamido, etc.
(29) benzamido
(30) carbamoylamino
(31) N—$C_{1-4}$ alkylcarbamoylamino, e.g. N-methylcarbamoylamino, N-ethylcarbamoylamino, N-propylcarbamoylamino, N-isopropylcarbamoylamino, N-butylcarbamoylamino, etc.
(32) N,N-di-$C_{1-4}$ alkylcarbamoylamino, e.g. N,N-dimethylcarbamoylamino, N,N-diethylcarbamoylamino, N,N-dipropylcarbamoylamino, N,N-dibutylcarbamoylamino, etc.
(33) $C_{1-3}$ alkylenedioxy, e.g. methylenedioxy, ethylenedioxy, etc.
(34) —B(OH)$_2$
(35) hydroxy
(36) epoxy (—O—)
(37) nitro
(38) cyano
(39) mercapto
(40) sulfo
(41) sulfino
(42) phosphono
(43) dihydroxypolyol
(44) sulfamoyl
(45) $C_{1-6}$ monoalkylsulfamoyl, e.g. N-methylsulfamoyl, N-ethylsulfamoyl, N-propylsulfamoyl, N-isopropylsulfamoyl, N-butylsulfamoyl, etc.
(46) di-$C_{1-4}$ alkylsulfamoyl, e.g. N,N-dimethylsulfamoyl, N,N-diethylsulfamoyl, N,N-dipropylsulfamoyl, N,N-dibutylsulfamoyl, etc.
(47) $C_{1-6}$ alkylthio, e.g. methylthio, ethylthio, propylthio, isopropylthio, n-butylthio, sec-butylthio, tert-butylthio, etc.
(48) phenylthio
(49) $C_{1-6}$ alkylsulfinyl, e.g. methylsulfinyl, ethylsulfinyl, propylsulfinyl, butylsulfinyl, etc.
(50) phenylsulfinyl
(51) $C_{1-6}$ alkylsulfonyl, e.g. methylsulfonyl, ethylsulfonyl, propylsulfonyl, butylsulfonyl, etc. and
(52) phenylsulfonyl.

The above optionally substituted hydrocarbon residue or heterocyclic group which may be bound through a hetero-atom is, for example, the nitrogen atom of amino, substituted amino (e.g. amino $C_{1-4}$ alkylamino, hydroxyamino, etc.), or hydrazino, the sulfur atom of thiocarbonyl or sulfino, or an oxygen atom.

Preferred, among the above-mentioned optionally substituted hydrocarbon residues and heterocyclic groups which may be bound through a hetero-atom, are optionally substituted alkyl, aryl, aralkyl and optionally substituted nitrogen-containing heterocyclic groups which may be bound through a hetero-atom and more preferred are optionally substituted $C_{1-4}$ alky group. $C_{1-7}$ acyl group and $C_{1-7}$ oxycarbonyl group are also preferable.

The group bound through a carbon, oxygen or sulfur atom, represented by $R^2$ and $R^3$, includes, among others,
(1) cyano
(2) carboxy
(3) carbamoyl
(4) mercapto
(5) hydroxy
(6) $C_{1-4}$ alkyl, e.g. methyl, ethyl, propyl, iso-propyl, etc.
(7) $C_{1-6}$ alkylthio, e.g. methylthio, etc.
(8) $C_{7-11}$ alalkylthio, e.g. benzylthio, etc.
(9) $C_{2-4}$ alkenyl, e.g vinyl, 1-methylvinyl, 1-propenyl, allyl, allenyl, etc.
(10) $C_{2-4}$ alkinyl, e.g. ethinyl, 1-propinyl, propargyl, etc.
(11) $C_{1-6}$ alkoxy e.g. methoxy, etc.
(12) $C_{3-6}$ cycloalkyl, e.g. cyclopropyl, cyclopentyl, cyclohexyl, etc.
(13) $C_{6-10}$ aryl, e.g. phenyl, naphthyl, etc, or
(14) 5- to 7-membered heterocyclic groups containing 1 to 4 hetero-atoms selected from among nitrogen, sulfur, oxygen and the like in addition to at least one carbon atom, such as pyrrolyl, imidazolyl, pyrazolyl, thienyl, furyl, thiazolyl, thiadiazolyl, oxazolyl, oxadiazolyl, pyridyl, pyranyl, pyrazinyl, pyrimidinyl, pyridazinyl, dioxolanyl, piperidino, morpholino, N-methylpiperazinyl, N-ethylpiperazinyl, dioxanyl, etc. Among the above-mentioned groups, the groups mentioned under (6) through (14) may have 1 or 2 substituent groups in substitutable positions as selected from among
(a) halogens, e.g. Cl, F, etc.
(b) hydroxy
(c) oxo
(d) $C_{1-4}$ alkoxy, e.g. methoxy, ethoxy, etc.
(e) di-$C_{1-4}$ alkylamino, e.g. dimethylamino, diethylamino, etc.
(f) halo-$C_{1-4}$ alkyl, e.g. chloromethyl, trifluoromethyl, trifluoroethyl, etc.

(g) $C_{1-4}$ acyl, e.g. formyl, acetyl, etc.
(h) hydroxy-$C_{1-4}$ alkyl, e.g. hydroxymethyl, 2-hydroxyethyl, etc.,
(i) $C_{1-4}$ alkoxy-$C_{1-4}$ alkyl, e.g. methoxymethyl, 2-ethoxyethyl, etc.
(j) thioxo,
(k) sulfide,
(l) $C_{3-6}$ cyloalkyl, e.g. cyclopropyl, etc., and
(m) mercaplo The halogen atom may for example be chlorine, bromine, fluorine or iodine.

Preferred, among the above, are halogen atoms and optionally substituted alkyl or aryl groups which may be bound through an oxygen or sulfur atom. Among alkyl groups a low alkyl group of 1 to 4 carbon atoms is preferable and phenyl is a preferable aryl group.

The group bound through a carbon, nitrogen, oxygen or sulfur atom, $R^4$ and $R^5$, includes
(1) cyano
(2) carboxy
(3) carbamoyl
(4) amino
(5) nitro
(6) hydroxy
(7) mercapto
(8) $C_{1-4}$ alkyl, e.g. methyl, ethyl, propyl, iso-propyl, etc.
(9) $C_{2-4}$ alkenyl, e.g. vinyl, 1-methylvinyl, 1-propenyl, allyl, allenyl, etc.
(10) $C_{2-4}$ alkinyl, e.g. ethinyl, 1-propinyl, propargyl, etc.
(11) $C_{3-6}$ cycloalkyl, e.g. cyclopropyl, cyclopentyl, cyclohexyl, etc.
(12) $C_{6-10}$ aryl, e.g. phenyl, naphthyl, etc. or
(13) 5- to 7-membered heterocyclic groups containing 1 to 4 hetero-atoms selected from among nitrogen, sulfur, oxygen and the like in addition to at least one carbon atom, such as pyrrolyl, imidazolyl, pyrazolyl, thienyl, furyl, thiazolyl, thiadiazolyl, oxazolyl, oxadiazolyl, pyridyl, pyranyl, pyrazinyl, pyrimidinyl, pyridazinyl, dioxolanyl, piperidino, morpholino, N-methylpiperazinyl, N-ethylpiperazinyl, dioxanyl, etc. Among these groups, the groups mentioned under (8) through (13) may have 1 or 2 substituent groups in substitutable positions as selected from among
(a) halogens, e.g. Cl, F, etc.
(b) hydroxy
(c) oxo
(d) $C_{1-4}$ alkoxy, e.g. methoxy, ethoxy, etc
(e) di-$C_{1-4}$ alkylamino, e.g. dimethylamino, diethylamino, etc.
(f) halo-$C_{1-4}$ alkyl, e.g. chloromethyl, trifluoromethyl, trifluoroethyl, etc.
(g) $C_{1-4}$ acyl, e.g. formyl, acetyl, etc.
(h) hydroxy-$C_{1-4}$ alkyl, e.g. hydroxymethyl, 2-hydroxyethyl, etc., and
(i) $C_{1-4}$ alkoxy-$C_{1-4}$ alkyl, e.g. methoxymethyl, 2-ethoxyethyl, etc.

The halogen may for example be chlorine, bromine, fluorine or iodine.

Preferred, among the above, are halogens and alkyl or aryl groups optionally substituted and/or each bonding through a nitrogen, oxygen or sulfur atom.

$R^1$ and $R^2$, or $R^5$ and $R^6$, may each bind together to form a chemical bond, that is to say a double bond between the carbon atom at 5-position and nitrogen atom at 4-position or between the carbon atom at 6-position and nitrogen atom at 1-position of the triazine ring. The double bond between 4- and 5-positions and that between 1- and 6-positions may exist concurrently but it is preferable that only one of them exists and is more preferable that a double bond be present between the 1- and 6-positions.

Where the triazine ring is tautomeric, the respective tautomers are also subsumed in the concept of triazine derivative of this invention.

Among the triazine derivatives of the present invention the compound of the following formula or salt thereof are preferable:

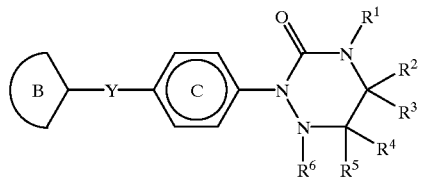

wherein $R^1$, $R^2$, $R^3$, $R^4$, $R^5$ and $R^6$ are the same meanings defined above, ring B is an optionally substituted 5- or 6-membered cyclic group which may contains hetero atoms, ring C is an optionally substituted phenylen group, Y is a chemical bond, —O—, —S(O)$_m$— or an optionally protected amino or an optionally substituted lower hydrocarbon and m is 0, 1 or 2.

Optionally substituted 5- or 6-membered cyclic group represented by ring B includes carbon rings such as cycloalkyl, such as cyclopentyl or cyclohexyl, etc., cycloalkenyl, such as 1-, 2- or 3- cyclopentenyl, 1-, 2- or 3-cyclohexenyl, etc., phenyl or heteroaromatic groups containing 1 to 4 hetero-atoms selected from among oxygen, sulfur, nitrogen and the like in addition to at least one carbon atom, for example 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, etc., N-oxide-2-, 3- or 4-pyridyl, 2-, 4- or 5-pyrimidinyl, N-oxide-2-, 4- or 5-pyrimidinyl, oxoimidazinyl, dioxotriazinyl, pyranyl, thiopyranyl, 1,4-oxazinyl, 1,4-thiazinyl, 1,3-thiazinyl, triazinyl, oxotriazinyl, 3- or 4-pyridazinyl, pyrazinyl, N-oxide-3- or 4-pyridazinyl, etc. Among them, 6-membered cyclic groups, especially phenyl is preferable and 6-membered nitrogen-containing heterocyclic groups are particularly desirable when ring B is a heterocyclic group.

Such a cyclic group may be substituted, in 1 to 5 or preferably 1 to 3 substitutable positions, by the following substituent groups, among others:
(1) $C_{1-4}$ alkyl, e.g. methyl, ethyl, propyl, isopropyl, butyl, isobutyl, sec-butyl, tert-butyl, etc.
(2) $C_{1-4}$ lower alkoxy, e.g. methoxy, ethoxy, propoxy, isopropoxy, butoxy, isobutoxy, s-butoxy, t-butoxy, etc.
(3) carboxy
(4) carbamoyl
(5) halogens, e.g. F, Cl, Br, I, etc.
(6) mono-, di- or tri halo-$C_{1-4}$ alkyl e.g. chloromethyl, dichloromethyl, trifluoromethyl, trifluoroethyl, etc.
(7) amino (8) —B(OH)$_2$
(9) hydroxy
(10) nitro
(11) cyano
(12) mercapto
(13) sulfo
(14) sulfino
(15) phospho and
(16) C$_{1-4}$ acyl e.g. folmyl acetyl etc.

Halogen atom or alkyl or haloalkyl group is preferable.

When the substitutions exist on two ring-forming atoms adjacent to each other, they may bind together to form a ring which is condensed with the ring B.

The optionally substituted phenylene group represented by the ring C may be substituted by 1 to 4 preferably 1 to 2, substituents selected from those of the ring A. Among them, a halogen atom, alkyl, alkoxy or haloalkyl group is desirable.

The lower hydrocarbon residue represented by Y includes a hydrocarbon group of 1 to 6 carbon atoms, for example C$_{1-4}$ alkylene such as methylene, ethylene, propylene, trimethylene, tetramethylene etc, C$_{2-6}$ alkenylene such as vinylene, propenylene, 1- or 2-butenylene, butadienylene etc. or C$_{2-6}$ alkylydene such as ethylydene, propilydene buthylydene etc. These lower hydrocarbon groups are substituted with 1 to 4 substituents selected from (1) halogens, e.g. Cl, F, etc.
(2) hydroxy,
(3) oxo,
(4) cyano,
(5) C$_{1-4}$ alkoxy, e.g. methoxy, ethoxy, etc.
(6) mono- or di-C$_{1-4}$ alkylamino, e.g. methylamino, ethyklamino, propylamino, dimethylamino, diethylamino, dipropylamino, etc.
(7) halo-C$_{1-4}$ alkyl, e.g. fluoromethyl, fluoethyl, chloromethyl, chloroethyl, bromomethyl, bromoethyl, trifluoromethyl, trifluoroethyl, chloropropyl, etc.
(8) C$_{1-4}$ acyl, e.g. formyl, acetyl, propyonyl, etc.
(9) hydroxy-C$_{1-4}$ alkyl, e.g. hydroxymethyl, hydroxyethyl, 2-hydroxyethyl, hydroxypropyl, etc.
(10) C$_{1-4}$ alkoxy-C$_{1-4}$ alkyl, e.g. methoxymethyl, 2-ethoxyethyl, etc.
(11) C$_{1-4}$ alkoxy-carbonyl, e.g. methoxycarbonyl, ethoxycarbonyl, n-propoxycarbonyl, n-butoxycarbonyl, tert-butoxycarbonyl etc.
(12) thioxo and
(13) C$_{1-4}$ alkylthio, e.g. methylthio, ethylthio, propylthio, isopropylthio, buthylthio, isobuthylthio, sec-buthylthio, tert-buthylthio etc. and so on.

Among them, a hydrocarbon group having 1 to 2 carbon atom in a straight chain which links the rings B and C such as optionally substituted methylene, ethylene, vinylene and ethynylene is preferable. Further, a C$_{1-3}$ alkylene, C$_{2-4}$ alkylene or C$_{2-4}$ alkenylidene group which may optionally be substituted with 1 to 2 of the above mentioned substituents is most preferable.

For example, such a preferable embodiment includes methylene group optionally substituted with chloro, fluoro, methyl, monofluoromethyl, monochloromethyl, trifluoromethyl, hydroxy, carboxy, oxo (to a carbonyl group), thioxo (to a thiocarbonyl group), methoxycarbonyl, ethoxycarbonyl, cyano or the like, ethylene group optionally substituted, at position 1 or 2 independently, with chloro, fluoro, methyl, monofluoromethyl, monochloromethyl, trifluoromethyl, hydroxy, carboxy, cyano or like, propylen group optionally substituted, at position 1, 2, or 3 independently, with chloro, fluoro, methyl, monofluoromethyl, monochloromethyl, trifluoromethyl, hydroxy carboxy, oxo (to form e.g. ethylidenecarbonyl, acetylethylene etc.), methoxy, ethoxy, methylthio, ethylthio, dimethylamino, diethylamino or the like, C$_{2-4}$ alkenylen group optionally substituted with chloro, fluoro methyl, monofluoromethyl, monochloromethyl, hydroxy, carboxy, cyano or the like independently on any substituted position, and C$_{2-4}$ alkylidene group optionally substituted with chloro, fluoro, oxo (to form e.g. formylmethylene, acetylmethylene, methylcarbonylmethylene etc, hydroxy, methoxy, ethoxy, methylthio, dimethylamino, diethylamino or the like.

In the optionally protected the amino of Y, amino group may be protected with a group selected from (1) formyl
(2) C$_{1-6}$ alkyl-carbonyl, e.g. acetyl, ethylcarbonyl, propylcarbonyl, butylcarbonyl which may substituted with halogen atoms, e.g. Cl, Br, F etc.
(3) C$_{6-10}$ aryl-carbonyl, e.g. phenylcarbonyl which may substituted with 1 to 3 halogen atom, e.g. Cl, Br, F etc, C$_{1-6}$ alkylcarbonyl, e.g. methylcarbonyl, ethylcarbonyl, propylcarbonyl, butylcarbonyl etc. or nitro group
(4) C$_{1-6}$ alkyloxycarbonyl, e.g. methoxycarbonyl, ethoxycarbonyl which may substituted with 1 to 3 halogen atom, e.g. Cl, Br, F etc, C$_{1-6}$ alkylcarbonyl, e.g. methylcarbonyl, ethylcarbonyl, propylcarbonyl, butylcarbonyl etc. or nitro group
(5) C$_{6-10}$ aryloxycarbony, e.g. phenoxycarbony which may substituted with 1 to 3 halogen atom, e.g. Cl, Br, F etc, C$_{1-6}$ alkylcarbonyl, e.g. methylcarbonyl, ethylcarbonyl, propylcarbonyl, butylcarbonyl etc. or nitro group
(6) C$_{7-12}$ aralkyl-carbonyl, e.g. benzylcarbonyl, phenylethylcarbonyl which may substituted with 1 to 3 halogen atoms e.g. Cl, Br, F etc, C$_{1-6}$ alkylcarbonyl, e.g. methylcarbonyl, ethylcarbonyl, propylcarbonyl, butylcarbonyl etc. or nitro group
(7) trityl which may substituted with 1 to 3 halogen atom, e.g. Cl, Br, F etc, C$_{1-6}$ alkylcarbonyl, e.g. methylcarbonyl, ethylcarbonyl, propylcarbonyl, butylcarbonyl etc. or nitro group and
(8) phthaloyl which may substituted with 1 to 3 halogen atom, e.g. Cl, Br, F etc, C$_{1-6}$ alkylcarbonyl, e.g. methylcarbonyl, ethylcarbonyl, propylcarbonyl, butylcarbonyl etc. or nitro group or the like. However, any group may be used as long as it can be re-converted to amino chemically in the synthesis rout using a general technique of organic chemistry or under physiological conditions (for example by enzymatic lysis or metabolism).

Among the divalent groups represented by Y, —O—, —S— or optionally substituted C$_{1-6}$ bivalent hydrocarbon group, especially optionally substituted C$_{1-4}$ alkylen or C$_{2-4}$ alkylydene group is preferable.

In the above formula, prefered embodiments of R$^1$ and R$^6$ are each hydrogen atom or an optionally substituted hydrocarbon residue; especially alkyl, aryl or aralkyl group, which may be bound through a hetero atom.

Further, hydrogen, C$_{1-7}$ acyl group (e.g. acetyl, benzyl etc.), C$_{1-7}$ oxycarbonyl group (e.g. methoxycarbonyl, hydroxy carbonyl etc.) or an optionally substituted alkyl such as C$_{1-4}$ alkyl, mono-, di- or trihalo-C$_{1-4}$ alkyl, C$_{1-4}$ alkylcarbonyl or the like is more preferred as R$^1$.

In the above formula, $R^2$ and $R^3$ are preferably selected each from among hydrogen atom, halogen atom and an optionally substituted alkyl such as $C_{1-4}$ alkyl, $C_{1-4}$ alkoxy, $C_{1-4}$ alkylthio, mono-, di- or trihalo-$C_{1-4}$ or like, aryl such as phenyl, phenoxy, phenylthio, mono-, di- or tri-halophenyl or aralkyl group such as benzyl, benzylthio or the like, or may be taken together to form ═S, more preferably selected each from among hydrogen atom, halogen atom and an optionally substituted alkyl group. Further, at least either, especially both of $R^2$ and $R^3$ may preferably be a hydrogen atom.

In the above formula, $R^4$ and $R^5$ are preferably selected each from among, hydrogen atom, halogen atom and an optionally substituted alkyl or aryl group, more preferably selected from hydrogen or an optionally substituted $C_{1-4}$ alkyl group. Further, at least either, especially both, of $R^4$ and $R^5$ may preferably be a hydrogen atom.

$R^6$ are preferred to be hydrogen or an optionally substituted $C_{1-4}$ alkyl group such as $C_{1-4}$ alkyl, mono-, di- or trihalo-$C_{1-4}$ alkyl, $C_{1-4}$ acyl, $C_{1-4}$ alkylcarbony or the like.

The compounds in which $R^1$ and $R^2$ and/or $R^5$ and $R^6$ bind together to form a chemical bond are also desired.

The salt of a triazine derivative according to this invention is preferably a salt physiologically acceptable for animals and as such includes salts with alkali metals such as sodium, potassium, etc., salts with alkaline earth metals such as calcium etc., salts with inorganic acids such as hydrochloric acid, nitric acid, sulfuric acid, phosphoric acid, etc., and salts with organic acids such as acetic acid, succinic acid and so on.

The triazine derivative of this first embodiment can be produced by, inter alia, the following reaction routes.

Reaction a)

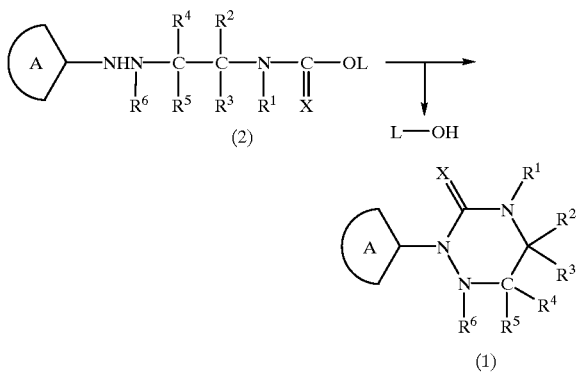

wherein ring A, X, $R^1$, $R^2$, $R^3$, $R^4$, $R^5$ and $R^6$ have the meanings defined hereinbefore; L represents hydrogen or an alkyl or aryl group.

The above reaction a) is directed to cyclization of hydrazine derivative (2) to a compound of general formula (1).

This reaction is generally conducted in an inert solvent or in the absence of a solvent, optionally in the presence of a Lewis acid or a Lewis base. The reaction temperature is generally about 60 to about 200° C. and preferably about 100 to about 160° C. For this reaction, virtually any inert organic solvent can be employed. Thus, it may can be any of the reaction solvents which are generally used in organic chemistry, for example, benzene, ligroin, benzine, toluene, xylene, methylene chloride, ethylene chloride, chloroform, carbon tetrachloride, dichloroethane, chlorobenzene, o-dichlorobenzene, ethers (e.g. dibutyl ether, glycol dimethyl ether, diglycol dimethyl ether, tetrahydrofuran, dioxane, etc.), ketones (e.g. methyl ethyl ketone, methyl isopropyl ketone, methyl isobutyl ketone, etc.), esters (e.g. ethyl acetate etc.), nitriles (e.g. acetonitrile, propionitrile, etc.), amides (e.g. dimethylformamide, dimethylacetamide, hexamethylphosphorotriamide, etc.), N-methylpyrrolidone, dimethylsulfoxide, tetramethylenesulfone, mercaptoacetic acid, pyridine, and so on. This reaction may be carried out while the byproduct such as alcohol or water is removed.

Reaction b)

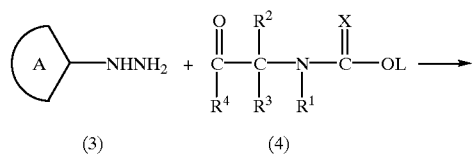

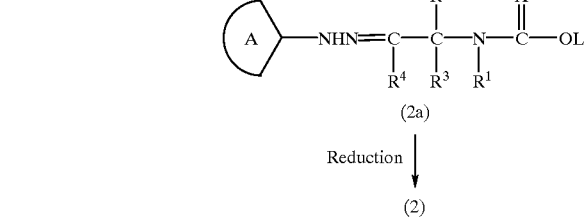

wherein ring A, $R^1$–$R^4$, L and X have the meanings defined hereinbefore.

The above reaction b) comprises reacting hydrazine (3) with a carbomic acid derivative (4) to give a hydrozone derivative (2a) followed by reduction to provide a hydrazine derivative (2).

The compound (2a) obtained by reacting compound (3) with compound (4) in an inert organic solvent is then reduced in the conventional manner. The inert organic solvent that can be used includes, among others, hydrocarbons (e.g. nonane, decane, dodecane, xylene, toluene, benzene, etc.), halogenated hydrocarbons (e.g. chloroform, dichloromethane, carbone tetrachloride, chlorobenzene, dichloroethane, etc.), alcohols (e.g. diethylene glycol etc.), ethers (e.g. diethylene glycol monobutyl ether, diethylene glycol dibutyl ether, etc.), dioxane, tetrahydrofuran, dimethylformamide, sulfoxides and sulfones such as di-methyl sulfoxide, tetramethylenesulfone and so on. This reaction can also be conducted in the presence of a Lewis acid or a dehydrating agent (e.g. dicyclohexylcarbodiimide, carbonyidiimidazole, etc.).

This reaction can be carried out generally at a temperature within the range of about −10° C. to about 150° C. In particular, the temperature range of about 10 to about 20° C. is preferred when a dehydrating agent is used and the range of about 60 to about 110° C. is preferred in other instances.

Reduction of compound (2a) can be achieved by treating (2a) in the presence of about 1 to about 10 equivalents of a catalyst (palladium, $NaBH_4$, $LiAlH_4$, etc.) in alcohol or water at about 25 to about 60° C. for about 0.5 to about 10 hours.

The compound (4) can be synthesized by the method of Tamejiro Hiyama et al. [Bull. Chem, Soc. Japan., 45, 1863–1866 (1972)].

Reaction c)

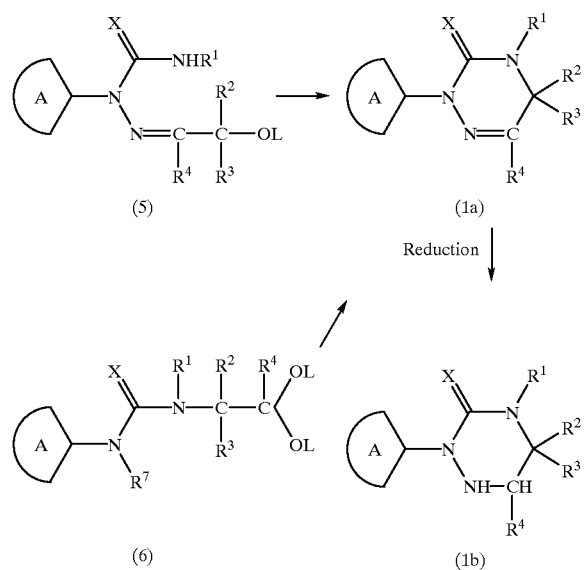

wherein ring A, $R^1$, $R^2$, $R^3$, $R^4$, L and X have the same meanings defined hereinbefore; $R^7$ represents an optionally protected amino.

The above reaction c) is directed to cyclization of semicarbazone derivative (5) to synthesize a compound of the first embodiment. The cyclization reaction is carried out in an inert solvent or in the absence of a solvent, optionally in the presence of a Lewis acid or a Lewis base. The reaction is generally conducted at a temperature within the range from about 0° C. to about 200° C. In particular, the reaction temperature of about 5 to about 30° C. is preferred when a hydroxyl-activating agent (e.g. trifluoroacetic anhydride, acetic anhydride, phosphorus oxychloride, etc.) is employed. Where no hydroxyl-activating agent is employed, the reaction is carried out at about 100 to about 200° C., preferably at about 140 to about 180° C. As the reaction solvent, virtually any inert organic solvent can be employed. Thus, such solvent includes aliphatic and aromatic hydrocarbons (e.g. benzene, ligroin, benzine, toluene, xylene, etc.), halogenated hydrocarbons (e.g. methylene chloride, ethylene chloride, chloroform, carbon tetrachloride, dichloroethane, chlorobenzene, o-dichlorobenzene, etc.), ethers (e.g. dibutyl ether, glycol dimethyl ether, diglycol dimethyl ether, tetrahydrofuran, dioxane, etc.), ketones (e.g. methyl ethyl ketone, methyl isopropyl ketone, methyl isobutyl ketone, etc.), esters (e.g. ethyl acetate etc.), nitriles (e.g. acetonitrile, propionitrile, etc.), amides (e.g. dimethylformamide, dimethylacetamide, hexamethylphosphoric triamide, etc.), N-methyl-pyrrolidone, dimethyl sulfoxide, tetramethylenesulfone, mercaptoacetic acid, pyridine, etc. To remove the residual hydroxyl-activating agent after the reaction, an organic base such as pyridine, triethylamine, dimethylpyridine, etc. or an inorganic base such as potassium hydroxide, sodium hydroxide, etc. can be employed.

This reaction may be conducted in the presence of a dehydrating agent, such as dicyclohexylcarbodiimide, carbonyldiimidazole and so on.

The tetrahydrotriazine compound (1a) thus obtained can be reduced in the manner described for reaction b) to give the hexahydrotriazine compound (1b).

Furthermore, when the 3,3-disubstituted semicarbazide derivative (6) is used as an intermediate, it can be heat-cyclized in the same manner as the compound (5) to synthesize the-tetrahydrotriazine compound (1a). The cyclization reaction is carried out generally at a temperature of about 60 to about 160° C., preferably about 80 to about 120° C. This reaction can also be conducted with the aid of a catalyst, that is to say in the presence of a Lewis acid or the like (e.g. trifluoroborane etherate, methanesulfonic acid, sulfuric acid, hydrochloric acid, phosphoric acid, polyphosphoric acid, etc.). In this reaction, the protection group for the optionally protected amino represented by $R^7$ is any group generally used in organic chemistry [c.f. Shinjikken Kagaku koza Vol. 14, p.2555 Edit. Nihon seikagakkai].

The compound (6), wherein $R^7$ is amino, can be obtained by a process which comprises dissolving an N-alkyl-N-(2,2-dialkoxyethyl)-N'-phenylurea in an aprotic solvent (e.g. dimethylformamide, dimethyl sulfoxide, N-methylpyrrolidone, etc.), adding a finely divided (ca. 50–100 μm) powder of potassium hydroxide or sodium hydroxide, then adding an aminating agent (e.g. hydroxyamino-O-sulfonic acid, 3-chloro-2-cyanopherethoxy amine, etc.) in a few portions under vigorous stirring at about 0 to about 10° C., further stirring the reaction mixture at about 25 to about 30° C. for another 2 hours, pouring it in iced water, neutralizing the mixture with diluted hydrochloric acid, and extracting it with chloroform.

The N-alkyl-N-(2,2-dialkoxyethyl)-N'-phenylurea can be synthesized by the conventional reaction between phenyl isocyanate and N-2,2-dialkoxyethylamine.

The compound (6) in which $R^7$ is a protected amino can be obtained by following reaction (c).

Reaction d)

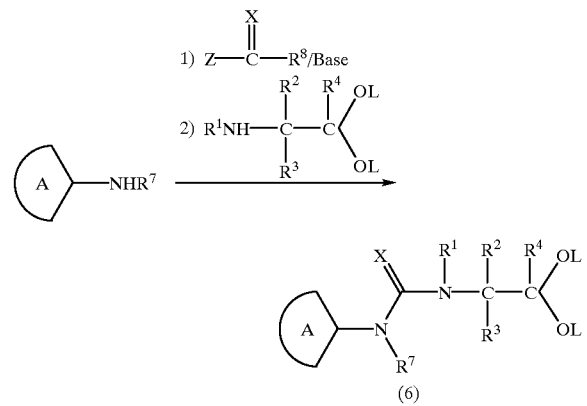

wherein A, $R^1$, $R^2$, $R^3$, $R^4$, $R^7$, L and X have the same meanings defined hereinbefore; $R^8$ is halogen atom or an optionally substituted $C_{1-4}$ alkoxy (e.g. halo $C_{1-4}$ alkyl etc.) or phenoxy and Z is halogen atom.

The above reaction (d) is directed to an amination followed by an acylation of a hydrazine derivative in the presence of base to provide compound (6). The reaction is generally conducted at a temperature with in the range of about –5 to about 40° C., preferably about 5 to about 10° C. The base used therein includes an organic base such as pyridine, triethylamine, DBU, collidine, 1,1,3,3-tetramethylguanizine and so on.

As the reaction solvent, virtually any inert organic solvent can be employed. Thus, such solvent includes aliphatic and aromatic hydrocarbons (e.g. benzene, ligroin, benzine, toluene, xylene, etc.), halogenated hydrocarbons (e.g. methylene chloride, ethylene chloride, chloroform, carbon tetrachloride, dichloroethane, chlorobenzene, o-dichlorobenzene, etc.), ethers (e.g. dibutyl ether, glycol dimethyl ether, diglycol dimethyl ether, tetrahydrofuran, dioxane, etc.), ketones (e.g. methyl ethyl ketone, methyl isopropyl ketone, methyl isobutyl ketone, etc.), esters (e.g. ethyl acetate etc.), nitriles (e.g. acetonitrile, propionitrile, etc.), amides (e.g. dimethylformamide, dimethylacetamide, hexamethylphosphoric triamide, etc.), N-methyl-pyrrolidone, dimethyl sulfoxide, tetramethylenesulfone, mercaptoacetic acid, pyridine, etc.

Of the compounds of this invention, species in which position-5 represents =S can be obtained by a process which comprises heating a 1,2,4-triazine-1,3-dione compound (which can be synthesized in accordance with the manner reported by Max W. Miller et al., J. Med. Chem., 22, 1483, 1979) with Lawesson's reagent or phosphorus pentasulfide in a solvent such as aliphatic or aromatic hydrocarbons which may optionally be substituted (e.g. benzene, ligroin, benzine, toluene, xylene, methylene chloride, ethylene chloride, chloroform, carbon tetrachloride, dichloroethane, chlorobenzene, o-dichlorobenzene, etc.), ethers (e.g. dibutyl ether, glycol dimethyl ether, diglycol dimethyl ether, tetrahydrofuran, dioxane, etc.), and ketones (e.g. methyl ethyl ketone etc.). The thus-synthesized 5-thion (=S) compound can be reduced with the aid of Raney nickel to give the 5-methylene compound.

The compound (1) and physiologically acceptable salt of the first embodiment are suitable for the control of parasitic protozoa encountered in the husbandry and/or production of animals such as mammals, birds, fish or insects and show activity against individual or all stages of growth of such pathogenic parasitic protozoa. Furthermore, these compounds show sufficiently effective activity within the usual range of doses against the protozoa which are resistant to the known drugs. As a result, morbidity and the mortality of host animals are decreased and, hence, the efficiency of animal production and reproduction (e.g. the efficiency of production of meat, milk, furs, hides and skins, eggs, honey, etc. as well as the efficiency of breeding) are increased. Moreover, use of the compound of the first embodiment enables economical raising of various animals with good efficiency by preventing protozoal infection such as coccidial infection.

The protozoan diseases that can be controlled by the compound of this first embodiment are of a broad range Thus, the parasitic protozoa that can be controlled include, among others, protozoa of the Apicomplexa, particularly of the family Eimeriidae, such as the genus Eimeria, e.g. *E. acervulina, E. adenoides, E. alabamensis, E. arloingi, E. auburnensis, E. bovis, E. brunetti, E. canis, E. contorta, E. ellipsoidalis, E. falciformis, E. gallopavonis, E. hagani, E. intestinalis, E. magna, E. maxima, E. meleagridis, E. meleagrimitis, E. mitis, E. mivati, E. necatrix, E. ninakohly-akimovae. E. ovis, E. parva, E. pavonis, E. perforans, E. piriformis, E. praecox, E. stiedai, E. suis, E. tenella, E. truncata, E. zuernii*, etc., the genus Isospora such as *I. belli, I. canis, I. felis, I. rivolta, I. suis*, etc., *Toxoplasma gondii*, and the genus Crytosporidium, particularly Cryptosporidium s.p., the family Sarcocystidae, e.g. *S. bovicanis, S. bovihominis, S. ovicanis, S. ovifelis, S. suihominis*, etc., the genus Leucocytozoon, e.g. *L. simondi, L. caulleryi*, etc., the family Plasmodiidae, e.g. *P. berghei, P. falciparum, P. malariae, P. ovale, P. vivax*, etc., protozoa of the subclass Piroplasmea, more specifically of the genus Babesia, e.g. *B. argentina, B. bovis, B. canis*, etc., the genus Theileria, e.g. *T. parva* etc., Adeleina, *Hepatozoon canis* and so on.

Furthermore, protozoa taxonomically belonging to Myxospora or Microspora, protozoa of the genus Glugea and those of the genus Nosema may also be mentioned.

The compound (1) and its physiologically acceptable salt can be used both prophylactically and therapeutically in protozoan infections in mammalian animals (e.g. cattle, horse, swine, sheep, goat, camel, buffalo, donkey, rabbit, deer, reindeer, mink, chinchilla, raccoon, mouse, rat, guinea pig, golden hamster, dog, cat, etc.), birds (e.g. chicken, quail, goose, turkey, duck, wild duck, dove, pigeon, etc.), freshwater and sea-water fishes (e.g. carp, eel, trout, smelt fish, salmon, ruffer, sole, flatfish, sea-bream, sea bass, catfish, etc.) and even in insects such as honey bees.

The compound (1) and its physiologically acceptable salt can be safely administered to any of the above-mentioned animals, either as they are or in various dosage forms according to the route of administration which may be oral or parenteral. The dosage forms mentioned above can be manufactured by the per se known methods (e.g. Japanese patent application unexamined publication No. HS-1047 which corresponds to EP-A-476439, Japanese patent application unexamined publication No. H5-117250 which corresponds to EP-A-457015, Japanese patent application unexamined publication No. H2-240003 which corresponds to EP-A-383285, Japanese patent application unexamined publication No. S62-61972 which corresponds to EP-A-215354, etc.).

The compound of the general formula (1) or physiologically acceptable salt thereof in the first embodiment can be used for preparing a prophylactic and therapeutic agent for protozoal disease by mixing them with a pharmaceutically acceptable additive(s) such as a diluent and an excipient, if necessary, to formulate the antiprotozoal composition according to a known pharmaceutical method, and then incorporated in feed or drinking water for administration.

The antiprotozoal agent of the first embodiment is prepared, for example, by diluting a compound of the general formula (1) or its physiologically acceptable salt, independently or in a mixed state, with a solid or liquid carrier, by undiluting them, or by stabilizing them by coating and the like to formulate powders, dusts, granules, tablets, solutions, emulsions, pastes, capsules, premixed, injections and the like. The antiprotozal agent of the first embodiment is also prepared by dispersing directly the compound of the general formula (1) or its physiologically acceptable salt in feed, drink and the like, or by incorporating therein after dispersed in a carrier. The carrier may be any one, as long as it is physiologically harmless per se. The carriers which function as feed or a component of feed are preferable. The solid carriers include, for example, lactose, sucrose, starch, wheat meal, corn meal, wheat bran, soybean cake, extracted rice bran, rape seed cake, soybean crude meal, cellulose yeast, fish meal, peanut meal, shell powder and calcium carbonate. Examples of the liquid carriers include water, physiological saline and physiologically acceptable organic solvents. In addition, other suitable adjuvants such as emulsifiers, dispersants, suspension aids, wetting agents, thickening agents, gel forming agents and solubilizers may be added in suitable amounts. There may be further incorporated preservatives, fungicides, colorants, aromatics, antibacterial agents, antibiotics, enzyme preparations, lactobacillus preparations, antifebriles, analgesics, antiphlogistics and so on, and other agents for protozoal disease may also be compounded in combination as long as they are different from the compound of the first embodiment in mechanism of action. Furthermore, various vitamins, minerals and amino acids may be incorporated.

The antiprotozoal agents of the first embodiment are administered to animals such as mammals, birds, fish or insects, for the purpose of prophylaxis or/and treating protozoal disease. Since in the live-stock industry, domestic animals are usually bred or farmed in groups, it is also included in the scope of this agents of the first embodiment to infected individuals isolated from the group or to the whole of the group through feed, drinking water and the like, when it has ben confirmed that some animals in the group are attacked with protozoal disease.

The antiprotozoal composition of this first embodiment may contain one or more species of the compound or salt of this first embodiment. Furthermore, the composition may contain other drugs for improving the general condition of animals or drugs for prophylaxis or therapy of the indicated disease. It can be used in combination with such drugs unless adverse interactions or dilution of efficacy is foreseen.

The antiprotozoal composition of this first embodiment should contain compound (I) or a physiologically acceptable salt thereof in a concentration of about 0.01 ppm to about 1%, preferably about 0.1 ppm to about 0.1%. In the case of a preparation for extemporaneous dilution, it is prepared so as to contain the active drug in a concentration of about 0.01 to about 90% or, preferably, about 0.1 to about 30%.

Generally, the antiprotozoal composition of this first embodiment can be administered in a daily dose of about 0.01 to about 50 mg/kg body weight, preferably about 0.1 to about 5 mg/kg body weight, as compound (I) of a salt. By way of illustration, the antiprotozoal composition of this first embodiment can be admixed into the animal ration or diet at the level of, as compound (I) or a salt thereof, about 0.01 to about 100 ppm, preferably about 0.1 to about 50 ppm. The resulting ration can be used for both therapeutic and prophylactic purposes. Such a ration can be generally prepared by manufacturing a concentrate or premix containing about 0.5 to about 30 weight %, preferably about 1 to about 20 weight %, of compound (I) or salt with a feed excipient and blending it with a regular feed. The excipient mentioned just above may for example be a corn meal or corn-soya meal containing a small quantity of some dust-preventive edible oil such as corn oil or soybean oil or a mineral salt. The resulting premix is evenly admixed into a regular animal diet for administration.

For the treatment or prevention of coccidiosis in poultry, particularly in chickens, quails, ducks, wild ducks, geese, and turkeys, generally about 0.01 to about 100 ppm, preferably about 0.1 to about 50 ppm, of compound (I) or salt is administered as previously mixed with suitable edible materials such as nutrient feeds. The drug can be added to drinking water for ingestion.

For the treatment of animals, e.g. for the therapy of coccidiosis or toxoplasmosis, compound (I) or a physiologically acceptable salt thereof is administered in a daily dose of about 0.5 to about 100 mg/kg body weight. Depending on the body weight of animals, therapeutic regimen, species or breeds of animals, individual responses to the antiprotozoal drug, dosage form or formulation, timing and intervals of administration, etc., it may at times be necessary to depart from the above-mentioned dosage range. Thus, a reduced dose may prove effective in some cases, while an increased dose may be necessary in other cases. For massive administration, the daily dosage may be advantageously administered in divided doses.

The treatment of fish is carried out by the oral route, such as through feed, or by the short-time "drug bath" method which comprises transferring the fish from the farming-pond to a tank filled with drug solution (drug bath) and keeping them therein for a predetermined time (ranging from a few minutes to several hours).

However, a temporary or permanent treatment of the whole habitat (for example a pool, aquarium, tank or pond) can also be instituted.

In such cases, compound (I) or a physiologically acceptable salt is applied in a form suited to the particular situation. The concentration of the antiprotozoal agent of this invention may range from about 1 ppm to about 10 weight per volume %.

For the "drug bath" treatment or the omnibus habitat treatment (pool treatment) of fish, it is preferable to employ a solution of the antiprotozoal drug of first embodiment in a polar solvent or solvent mixture which can be diluted or suspended with water.

To prepare such a solution, compound (1) or a physiologically acceptable salt is dissolved or suspended in a polar water-soluble vehicle. It is preferable that after addition of the compound (1) or/and physiologically acceptable salt the vehicle shows a pH range of 7 to 10, especially about 8 to 10.

Since administration of the compound first embodiment controls parasitic protozoan to thereby decrease the incidence of the associated diseases and death and improve the growth retardation and deteriorated general condition, the first embodiment is useful for preventing the decrease of yields in the production of meat, milk, furs, eggs, honey and so on. Moreover, the first embodiment also contributes remarkably to a safe husbandry of ornamental animals and pets.

The following examples, test examples and formulation examples are intended to describe this first embodiment in further detail and should by no means be construed as defining the scope of the first embodiment. The chemical structure of the compound obtained in the following Examples are shown in the Table 3.

TEST EXAMPLE 1

Effect on Biological Test (1)

The anticoccidal affect of the compound of this first embodiment was evaluated in chickens. Using 9-day-old male white Leghorn chicks in groups of 3, the animals in all groups except the non-infected, untreated control group were orally inoculated with $5 \times 10^4$ sporulated oocysts/bird of the laboratory standard strain of *Eimeria tenella*. As the drug, a dried, crushed batch of the compound of this first embodiment was admixed with 31.3 ppm of the standard basal ration (SDL No. 1; Nippon Haigo Shiryo Co., Ltd.) and the chicks were allowed free access to the resulting diet for 9 consecutive days beginning 24 hours before the infection until day 8 after the infection. During the feeding period, the body weight gain of each check was determined. Furthermore, the number of bloody droppings was counted and the count of excreted oocysts was taken to evaluate the anticoccidial effect of the drug. The results are shown in Table 1. In the table, Compound No. corresponds to the Compound No. in Table 3.

TABLE 1

| Compound No. | Relative body weight gain (%)[1] | Number of bloody droppings[2] | OPG[3] (log) |
|---|---|---|---|
| Non-infected/treatment group | 100 | 0 | ND[4] |
| Infected/untreated control group | 40.2 | 3.0 | 5.2 |
| 1 | 100 | 0 | ND |
| 2 | 102.9 | 1.25 | ND |
| 3 | 96.1 | 0 | ND |
| 4 | 91 | 0 | ND |

TABLE 1-continued

| Compound No. | Relative body weight gain (%)[1] | Number of bloody droppings[2] | OPG[3] (log) |
|---|---|---|---|
| 5 | 100 | 0 | ND |
| 6 | 100 | 0 | ND |
| 7 | 104.4 | 0 | ND |
| 15 | 100 | 0 | ND |
| 22 | 111.9 | 0 | ND |
| 38 | 100 | 0 | ND |
| 39 | 100 | 0 | ND |
| 40 | 100 | 0 | ND |
| 43 | 100 | 0 | ND |
| 44 | 100 | 0 | ND |
| 45 | 104.6 | 0 | ND |

[1]Relative body weight gain = $\dfrac{\text{Average body weight gain in treatment group}}{\text{Average body weight gain in non-infected control group}} \times 100$

[2]Number of bloody droppings: The number of blood droppings per bird as detected on the paper set under the floor-net on the peak day of excretion from the intestine of the chick.
[3]OPG: The number of oocysts excreted in 1 gram of feces (on day 7 after infection)
[4]ND: Not detected.

It is apparent from the data in Table 1 that compared with the infected group, the groups treated with the compound of this invention invariably showed a relative body weight gain, indicating that the compound of this first embodiment has excellent anticoccidial activity.

TEST EXAMPLE 2

Effect on the Biological Test (2)

The anticoccidal effect of the compound of the invention was evaluated following the method in the Test Example 1 by administration of the standard ration containing 4 ppm of the compound. The results are shown in Table 2.

TABLE 2

| Compound No. | Relative body weight gain (%) | Number of bloody droppings) | OPG (log) |
|---|---|---|---|
| Non-infected/treatment group | 100 | 0 | ND |
| Infected/untreated control group | 40.2 | 3.0 | 5.2 |
| 53 | 92.3 | 0 | ND |
| 54 | 90.7 | 0 | ND |
| 55 | 92.2 | 0 | ND |
| 56 | 95.7 | 0 | ND |
| 57 | 95.8 | 0 | ND |
| 58 | 95.7 | 0 | ND |
| 59 | 92.2 | 0 | ND |
| 60 | 90.3 | 0 | ND |
| 61 | 90.3 | 0.7 | ND |
| 62 | 94.5 | 0 | ND |
| 65 | 90.0 | 0 | ND |
| 66 | 98.4 | 0 | ND |
| 67 | 92.6 | 0 | ND |
| 68 | 97.0 | 0 | ND |
| 69 | 94.1 | 0.2 | ND |

REFERENCE EXAMPLE 1

3,5-dichloro-4-(4'-chloro-1-methoxycarbonyl)benzyl nitrobenzene

In 100 ml acetonitrile was dissolved 4.00 g p-chlorophenyl acetate, 4.54 g 3,4,5-trichloronitrobenzen and 2.60 g 1,1,3,3-tetramethyl guanidine followed by refluxtion for 8 hours and concentrated to dryness. The residue was dissolved with 100 ml toluene, washed with 100 ml iced water and 100 ml cold water, dried over $MgSO_4$ and concentrated. After the concentrate was added ethanol, 6.82 g of the title compound was filtlated as crystals. m.p. 92–93° C.

REFERENCE EXAMPLE 2

3,5-dichloro-4-(4'-chloro-methoxycarbonyl)benzylaniline

In 50 ml of ethanol was dissolved 6.00 g 3,5-dichloro-4-(4'-chloro-methoxycarbonyl)benzylnitrobenzen prepared according to Reference Example 1 followed by addition of 5-fold molar $SnCl_2$ and refluxed for 2 hours after the reaction solution was concentrated, powdered in 1 l iced water and extracted with 100 ml of ethyl acetate, after the solution was made to be alkaline by adding 10% NaOH. The extract was washed with water, dried over $MgSO_4$ and recrystalized with ethanol to provide 5.12 g of the title compound. m.p. 151–152° C.

REFERENCE EXAMPLE 3

3,5-dichloro-4-(4'-chloro-1-methoxycarbonyl)benzylphenylhydrazine

In the mixture of 100 ml of acetic acid and 30 ml of hydrochloride was dissolved 5.00 g of 3,5-dichloro-4-(4'-chloro-1-methoxycarbonyl)benzylaniline prepared according to Reference Example 2 followed by addition of 10 ml of 2-fold molar sodium nitrate solution dropwise with stirring at 5–10° C.

After completion of the addition, the solution was reacted at 10–20° C. for 2 hours and further reacted at 10–20° C. for 2 hours after addition of 5-fold molar $SnCl_2$ dissolved in 50 ml hydrochloride dropwise with stirring at 5–10° C. The crystals thus obtained was suspended in iced water and extracted with ethyl acetate. The extract was dried over $MgSO_4$, concentrated and recrystalized to give 4.20 g of the title compound. m.p. 113–114° C.

REFERENCE EXAMPLE 4

4-(4'-chloro-1-methoxycarbonyl)benzyl-3-trifluoromethyl aniline

Starting with 4-(4'-chloro-1-methoxycarbonyl)benzyl-3-trifluoromethylnitrobenzene, the title compound was synthesized in otherwise a similar manner as Reference Example 2. m.p. 103–104° C.

REFERENCE EXAMPLE 5

4-(4'-chloro-1-methoxycarbonyl)benzyl-3-trifluoromethylphenyl hydrazine

Starting with 4-(4'-chloro-1-methoxycarbonyl)benzyl-3-trifluoromethylaniline prepared according to Reference Example 4, in otherwise a similar manner as Reference Example 3. m.p. 95–97° C.

EXAMPLE 1

2-(3,5-Dichlorophenyl)-5-methoxy-2,3-dihydro-1,2,4-triazin-3-one (Compound No. 16)

In THF was dissolved 2.77 g of 2-(3,5-dichloro-phenyl)-5-chloro-2,3-dihydro-1,2,4-triazin-3-one followed by addition of sodium methoxide in an equimolar amount to the starting compound, and the mixture was stirred at room temperature for 1 hour. After completion of this reaction, the reaction mixture was concentrated under reduced pressure and ice-water was added to the residue. The resulting crystals were collected by filtration, dried and dissolved in 100 ml of chloroform. The chloroform solution was dried over anhydrous magnesium sulfate, concentrated and purified by column chromatography (Merck Silica Gel 60; dichloromethane-methanol=10:1) to provide 0.4 g of white crystals (m.p. 164° C.).

Elemental analysis for $C_{10}H_7Cl_2N_3O_2$

|  | C | H | N |
|---|---|---|---|
| Calcd.: | 44.14; | 2.59; | 15.44 |
| Found: | 43.92; | 2.61; | 15.31 |

NMR [CDCl$_1$]δ: 4.09 (s, 3H), 7.25–7.48 (m, 1H), 7.51–7.75 (m, 2H).

EXAMPLE 2

2-[3,5-Dichloro-4-(4'-chloro-1-cyanobenzyl)phenyl] hexahydra-1,2,4-triazin-3-one (Compound No. 38)

To 50 ml of dichloromethane was added 2.07 g of 2-[3,5-dichloro-4-(4'-chloro-1-cyanobenzyl)phenyl]-1-(2-hydroxyethyl)semicarbazide as well as 2-fold molar of pyridine. The solution was cooled to 0 to 5° C. and equimolar of trifluoroacetic anhydride was added dropwise with constant stirring. After completion of the dropwise addition, the reaction was further carried out under the same conditions for one hour. The dichloromethane was then removed by concentration and 50 ml of 1,4-dioxane was added to the concentrate. The mixture was refluxed for 4 hours, after which the solvent was distilled off and the residue was dissolved in chloroform. The chloroform solution was washed with iced water, dried over anhydrous magnesium sulfate and concentrated. This residue was further purified by column chromatography (Merck Silica Gel 60; chloroform) to provide 0.1 g of the title compound as a white substance melting at 138–139° C. (dec.).

Elemental analysis for $C_{17}H_{13}Cl_3N_4O$

|  | C | H | N |
|---|---|---|---|
| Calcd.: | 51.60; | 3.31; | 14.16 |
| Found: | 51.53; | 3.36; | 14.14 |

NMR [CDCl$_3$] 67 : 3.00–3.64 (m, 4H), 4.19 (t, J=6 Hz, 1H), 5.69 (br, 1H), 6.09 (s, 1H), 7.29 (s, 4H), 7.92 (s, 2H).

EXAMPLE 3

2-[3,5-Dichloro-4-(4'-chloro-1-cyanobenzyl)phenyl]-2,3,4,5-tetrahydro-1,2,4-triazin-3-one (Compound No. 41)

Starting with 2.00 g of 2-[3,5-dichloro-4-(4'-chloro-1-cyanobenzyl)phenyl]-1-(2-hydroxymethylmethylidene semicarbazone, 0.38 g of the white title compound was synthesized in otherwise the same manner as Example 2. m.p. 166–167° C. Elemental analysis for $C_{17}H_{11}Cl_3N_4O$

|  | C | H | N |
|---|---|---|---|
| Calcd.: | 51.86; | 2.82; | 14.23 |
| Found: | 51.60; | 2.87; | 13.93 |

NMR [CDCl$_3$] δ: 4.00–4.20 (m, 2H), 6.14 (s, 1H), 6.45 (br, 1H), 7.15 (br, 1H), 7.30 (s, 4H), 7.72 (s, 2H).

EXAMPLE 4

2-[3,5-Dichloro-4-(4-chloro-1'-cyanobenzyl)phenyl]-4-methylhexahydro-1,2,4-triazin-3-one (Compound No. 40)

In 50 ml of dimethylformamide was dissolved 1.18 g of 1-methyl-1-(2,2-diethoxyethyl)-2-[3,5-dichlora-4-(4'-chloro-1-cyanobenzyl)phenyl]semicarbazide and the reaction was carried out at 140–145° C. with stirring for 2 hours. The reaction mixture was then poured in 300 ml of iced water and extracted with 200 ml of chloroform. The extract was dried over anhydrous magnesium sulfate, concentrated to dryness. The residue was reducted with LiAlH$_4$ in THF and purified by column chromatography (Merck Silica Gel 60; chloroform) to provide 0.1 g of the title compound. m.p. 137–138° C.

Elemental analysis for $C_{18}H_{15}Cl_3N_4O$

|  | C | H | N |
|---|---|---|---|
| Calcd.: | 52.77; | 3.69; | 13.68 |
| Found: | 52.74; | 3.62; | 13.68 |

NMR [CDCl$_3$] δ: 3.00 (s, 3H), 3.20–3.60 (m, 4H), 4.25 (br, 1H), 6.08 (s, 1H), 7.28 (s, 4H), 7.89 (s, 2H).

EXAMPLE 5

2-(3,5-Dichlorophenyl)-2,3,4,5-tetrahydro-1,2,4-triazin-3-one-5-thione (Compound No. 7)

To 100 ml of toluene was added 2.58 g of the starting compound 3,5-dione as well as ½ equivalent of Lawesson's reagent and the mixture was refluxed for 5 hours. The reaction mixture was then concentrated and purified by column chromatography (Merck Silica Gel 60; chloroform) to provide 0.9 g of light-yellow crystals, m.p. 200–201° C.

Elemental analysis for $C_9H_5Cl_2N_3OS$

|  | C | H | N |
|---|---|---|---|
| Calcd.: | 39.43; | 1.84; | 15.33 |
| Found: | 39.45; | 1.97; | 15.05 |

NMR [CDCl$_3$] δ: 7.67 (s, 3H), 7.84 (s, 1H), 13.80 (br, 1H).

EXAMPLE 6

2-(3,5-Dichlorophenyl)-2,3,4,5-tetrahydro-1,2,4-triazin-3-one (Compound No. 1)

In 50 ml of 70% ethanol was dissolved 2.74 g of Compound No. 7, synthesized in Example 5, followed by addition of 10 equivalents of activated Raney nickel. The mixture was stirred at room temperature overnight, after which the insoluble matter was filtered off. The filtrate was concentrated under reduced pressure and the residue was dissolved in 100 ml of ethyl acetate. This solution was dehydrated over anhydrous magnesium sulfate, concentrated and the resulting red-brown oil was purified by column chromatography (Merck Silica Gel 60; chloroform) to provide 1.0 g of the title compound as a pale yellow substance. m.p. 179–181° C.

Elemental analysis for $C_9H_7Cl_2N_3O$

|  | C | H | N |
|---|---|---|---|
| Calcd.: | 44.29; | 2.89; | 17.22 |
| Found: | 44.59; | 2.98; | 17.41 |

NMR [$CDCl_3$] δ: 4.05–4.20 (m, 2H), 6.30–6.60 (br, 1H), 7.00–7.30 (m, 2H), 7.52 (d, J=2 Hz, 2H).

EXAMPLE 7

2-(3,5-Dichlorophenyl)-5-phenyl-2,3-dihydro- 1,2,4-triazin-3-one (Compound No. 27)

In 50 ml of dioxane was dissolved 2.20 g of 2-(3,5-dichlorophenyl)semicarbazide followed by addition of 1.52 g of phenylglyoxal monohydrate, and the mixture was refluxed for 5 hours. The reaction mixture was then concentrated and the residue was recrystallized from acetonitrile to provide 1.34 g of the title compound. m.p. 160–161° C.

Elemental analysis for $C_{15}H_9Cl_2N_3O$

|  | C | H | N |
|---|---|---|---|
| Calcd.: | 56.63; | 2.85; | 13.21 |
| Found: | 56.52; | 2.78; | 13.34 |

NMR [$CDCl_3$] δ: 7.38 (t, J=2 Hz, 1H), 7.45–7.70 (m, 3H), 7.75 (d, J=2 Hz, 2H), 8.05–8.30 (m, 2H), 8.48 (s, 1H).

EXAMPLE 8

Starting with 2-(3,5-dichlorophenyl)-1-(2-hydroxy-2-methylpropylidene)semicarbazone, Compound 2 was synthesized in otherwise a similar manner as Example 2. m.p. 120–122° C.

EXAMPLE 9

Starting with 2-(3,5-dichlorophenyl)-1-(2-hydroxy-2-methylthioethylidene)semicarbazone, Compound 3 was synthesized in otherwise a similar manner as Example 2. m.p. 115–116° C.

EXAMPLE 10

Starting with 2-(3,5-dichlorophenyl)-1-(2,2-dimethylthio-2-hydroxyethyl)semicarbazide, Compound 4 was synthesized in otherwise a similar manner as Example 2. m.p. 151–152° C.

EXAMPLE 11

Starting with Compound 1, Compound 5 was synthesized in otherwise a similar manner as Example 4. m.p. 148–149° C.

EXAMPLE 12

Starting with 2-(3,5-dichlorophenyl)-6-methyl- 2,3,4,5-tetrahydro-1,2,4-triazin-3-one-5-thione, Compound 6 was synthesized in otherwise a similar manner as Example 6. m.p. 164–165° C.

EXAMPLE 13

Starting with 2-(3,5-dichlorophenyl)-4-methylhexahydro-1,2,4-triazin-3,5-dione, Compound 8 was synthesized in otherwise a similar manner as Example 5. m.p. 149–150° C.

EXAMPLE 14

Starting with 2-(3,5-dichlorophenyl)-hexahydro-1,2,4-triazin-3,5-dione, Compound 9 was synthesized in otherwise a similar manner as Example 5. m.p. 221–223° C. (dec).

EXAMPLE 15

Starting with 2-(3,5-dichlorophenyl)-1-(2-hydroxy-2-phenylethyl)semicarbazide, Compound 10 was synthesized in otherwise a similar manner as Example 2. m.p. 164–165° C.

EXAMPLE 16

Starting with 2-(3,5-dichlorophenyl)-1-(2-hydroxy-2-phenylethylidene)semicarbazone, Compound 11 was synthesized in otherwise a similar manner as Example 2. m.p. 139–140° C.

EXAMPLE 17

Starting with Compound 8, Compound 12 was synthesized in otherwise a similar manner as Example 6. m.p. 210–211° C.

EXAMPLE 18

Starting with 2-(3,5-dichlorophenyl)-6-methylhexahydro-1,2,4-triazin-3-one-5-thione, Compound 13 is synthesized in otherwise a similar manner as Example 6.

EXAMPLE 19

Using methyl mercaptan in place of sodium methoxide, Compound 14 was synthesized in otherwise a similar manner as Example 1. m.p. 190–191° C.

EXAMPLE 20

Using benzyl mercaptan in place of sodium methoxide, Compound 15 was synthesized in otherwise a similar manner as Example 1. m.p. 152–153° C.

EXAMPLE 21

5-chloro-2-(3,5-dichlorophenyl)-2,3-dihydro-1,2,4-triazine-3-one (compound No. 17)

In 30 ml of dichloromethane suspended with 1.00 g of 2-(3,5-dichlorophenyl)-2,3,4,5-tetrahydro-1,2,4-triazine-3,5-dione followed by addition of 2-fold morlar each of carbone tetrachloride and triphenylphosphine and refluxed for 12 hours. After the completion of the reaction, the resulted solution were purified by colomun chlomatography (Merck Silica Gel 60 dichloromethane-carbontetrachloride= 2:1). m.p. 148–149° C.

NMR [$CDCl_3$] δ: 7.42(t,J=2 Hz,1H), 7.66(d,J=2 Hz,2H), 7.91(s, 1H)

EXAMPLE 22

Using potassium fluoride in place of sodium methoxide, Compound 18 was synthesized in otherwise a similar manner as Example 1. m.p. 93–95° C.

EXAMPLE 23

Using p-chlorothiophenol in place of sodium methoxide, Compound 19 was synthesized in otherwise a similar manner as Example 1. m.p. 176–178° C.

EXAMPLE 24

Using t-butyl mercaptan in place of sodium methoxide, Compound 20 was synthesized in otherwise a similar manner as Example 1. m.p. 97–99° C.

EXAMPLE 25

Using potassium t-butoxide in place of sodium methoxide, Compound 21 was synthesized in otherwise a similar manner as Example 1. m.p. 91–92° C.

EXAMPLE 26

Using phenol in place of sodium methoxide, Compound 22 was synthesized in otherwise a similar manner as Example 1. m.p. 126–127° C.

EXAMPLE 27

Using cyclopropylmethamol in place of sodium methoxide, Compound 23 was synthesized in otherwise a similar manner as Example 1. m.p. 68–69° C.

EXAMPLE 28

Using 2-fluoroethanol in place of sodium methoxide, Compound 24 was synthesized in otherwise a similar manner as Example 1. m.p. 110–111° C.

EXAMPLE 29

Using 2,2,2-trifluoroethanol in place of sodium methoxide, Compound 25 was synthesized in otherwise a similar manner as Example 1. m.p. 80–81° C.

EXAMPLE 30

Using 1,3-dimercaptopropane in place of sodium methoxide, Compound 26 was synthesized in otherwise a similar manner as Example 1. m.p. 195–196° C.

EXAMPLE 31

Starting with 2-(3,5-dichlorophenyl)-5-chloro-2,3,4,5-tetrahydro-1,2,4-triazin-3-one and using methyl mercaptan in place of sodium methoxide, Compound 3 was synthesized in otherwise a similar manner as Example 1. m.p. 115–116° C.

EXAMPLE 32

Using 2-(3,5-dichlorophenyl)-1-benzoylmethylidenesemicarbazone, Compound 27 was synthesized in otherwise a similar manner as Example 2. m.p. 160–161° C.

EXAMPLE 33

Using 2-(3,5-dichlorophenyl)-1-benzoyl-1-phenylmethylidenesemicarbazone, Compound 28 was synthesized in otherwise a similar manner as Example 2. m.p. 158–159° C.

EXAMPLE 34

Starting with 2-(3,5-dichlorophenyl)-5-chloro- 1,2,3,6-tetrahydro-1,2,4-triazin-3-one and using methyl mercaptan in place of sodium methoxide, Compound 29 was synthesized in otherwise a similar manner as Example 1. m.p. 133–134° C.

EXAMPLE 35

Using 2-phenyl-2,3,4,5-tetrahydro-1,2,4-triazin-3,5-dione, Compound 30 was synthesized in otherwise a similar manner as Example 5. m.p. 183–184° C.

EXAMPLE 36

Starting with 2-phenyl-5-chloro-2,3-dihydro-1,2,4-triazin-3-one and using methyl mercaptan in place of sodium methoxide, Compound 31 was synthesized in otherwise a similar manner as Example 1. m.p. 115–116° C.

EXAMPLE 37

Starting with 2-phenyl-5-chloro-2,3-dihydro-1,2,4-triazin-3-one, Compound 32 was synthesized in otherwise a similar manner as Example 1. m.p. 102–103° C.

EXAMPLE 38

Using 2-(4-chlorophenyl)-2,3,4,5-tetrahydro-1,2,4-triazin-3,5-dione, Compound 33 was synthesized in otherwise a similar manner as Example 5. m.p. 198–199° C.

EXAMPLE 39

Starting with 2-(4-chlorophenyl)-5-chloro-2,3-dihydro-1,2,4-triazin-3-one and using methyl mercaptan in place of sodium methoxide, Compound 34 was synthesized in otherwise a similar manner as Example 1. m.p. 168–169° C.

EXAMPLE 40

Using 2-(4-chlorophenyl)-5-chloro-2,3-dihydro-1,2,4-triazin-3-one, Compound 35 was synthesized in otherwise a similar manner as Example 1. m.p. 151–152° C.

EXAMPLE 41

Using 2-[3,5-dichloro-4-(4'-chloro- 1-cyanobenzyl)-phenyl]-2,3,4,5-tetrahydro-1,2,4-triazin-3,5-dione, Compound 36 was synthesized in otherwise a similar manner as Example 5. m.p. 249–250° C.

EXAMPLE 42

Using 2-[3,5-dichloro-4-(4'-chloro-1-cyanobenzyl)-phenyl]hexahydro-1,2,4-triazin-3,5-dione, Compound 37 was synthesized in otherwise a similar manner as Example 5. m.p. 215–216° C. (dec).

EXAMPLE 43

Using 2-[3,5-dichloro-4-(4'-chloro-1-cyanobenzyl)-phenyl]-4-methyl-2,3,4,5-tetrahydro-1,2,4-triazin-3-one-5-thione, Compound 40 was synthesized in otherwise a similar manner as Example 6. m.p. 137–138° C.

EXAMPLE 44

Using 2-[3,5-dichloro-4-(4'-chloro-1-cyanobenzyl)-phenyl]-5-chloro-2,3-dihydro-1,2,4-triazin-3-one, Compound 42 was synthesized in otherwise a similar manner as Example 1. m.p. 193–194° C.

EXAMPLE 45

Compound 36 was dissolved in THF and reacted with equimolar of methyl iodide to provide Compound 43. m.p. 204–205° C.

EXAMPLE 46

Compound 43 was dissolved in dichloromethane and reacted with chlorine gas to provide Compound 44. m.p. 184–185° C.

EXAMPLE 47

2-(3,5-dichlorophenyl)-2,3,4,5-tetrahydro-1,2,4-triazin-3-one (compound No. 1)

In 20 ml acetonitrile was dissolved 1.77 g of 3,5-dichlorophenylhydrazine followed by addition of 1.10 g benzaldehyde dropwise with constant stirring at 10 to 20° C. and obtained 2.70 g hydrazone. In 30 ml of acetonitrile was dissolved 1.33 g of the hydrazone followed by the addition of 3-fold mole pyridine, and 0.6-fold mole trichlolomethyl-chloroformate was added dropwise to the mixture with constant stirring at 0 to 10° C. After completion of the dropwise addition, the mixture was stirred at 20 to 25° C. for 1 hour.

In 30 ml acetonitrile was dissolved 0.60 g of aminoacetoaldehyde dimethyl acetate followed by the addition of the above prepared reaction solution with constant stirring at 5 to 10° C. After completion of the dropwise addition, the reaction solution was stirred at 20 to 25° C. for 3 hours. After concentrated the thus obtained reaction solution, iced water was added and extracted with 50 ml of dichloromethane. After dried over anhydrous magnesium sulfate, the extract was concentrated and purified by column chromatography (Merck Silica Gel 60; chloroform) to provide 1.54 g of 1-benzilidene-2-(3,5-dichlorphenyl)-4-(2,2-dimethoxyethyl)semicarbazone as white crystals (m.p. 119–120° C.).

In 20 ml acetonitrile was dissolved 1.00 g of the thus obtained semicarbazone, followed by heat-reaction at 50 to 60° C. with 0.1 ml conc. hydrochloride for 20 minutes. After completed the reaction, the resulted crystal was collected by filtration and washed with water. Thus obtained crystal was recrystallized from ethyl acetate to provide 0.72 g the title compound. m.p. 179–181° C. N.

EXAMPLE 48

2-[3,5-dichloro-4-(4-chlorophenylthio)phenyl]-6-methyl-2,3,4,5-tetrahydro-1,2,4-triazin-3-one (compound No. 45)

After refluxed 1.60 g of 3,5-dichloro-4-(4-chlorophenylthio)phenylhydrazone and 0.9 g of N-acetonylphenylcarbamate in 30 ml toluene, 0.8 g of 1,8-diazabicyclo[5,4,0]-7-undensen was added therein and refluxed 2 more hours. After completed the reaction, the solution was concentrated, added ice water and extracted from 50 ml of dichloromethane. After dried over with anhydrous magnesium sulfate, the extract was concentrated to dryness and purified by column chromatography (Merck Silica Gel 60; chloroform) to provide 0.34 g of the title compound as a white substance. m.p. 258–259° C.

NMR ($d_6$-DMSO)δ: 2.04(s,3H), 3.98(br-d,J=2 Hz,2H), 7.22(g,J=8 Hz,4H), 7.80(br,1H), 7.88(s,2H).

EXAMPLE 49

2-[3,5-dichloro-4-(4-chlorobenzoyl)phenyl]-6-methyl-2,3,4,5-tetrahydro-1,2,4-triazin-3-one (compound No. 46)

Starting with 3,5-dichloro-4-(4-chlorobenzoyl) phenylhydrazine, the title compound was synthesized in otherwise a similar manner as Example 48. m.p. 257–259° C.

EXAMPLE 50

4-acetyl-2-[3,5-dichloro-4-(4-chlorobenzyl)phenyl]-6-methyl-2,3,4,5-tetrahydro-1,2,4-triazin-3-one (compound No. 47)

The title compound was obtained by acetylating the compound 46 prepared according to Example 49 with acetic acid anhydride in toluene. m.p. 101–102° C.

EXAMPLE 51

2-(3,5-dichlorophenyl)-1-methyl-hexahydro-1,2,4-triazin-3-one(compound No. 49)

Chrystals obtained by reacting 1-aminoacethyl-1-methyl-2-(3,5-dichrolophenyl) hydrazine with phenyl chloroformate under the existance of a base was dissolved in THF followed by reduction with $NaBH_4$ to provide the title compound m.p. 150–151° C.

EXAMPLE 52

6-chloro-2-(3,5-dichlorophenyl)-2,3,4,5-tetrahydro-1,2,4-triazin-3-thione (compound No. 49)

In 30 ml dichloromethane 1.33 g of 1-(3,5-dichlorophenyl)-2-benzyldenhydrazone and 5-fold molar pyridine were dissolved followed by addition of 2-fold molar thiophosgen dropwise with constant stirring at 5 to 10° C. After completed the dropwise addition, the resulting solution was stirred at 20 to 25 for 1 hour and added the equimolar ethylglcinate hydrochloride salt with stirring at 5 to 10° C. After two hour reaction, the reaction solution was washed with water and concentrated to dryness. The residue was dissolved in 30 ml of acetonitrile and reacted with 0.1 ml conc. hydrochloride at 50 to 60° C. for 20 minutes to provide 2-(3,5-dichlorophenyl)-hexahydro-1,2,4-triazin-6-one-3-thion. The resulted compound was chlorized by known manner to provided the title compound. m.p. 207–208° C.

EXAMPLE 53

2-[3,5-dichlorophenyl)-1,5-dimethylhexahydro-1,2,4-triazin-3-one (compound No. 50)

Reacting 1-(2-aminopropyl)-1-methyl-2-(3,5-dichlorophenyl)hydrazine with phenyl chloroformate under presence of base to provide the title compound. m.p. 129–130° C.

EXAMPLE 54

2-(3,5-dichlorophenyl)-1-methyl-hexahydro-1,2,4-triazin-3-thione (compound No. 51)

Starting with 1-(2-aminoethyl)-2-(3,5-dichlorophenyl) methylhydrazide and thiophosgene, the title compound was synthesized in otherwise a similar manner as Example 52. m.p. 240–241° C.

EXAMPLE 55

2-[3-chloro-4-(4'-chloro-1-cyanobenzyl)-5-methylphenyl]-2,3,4,5-tetrahydro-1,2,4-triazin-3-one (compound No. 52)

Starting with 3-chloro-4-(4'-chloro-1-cyanobenzyl)-5-methylphenylhydrazine, the title compound was synthesized in otherwise a similar manner as Example 47. m.p. 192–193° C.

EXAMPLE 56

2-[3-Chloro-4-(4'-chloro-1-cyanobenzyl)-5-methylphenyl]-hexahydro-1,2,4-triazin-3-one (compound No. 53)

Reducing the compound 52 prepared according to Example 55 with LiAlH$_4$ in THF to provide the title compound. m.p. 201–202° C.

EXAMPLE 57

2-[3-chloro-4-(4'-chloro-1-cyanobenzyl)-5-methylphenyl]-2,3,4,5-tetrahydro-1,2,4-triazin-3-one-5-thione (compound No. 54)

Starting with 2-[3-chloro-4-(4'-chloro-1-cyanobenzyl)-5-methylphenyl]-2,3,4,5-tetrahydro-1,2,4-triazine-3,5-dione, the title compound was synthesized in otherwise a similar manner as Example 5. m.p. 234–236° C.

NMR (d$_6$-DMSO)δ: 2.41(s,3H), 6.36(s,1H), 7.17–7.70 (m,6H), 7.87(s,1H), 13.86(br,1H).

EXAMPLE 58

2-[3-chloro-4-(4'-chloro-1-cyanobenzyl)-5-methylphenyl]hexahydro-1,2,4-triazine-3-one-5-thione (compound No. 55)

Reducing the compound 54 prepared according to Example 57 with LiALH$_4$ in THF to provide the title compound. m.p. 217–218° C.

EXAMPLE 59

2-[3,5-dichloro-4-(4'-chloro-1-benzoyl)phenyl]-2,3,4,5-tetrahydro-1,2,4-triazin-3-one (compound No. 56)

Starting with 3,5-dichloro-4-(4'-chlorobenzoyl)phenylhydrazine, the title compound was synthesized in otherwise a similar manner as Example 47. m.p. 212–213° C.

EXAMPLE 60

2-[3,5-dichloro-4-(4'-chloro-1-hydroxybenzyl)phenyl]- 2,3,4,5-tetrahydro-1,2,4-triazin-3-one (compound No. 57)

Reducing the compound 56 prepared according to Example 59 with LiAlH$_4$ in THF to provide the title compound. m.p. 115–116° C.

EXAMPLE 61

2-[3-chloro-4-(4-chlorobenzoyl)phenyl]-2,3,4,5-tetrahydro-1,2,4-triazin-3-one (compound No. 58)

Starting with 3-chloro-4-(4-chlorobenzoyl) phenylhydrazine, the title compound was synthesized in otherwise a similar manner as Example 47. m.p. 158–159° C.

EXAMPLE 62

2-[3-chloro-4-(4'-chloro-1-hydroxybenzyl)phenyl]-2,3,4,5-tetrahydro-1,2,4-triazin-3-one (compound No. 59)

The compound 58 prepared according to Example 61 was reduced with LiAlH$_4$ in THF to provide the title compound. m.p. 135–136° C.

EXAMPLE 63

2-[3,5-dichloro-4-(4-chlorophenylthio)phenyl]-2,3,4,5-tetrahydro-1,2,4-triazin-3-one (compound No. 60)

Starting with 3,5-dichloro-4-(4-chlorophenylthio) phenylhydrazine, the title compound was synthesized in otherwise a similar manner as Example 47. m.p. 224–225° C.

EXAMPLE 64

2-[4-(4-chlorobenzyl)-3-chlorophenyl]-2,3,4,5-tetrahydro-1,2,4-triazin-3-one (compound No. 61)

Starting with 3-chloro-4-(4-chlorobenzyl)phenylhydrazine, the title compound was synthesized in otherwise a similar manner as Example 47. m.p. 196–197° C.

EXAMPLE 65

2-[3-chloro-4-(2-chloropyridin-5-yl-cyanomethyl)-5-methylphenyl]-2,3,4,5-tetrahydro-1,2,4-triazin-3-one (compound No. 62)

Starting with 3-chloro-4-(2-chloropyridin-5-yl-cyanomethyl)-5-methylphenylhydrazine, the title compound was synthesized in,otherwise a similar manner as Example 47. m.p. 211–212° C.

EXAMPLE 66

2-[3-chloro-4-(2-chlorothiazol-5-yl-cyanomethyl)-5-methylphenyl]-2,3,4,5-tetrahydro-1,2,4-triazin-3-one (compound No. 63)

Starting with 3-chloro-4-(2-chlorothiazol-5-yl-cyanomethyl)-5-methylphenylhydrazine, the title compound was synthesized in otherwise a similar manner as Example 47. m.p. 238–239° C.

EXAMPLE 67

2-[3-chloro-4-(1-methylimidazol-2-yl-thio)-5-methylphenyl]-2,3,4,5-tetrahydro-1,2,4-triazin-3-one (compound No. 64)

Starting with 3-chloro-4-(1-methylimidazol-2-yl-thio)-5-methylphenylhydrazine, the title compound was synthesized in otherwise a similar manner as Example 47. m.p. 173–174° C.

EXAMPLE 68

2-[3,5-dichloro-4-(4'-chloro-1-fuluorobenzyl)phenyl]-2,3,4,5-tetrahydro-1,2,4-triazin-3-one (compound No. 65)

In 20 ml dichloromethane was suspended 0.38 g of the compound 57 followed by addition of 0.16 g of diethylaminosulfurtrifuluoride (DAST) dissolved in 5 ml dropwise with constant stirring at about −50° C. After reacted for 30 minutes under same condition, the reaction solution was further reacted at 20–25° C. for 1 hour and concentrated. The residue was purified by column chromatography (Merck Silica Gel 60; chloroform) to provide 0.22 g of the title compound. m.p. 182–183° C.

NMR (CDCl$_3$) δ: 4.09(t,J=2 Hz,2H), 6.65(br,1H), 7.12(t, J=2H$_2$,1H), 7.22(d,J=46 Hz,1H), 7.30(s,4H), 7.67(d,J=2 Hz,2H).

EXAMPLE 69

2-[3-chloro-4-(4-chloro-1-fuluorobenzyl)pheny]-2,3,4,5-tetrahydro-1,2,4-triazin-3-one (compound No. 66)

Starting with 2-(3-chloro-4-(4'-chloro-1-hydroxybenzyl)pheny]-2,3,4,5-tetrahydro-1,2,4-triazin-3-one, the title compound was synthesized in otherwise a similar manner as Example 68. m.p. 124–125° C.

EXAMPLE 70

2-[3,5-dichloro-4-(4'-chlorobenzyl)phenyl]-2,3,4,5-tetrahydro-1,2,4-triazin-3-one (compound No. 67)

Starting with 3,5-dichloro-4-(4-chlorobenzyl)phenylhydrazine the title compound was synthesized in otherwise a similar manner as Example 47. m.p. 196–197° C.

EXAMPLE 71

2-[3,5-dichloro-4-(4-chlorophenylthio)phenyl]hexahydro-1,2,4-triazin-3-one (compound No. 68)

The compound 60 was reduced with $LiAlH_4$ in THF to provide the title compound. m.p. 242–243° C.

EXAMPLE 72

2-[4-(4-chlorobenzyl)-3-chlorophenyl]hexahydro-1,2,4-triazin-3-one (compound No. 69)

The compound 61 was reduced with $LiAlH_4$ in THF to provide the title compound. m.p. 157–158° C.

EXAMPLE 73

2-(2-chloro-4-trifluoromethylpyridin-6-yl)-2,3,4,5-tetrahydro-1,2,4-triazin-3-one (compound No. 70)

Starting with 2-chloro-4-trifluoromethylpyridin-6-yl-hydrazine, the title compound was synthesized in otherwise a similar manner as Example 47. m.p. 197–198° C.

EXAMPLE 74

2-(2-chloro-4-trifluoromethyl-pyridin-6-yl) hexahydro-1,2,4-triazin-3-one (compound No. 71)

The compound 70 prepared according to Example 73 was reduced with $LiAlH_4$ in THF to provide the title compound. m.p. 191–192° C.

EXAMPLE 75

2-[3,5-dichloro-4-[2-(4-chlorophenyl)-1-cyanoethyl]phenyl]-2,3,4,5-tetrahydro-1,2,4-triazin-3-one (compound No. 72)

Starting with 3,5-dichloro-4-[2-(4-chlorophenyl)-1-cyanoethyl]phenylhydrazine, the title compound was synthesized in otherwise a similar manner as Example 47. m.p. 213–213° C.

EXAMPLE 76

2-[3,5-dichloro-4-(4'-chloro-1-methoxycarbonylbenzyl)phenyl]-2,3,4,5-tetrahydro-1,2,4-triazin-3-one (compound No. 73)

Starting with 3,5-dichloro-4-(4'-chloro-1-methoxycarbonylbenzyl)phenylhydrazine, the title compound was synthesized in otherwise a similar manner as Example 47. m.p. 206–207

EXAMPLE 77

2-[3,5-dichloro-4-(4'-chloro-1-hydroxymethylbenzyl)phenyl]hexahydro-1,2,4-triazin-3-one (compound No. 88)

The compound 73 prepared according to Example 76 was reduced with $LiAlH_4$ in THF to provide the title compound. m.p. 108–109° C.

NMR ($CDCl_3$) δ; 3.00–3.60(br,4H), 4.00–4.70(br-m,4H), 5.12(t,1H), 5.88(br-s,1H), 7.19(s,4H), 7.73(s,2H).

EXAMPLE 78

2-[3-trifluoromethyl-4-(4'-chloro-1-methoxycarbonylbenzyl)phenyl]-2,3,4,5-tetrahydro-1,2,4-triazin-3-one (compound No. 74)

Starting with 3-trifluoromethyl-4-(4'-chloro-1-methoxycarbonylbenzyl)phenylhydrazine, the title compound was synthesized in otherwise a similar manner as Example 47. m.p. 118–119° C.

EXAMPLE 79

2-[3-chloro-4-(4-chlorobenzyl)-5-methylphenyl]-2,3,4,5-tetrahydro-1,2,4-triazin-3-one (compound No. 89)

Starting with 3-chloro-4-(4-chlorobenzyl)-5-methylphenylhydrazine, the title compound was synthesized in otherwise a similar manner as Example 47. m.p. 209–210° C.

EXAMPLE 80

2-[3-chloro-4-(4-chlorobenzyl)-5-methylphenyl] hexahydro-1,2,4-triazin-3-one (compound No. 90)

The compound 89 prepared according to Example 79 was reduced with $LiAlH_4$ in THF to provide the title compound. m.p. 197–198° C.

EXAMPLE 81

2-[3-chloro-4-(4'-chloro-1-fluorobenzyl)-5-methylphenyl]hexahydro-1,2,4-triazin-3-one (compound No. 91)

Starting with 3-chloro-4-(4'-chloro-1-fluorobenzyl)-5-methylphenylhydrazine, the title compound was synthesized in otherwise a similar manner as Example 47. m.p. 160–161° C. (dec).

EXAMPLE 82

2-[3-chloro-4-(4'-chlorophenoxy)-5-methylphenyl] hexahydro-1,2,4-triazin-3-one (compound No. 92)

Starting with 3-chloro-4-(4'-chlorophenoxy)-5-methylphenylhydrazine, the title compound was synthesized in otherwise a similar manner as Example 47 and reduced with $LiAlH_4$ in THF. m.p. 188–189° C.

EXAMPLE 83

2-[3-chloro-4-(4'-chlorobenzylthio)-5-methylphenyl] hexahydro-1,2,4-triazin-3-one (compound No. 93)

Starting with 3-chloro-4-(4'-chlorobenzylthio)-5-methylphenylhydrazine, the title compound was synthesized in otherwise a similar manner as Example 82. m.p. 165–167° C.

EXAMPLE 84

2-{3-chloro-4-[2-(4'-chlorophenyl)-2-cyanovinylen]-5-methylphenyl}-2,3,4,5-tetrahydro-1,2,4-triazin-3-one (compound No. 94)

Starting with 3-chloro-4-[2-(4'-chlorophenyl)-2-cyanovinylene]-5-methylphenylhydrazine, the title compound was synthesized in otherwise a similar manner as Example 47. m.p. 250–251° C.

EXAMPLE 85

2-[3-trifluoromethyl-4-(4'-chloro-1-hydroxymethylbenzyl)phenyl]-2,3,4,5-tetrahydro-1,2,4-triazin-3-one (compound No. 95)

The compound 74 prepared in Example 78 was reduced with $LiAlH_4$ in THF to provide the title compound. m.p. 76–77° C.
Further reduction of the title compound in THF with $LiAlH_4$, and obtained 2-[3-trifluoromethyl-4-(4'-chloro-1-hydroxymethylbenzyl)phenyl]-hexahydro-1,2,4-triazin-3-one (compound No. 77). m.p. 87–88° C.

EXAMPLE 86

2-[3,5-dichloro-4-(4'-chloro-1-cyanobenzyl)phenyl]-6-methyl-2,3,4,5-tetrahydro-1,2,4-triazin-3-one (compound No. 39)

Starting with 3,5-dichloro-4-(4'-chloro-1-cyanobenzyl) phenylhydrazine is disolved into toluene and heated with acetonylamine for two hours. After adding equimolar of phenyl chloroformate, the result solution was heated for farther two hours. After completion of the reaction, the reaction solution is cooled and filtrated to provide the title compound as crystal.

EXAMPLE 87

2-[3-trifluoromethyl-4-(4'-chloro-1-fluoromethylbenzyl)phenyl]-2,3,4,5-tetrahydro-1,2,4-triazin-3-one (compound No. 75)

Starting with compound 77, the title compound was synthesized in otherwise a similar manner as Example 68. m.p. 163–164° C.

EXAMPLE 88

2-[3,5-dichloro-4-(4'-chloro-1-methylthiomethylbenzyl)phenyl]-2,3,4,5-tetrahydro-1,2,4-triazin-3-one (compound No. 96)

In methanol, 2-[3,5-dichloro-4-(4'-chloro-1-chloromethylbenzyl)phenyl]-2,3,4,5-tetrahydro-1,2,4-triazin-3-one is reacted with sodium thiomethoxide to provide the title compound.

EXAMPLE 89

2-[3,5-dichloro-4-(4'-chloro-1-dimethylaminomethylbenzyl)phenyl]-2,3,4,5-tetrahydro-1,2,4-triazin-3-one (compound No. 97)

In dimethylformamide, 2-[3,5-dichloro-4-(4'-chloro-1-chloromethylbenzyl)phenyl]-2,3,4,5-tetrahydro-1,2,4-triazin-3-one is reacted with dimethylamine solution.

EXAMPLE 90

2-[3,5-dichloro-4-(4'-chloro-1-trifluoromethylbenzyl)phenyl]-2,3,4,5-tetrahydro-1,2,4-triazin-3-one (compound No. 98)

Starting with 3,5-dichloro-4-(4'-chloro-1-trifluoromethylbenzyl)phenylhydrazine, the title compound is synthesized in otherwise a similar manner as Example 47.

EXAMPLE 91

2-[3,5-dichloro-4-(4'-chloro-1-hydroxymethylbenzyl)phenyl]-2,3,4,5-tetrahydro-1,2,4-triazin-3-one (compound 99)

Starting with 3,5-dichloro-4-(4'-chloro-1-hydroxymethylbenzyl)phenylhydrazine, the title compound is synthesized in otherwise a similar manner as Example 47.

EXAMPLE 92

2-[3,5-dichloro-4-(4'-chloro-1-fluoromethylbenzyl)phenyl]-2,3,4,5-tetrahydro-1,2,4-triazin-3-one (compound No. 100)

Starting with 2-[3,5-dichloro-4-(4'-chloro-1-hydroxymethylbenzyl)phenyl]-2,3,4,5-tetrahydro-1,2,4-triazine-3-one, the title compound is synthesized in otherwise a similar manner as Example 68.

EXAMPLE 93

2-[3,5-dichloro-4-(4'-chloro-1-chloromethylbenzyl)phenyl]-2,3,4,5-tetrahydro-1,2,4-triazin-3-one (compound No. 101)

In toluene, 2-[3,5-dichloro-4-(4'-chloro-1-hydroxymethylbenzyl)phenyl]-2,3,4,5-tetrahydro-1,2,4-triazin-3-one is heated with thionylchloride and purified to give the title compound by a column chromatography.

EXAMPLE 94

2-[3,5-dichloro-4-(4'-chloro-1-methylbenzyl)phenyl]-2,3,4,5-tetrahydro-1,2,4-triazin-3-one (compound No. 102)

2-[3,5-dichloro-4-(4'-chloro-1-chloromethylbenzyl)phenyl]-2,3,4,5-tetrahydro-1,2,4-triazin-3-one is dissolved in acetic acid and refluxed with 5-fold molar zinc-powder for 3 hours. After concentrated, iced water is added to the results and extracted with ethyl acetate. The extract is dried by $MgSO_4$ and concentrated and purified by a column chromatography to provide the title compound.

EXAMPLE 95

2-[3,5-dichloro-4-(4'-chloro-1-methoxymethylbenzyl)phenyl]-2,3,4,5-tetrahydro-1,2,4-triazin-3-one (compound No. 103)

In methanol, 2-[3,5-dichloro-4-(4'-chloro-1-chloromethylbenzyl)phenyl]-2,3,4,5-tetrahydro-1,2,4-triazin-3-one is reacted with sodium methoxide to provide the title compound.

EXAMPLE 96

2-[3-trifluoromethyl-4-(4'-chloro-1-methylbenzyl)phenyl]-2,3,4,5-tetrahydro-1,2,4-triazin-3-one (compound No. 104)

In acetic acid is dissolved 2-[3-trifluoromethyl-4-(4'-chloro-1-methylbenzyl)phenyl]-2,3,4,5-tetrahydro-1,2,4-triazin-3-one followed by addition of 5-fold molar Zinc powder and refluxed for 3 hours with heated. After adding ice water, the reaction solution is extracted with ethyl acetate. The extract is dried with $MgSO_4$, concentrated and subjected to purification by column chromatography to provide the title compound.

EXAMPLE 97

2-{4-[2-(4-chlorophenyl)-1-cyanovinyl]-3,5-dichlorophenyl}-4,5-dihydro-1,2,4-triazin-3(2H)-one (compound No. 87)

Starting with 4-[2-(4-chlorophenyl)-1-cyanovinyl]-3,5-dichlorophenylhydrazine, the title compound was synthesized in otherwise a similar manner as Example 47. m.p. 83–85° C.

H-NMR (CDCl$_3$) δ; 4.12–4.17(2H,J=2.1 Hz,t), 5.83–5.86 (1H,J=2.5 Hz,d), 7.07–7.89(8H,m).

EXAMPLE 98

2-[3,5-dichloro-4-(5-trifluoromethyl-1,2,4-oxadiazol-3-yl-methyl)phenyl]-4,5-dihydro-1,2,4-triazin-3(2H)-one (compound No. 86)

Staring with 3,5-dichloro-4-(5-trifluoromethyl-1,2,4-oxadiazol-3-yl-methyl)phenylhydrazine, the title compound was synthesized in otherwise a similar manner as Example 47. m.p 164–165° C.

EXAMPLE 99

2-[4-(4-chloro-α-chloromethylbenzyl)- 3-trifluoromethylphenyl]-4,5-dihydro-1,2,4-triazin-3(2H)-one (compound No.76)

Staring with Compound No.95, the title compound was synthesized in otherwise a similar manner as Example 68. m.p. 157–158° C.

EXAMPLE 100

2-[3-chloro-4-(4-chloro-α-fluorobenzyl)-5-methylpheyl]-4,5-dihydro-1,2,4-triazin-3(2H)-one (compound No.78)

Staring with Compound No.79, the title compound was synthesized in otherwise a similar manner as Example 68. m.p. 141–142° C. (dec.).

EXAMPLE 101

2-[3-chloro-4-(4-chloro-α-hydroxybenzyl)-5-methylpheyl]-1,4,5,6-tetrahydro-1,2,4-triazin-3(2H)-one (compound No.80)

Staring with Compound No.81, Compound No.79 was synthesized in otherwise a similar manner as Example 60, followed by additon of excess sodium borate to synthsize compound No. 80. m.p. 146–147° C.

EXAMPLE 102

2-[3-chloro-4-(4-chlorobenzoyl)-5-methylpheyl]-4,5-dihydro-1,2,4-triazin-3(2H)-one (compound No.81)

Starting with 3-chloro-4-(4-chlorobenzoyl)-5-methylpheylhydrazine, the title compound was synthesized in otherwise a similar manner as Example 47. m.p. 171–172° C.

EXAMPLE 103

2-[(3-chloro-4-(4-chlorobenzoyl)-5-methylpheyl]-1,2,4-triazin-3(2H)-one-5(4H)-thione (compound No.82)

Starting with 2-[3-chloro-4-(4-chlorobenzoyl)-5-methylpheyl]-1,2,4-triazin-3,5(2H,4H)-dione, the title compound was synthesized in otherwise a similar manner as Example 5. m.p. 104–106° C.

H'-NMR[d6-DMSO] δ; 2.16(3H, s), 7.60–7.89 (7H, m), 13.89(1H, br-s).

EXAMPLE 104

2-[(3-chloro-5-methyl-4-phenyl)phenyl]-4,5-dihydro-1,2,4-triazin-3(2H)-one (compound No. 83)

Starting with (3-chloro-5-methyl-4-phenyl) phenylhydrazine, the title compound was synthesized in otherwise a similar manner as Example 47. m.p. 175–176° C.

TABLE 3

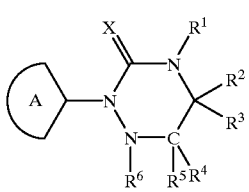

| Compound No. | A | X | $\underset{R^3}{\overset{R^1\ \ R^2}{-N-C-}}$ | $\underset{R^6\ \ R^4}{\overset{R^5}{-N-C-}}$ |
|---|---|---|---|---|
| 1 | 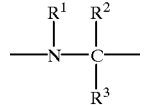 | O | —NH—CH$_2$— | —N=CH— |

TABLE 3-continued

| Compound No. | A— | X | R¹ R² \ \| —N—C— \| R³ | R⁵ \ \| —N—C— \| R⁶ R⁴ |
|---|---|---|---|---|
| 2 | 3,5-dichlorophenyl | O | —NH—C(Me)(Me)— | —N=CH— |
| 3 | 3,5-dichlorophenyl | O | —NH—CH(SMe)— | —N=CH— |
| 4 | 3,5-dichlorophenyl | O | —NH—C(SMe)(SMe)— | —NH—CH₂— |
| 5 | 3,5-dichlorophenyl | O | —NH—CH₂— | —NH—CH₂— |
| 6 | 3,5-dichlorophenyl | O | —NH—CH₂— | —N=C(Me)— |
| 7 | 3,5-dichlorophenyl | O | —NH—C(=S)— | —N=CH— |

TABLE 3-continued
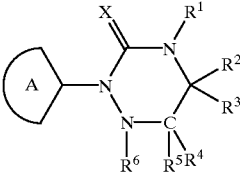
| Compound No. | A— | X | R¹ R² \\ / —N—C— / \\ R³ | R⁵ \\ —N—C— / \\ R⁶ R⁴ |
|---|---|---|---|---|
| 8 | 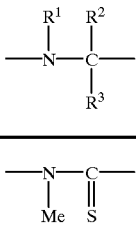 3,5-di-Cl-phenyl | O | —N(Me)—C(=S)— | —NH—CH₂— |
| 9 | 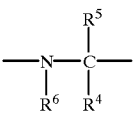 3,5-di-Cl-phenyl | O | —NH—C(=S)— | —NH—CH₂— |
| 10 | 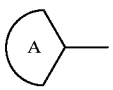 3,5-di-Cl-phenyl | O | —NH—CH(Ph)— | —NH—CH₂— |
| 11 | 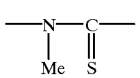 3,5-di-Cl-phenyl | O | —NH—CH(Ph)— | —N=CH— |
| 12 | 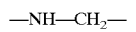 3,5-di-Cl-phenyl | O | —N(Me)—CH₂— | —NH—CH₂— |
| 13 | 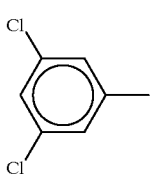 3,5-di-Cl-phenyl | O | —NH—CH₂— | —NH—CH(Me)— |

TABLE 3-continued

| Compound No. | A | X | $\overset{R^1}{\underset{R^3}{\overset{|}{\underset{|}{N}}\!\!=\!\!\overset{R^2}{\underset{|}{C}}}}$ | $\overset{R^5}{\underset{R^6\ R^4}{\overset{|}{\underset{|}{N}}\!\!-\!\!\overset{|}{\underset{|}{C}}}}$ |
|---|---|---|---|---|
| 14 | 3,5-diCl-C₆H₃ | O | —N=C(SMe)— | —N=CH— |
| 15 | 3,5-diCl-C₆H₃ | O | —N=C(SCH₂Ph)— | —N=CH— |
| 16 | 3,5-diCl-C₆H₃ | O | —N=C(OMe)— | —N=CH— |
| 17 | 3,5-diCl-C₆H₃ | O | —N=C(Cl)— | —N=CH— |
| 18 | 3,5-diCl-C₆H₃ | O | —N=C(F)— | —N=CH— |
| 19 | 3,5-diCl-C₆H₃ | O | —N=C(S-4-Cl-C₆H₄)— | —N=CH— |

TABLE 3-continued
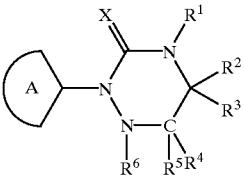
| Compound No. | A— | X | (R¹,R²,R³ group) | (R⁵,R⁶,R⁴ group) |
|---|---|---|---|---|
| 20 | 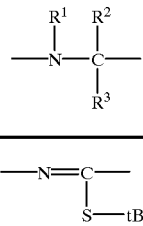 | O | 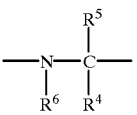 | —N=CH— |
| 21 | 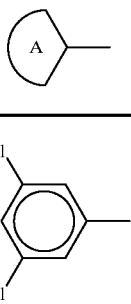 | O | 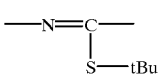 | —N=CH— |
| 22 |  | O | 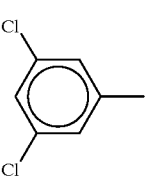 | —N=CH— |
| 23 | 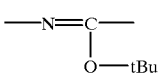 | O |  | —N=CH— |
| 24 | 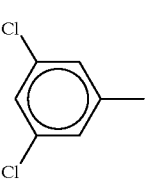 | O | 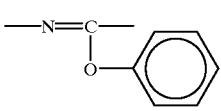 | —N=CH— |
| 25 |  | O | 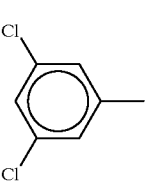 | —N=CH— |

TABLE 3-continued
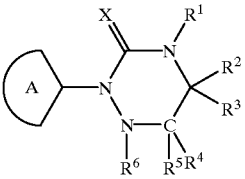
| Compound No. | A— | X | —N(R¹)—C(R²)(R³)— | —N(R⁶)—C(R⁵)(R⁴)— |
|---|---|---|---|---|
| 26 | 3,5-dichlorophenyl | O | —N=C(S(CH₂)₃SH)— | —N=CH— |
| 27 | 3,5-dichlorophenyl | O | —N=C(Ph)— | —N=CH— |
| 28 | 3,5-dichlorophenyl | O | —N=C(Ph)— | —N=C(Ph)— |
| 29 | 3,5-dichlorophenyl | O | —N=C(SMe)— | —NH—CH₂— |
| 30 | phenyl | O | —NH—C(=S)— | —N=CH— |
| 31 | phenyl | O | —N=C(SMe)— | —N=CH— |
| 32 | phenyl | O | —N=C(OMe)— | —N=CH— |
| 33 | 4-chlorophenyl | O | —NH—C(=S)— | —N=CH— |

TABLE 3-continued
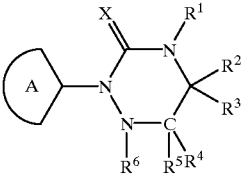
| Compound No. | A– | X | –N(R¹)–C(R²)(R³)– | –N(R⁶)–C(R⁵)(R⁴)– |
|---|---|---|---|---|
| 34 | 4-Cl-C₆H₄– | O | –N=C(SMe)– | –N=CH– |
| 35 | 4-Cl-C₆H₄– | O | –N=C(OMe)– | –N=CH– |
| 36 | 4-Cl-C₆H₄–CH(CN)–(2,6-Cl₂-C₆H₂)– | O | –NH–C(=S)– | –N=CH– |
| 37 | 4-Cl-C₆H₄–CH(CN)–(2,6-Cl₂-C₆H₂)– | O | –NH–C(=S)– | –NH–CH₂– |
| 38 | 4-Cl-C₆H₄–CH(CN)–(2,6-Cl₂-C₆H₂)– | O | –NH–CH₂– | –NH–CH₂– |
| 39 | 4-Cl-C₆H₄–CH(CN)–(2,6-Cl₂-C₆H₂)– | O | –NH–CH₂– | –N=C(Me)– |
| 40 | 4-Cl-C₆H₄–CH(CN)–(2,6-Cl₂-C₆H₂)– | O | –N(Me)–CH₂– | –NH–CH₂– |

TABLE 3-continued
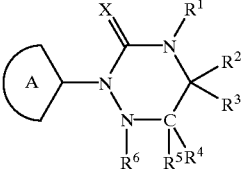
| Compound No. | A— | X | —N(R¹)—C(R²)(R³)— | —N(R⁵)—C(R⁴)(R⁶)— |
|---|---|---|---|---|
| 41 | 4-Cl-C₆H₄-CH(CN)-(2,6-Cl₂-4-Me-C₆H₂)- | O | —NH—CH₂— | —N=CH— |
| 42 | 4-Cl-C₆H₄-CH(CN)-(2,6-Cl₂-4-Me-C₆H₂)- | O | —N=C(OMe)— | —N=CH— |
| 43 | 4-Cl-C₆H₄-CH(CN)-(2,6-Cl₂-4-Me-C₆H₂)- | O | —N=C(SMe)— | —N=CH— |
| 44 | 4-Cl-C₆H₄-CH(CN)-(2,6-Cl₂-4-Me-C₆H₂)- | O | —N=C(Cl)— | —N=CH— |
| 45 | 4-Cl-C₆H₄-S-(2,6-Cl₂-4-Me-C₆H₂)- | O | —NH—CH₂— | —N=C(Me)— |
| 46 | 4-Cl-C₆H₄-C(O)-(2,6-Cl₂-4-Me-C₆H₂)- | O | —NH—CH₂— | —N=C(Me)— |

TABLE 3-continued
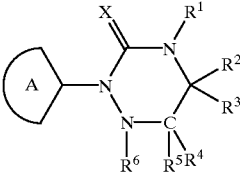
| Compound No. | A- | X | R¹R²<br>−N−C−R³ | R⁵<br>−N−C−R⁴<br>R⁶ |
|---|---|---|---|---|
| 47 | 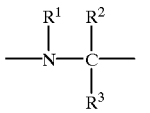 | O | −N−CH₂−<br>COCH₃ | −N=C−<br>Me |
| 48 | 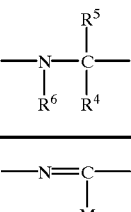 | O | −NH−CH₂− | −N−CH₂−<br>Me |
| 49 | 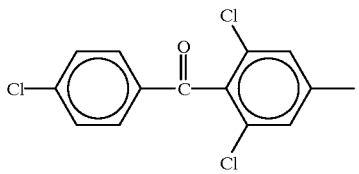 | S | −NH−CH₂− | −N=CH−<br>Cl |
| 50 | 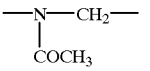 | O | −NH−CH−<br>Me | −N−CH₂−<br>Me |
| 51 | 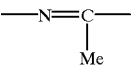 | S | −NH−CH₂− | −N−CH₂−<br>Me |
| 52 | 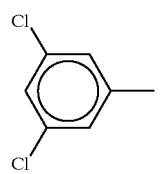 | O | −NH−CH₂− | −N=CH− |

TABLE 3-continued

| Compound No. | A— | X | —N(R¹)—C(R²)(R³)— | —N(R⁶)—C(R⁵)(R⁴)— |
|---|---|---|---|---|
| 53 | 4-Cl-C₆H₄-CH(CN)-[2-Cl,4-Me,6-Me-C₆H₂]- | O | —NH—CH₂— | —NH—CH₂— |
| 54 | 4-Cl-C₆H₄-CH(CN)-[2-Cl,4-Me,6-Me-C₆H₂]- | O | —NH—C(=S)— | —N=CH— |
| 55 | 4-Cl-C₆H₄-CH(CN)-[2-Cl,4-Me,6-Me-C₆H₂]- | O | —NH—C(=S)— | —NH—CH₂— |
| 56 | 4-Cl-C₆H₄-CO-[2,6-Cl₂,4-Me-C₆H₂]- | O | —NH—CH₂— | —N=CH— |
| 57 | 4-Cl-C₆H₄-CH(OH)-[2,6-Cl₂,4-Me-C₆H₂]- | O | —NH—CH₂— | —N=CH— |
| 58 | 4-Cl-C₆H₄-CO-[2-Cl,4-Me-C₆H₃]- | O | —NH—CH₂— | —N=CH— |
| 59 | 4-Cl-C₆H₄-CH(OH)-[2-Cl,4-Me-C₆H₃]- | O | —NH—CH₂— | —N=CH— |

TABLE 3-continued
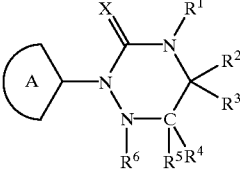
| Compound No. | A | X | $-N\overset{R^1}{\underset{R^3}{-}}\overset{R^2}{\underset{}{C-}}$ | $-N\overset{R^5}{\underset{R^4}{-}}\overset{}{\underset{}{C-}}$ |
|---|---|---|---|---|
| 60 | 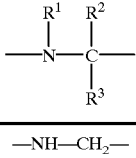 | O | —NH—CH$_2$— | —N=CH— |
| 61 | 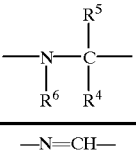 | O | —NH—CH$_2$— | —N=CH— |
| 62 | 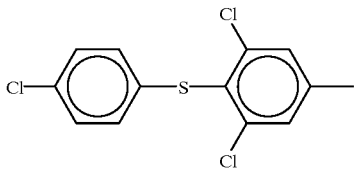 | O | —NH—CH$_2$— | —N=CH— |
| 63 | 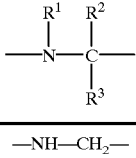 | O | —NH—CH$_2$— | —N=CH— |
| 64 | 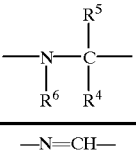 | O | —NH—CH$_2$— | —N=CH— |
| 65 | 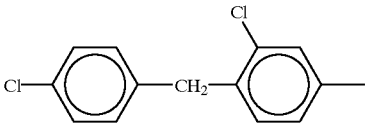 | O | —NH—CH$_2$— | —N=CH— |
| 66 | 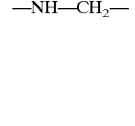 | O | —NH—CH$_2$— | —N=CH— |

TABLE 3-continued
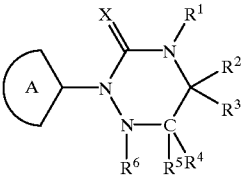
| Compound No. | A | X | $\overset{R^1}{-}N-\overset{R^2}{\underset{R^3}{C}}-$ | $\overset{}{-}N-\overset{R^5}{\underset{R^6\ R^4}{C}}-$ |
|---|---|---|---|---|
| 67 | 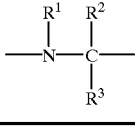 | O | —NH—CH$_2$— | —N=CH— |
| 68 | 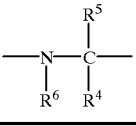 | O | —NH—CH$_2$— | —NH—CH$_2$— |
| 69 |  | O | —NH—CH$_2$— | —NH—CH$_2$— |
| 70 | 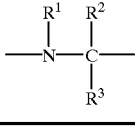 | O | —NH—CH$_2$— | —N=CH— |
| 71 | 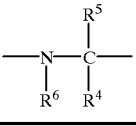 | O | —NH—CH$_2$— | —NH—CH$_2$— |
| 72 | 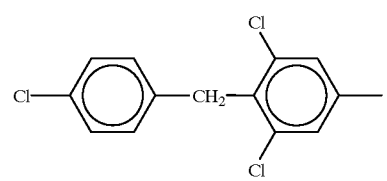 | O | —NH—CH$_2$— | —N=CH— |
| 73 | 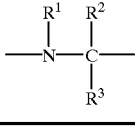 | O | —NH—CH$_2$— | —N=CH— |

TABLE 3-continued
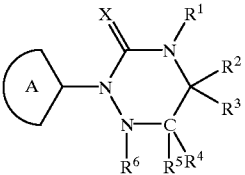
| Compound No. | A— | X | —NR¹—CR²R³— | —NR⁶—CR⁵R⁴— |
|---|---|---|---|---|
| 74 |  | O | —NH—CH₂— | —N=CH— |
| 75 | 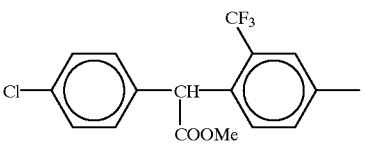 | O | —NH—CH₂— | —N=CH— |
| 76 |  | O | —NH—CH₂— | —N=CH— |
| 77 | 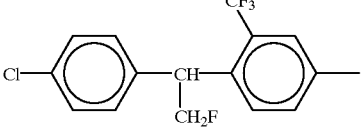 | O | —NH—CH₂— | —NH—CH₂— |
| 78 |  | O | —NH—CH₂— | —N=CH— |
| 79 | 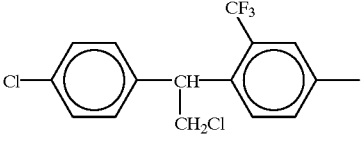 | O | —NH—CH₂— | —N=CH— |
| 80 |  | O | —NH—CH₂— | —NH—CH₂— |

TABLE 3-continued
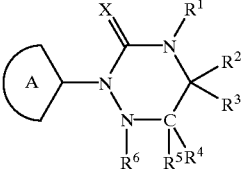
| Compound No. | A— | X | —N(R¹)—C(R²)(R³)— | —N(R⁶)—C(R⁵)(R⁴)— |
|---|---|---|---|---|
| 81 | 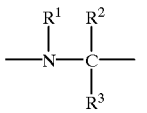 | O | —NH—CH₂— | —N=CH— |
| 82 | 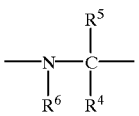 | O | —NH—C(=S)— | —N=CH— |
| 83 | 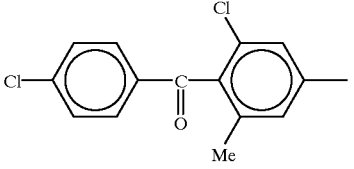 | O | —NH—CH₂— | —N=CH— |
| 84 | 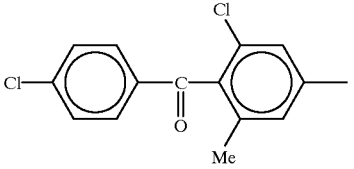 | O | —NH—CH₂— | —N=CH— |
| 85 | 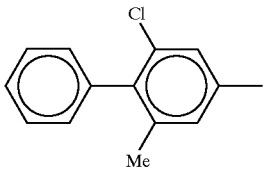 | O | —NH—CH₂— | —N=CH— |
| 86 | 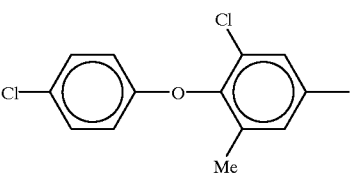 | O | —NH—CH₂— | —N=CH— |

TABLE 3-continued
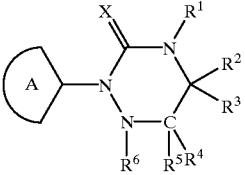
| Compound No. | A | X | —N(R¹)—C(R²)(R³)— | —N(R⁶)—C(R⁵)(R⁴)— |
|---|---|---|---|---|
| 87 | 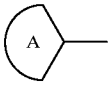 | O | —NH—CH₂— | —N=CH— |
| 88 | 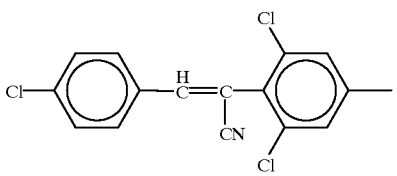 | O | —NH—CH₂— | —NH—CH₂— |
| 89 | 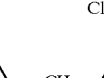 | O | —NH—CH₂— | —N=CH— |
| 90 | 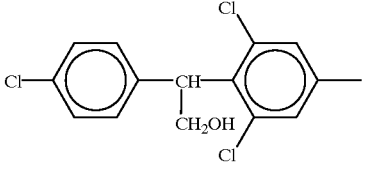 | O | —NH—CH₂— | —NH—CH₂— |
| 91 |  | O | —NH—CH₂— | —NH—CH₂ |
| 92 | 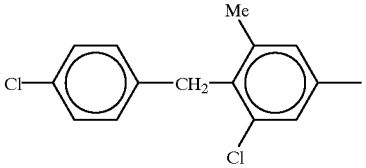 | O | —NH—CH₂— | —NH—CH₂— |

TABLE 3-continued
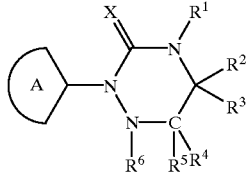
| Compound No. | A— | X | —N(R¹)C(R²)(R³)— | —N(R⁵R⁶)C(R⁴)— |
|---|---|---|---|---|
| 93 |  | O | —NH—CH₂— | —NH—CH₂— |
| 94 | 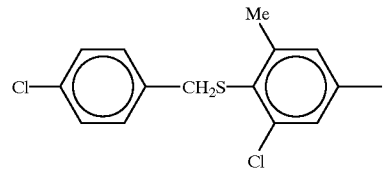 | O | —NH—CH₂— | —N=CH— |
| 95 |  | O | —NH—CH₂— | —N=CH— |
| 96 | 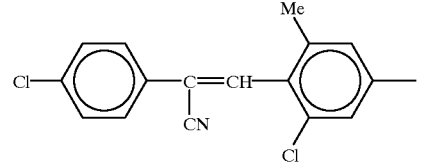 | O | —NH—CH₂— | —N=CH— |
| 97 |  | O | —NH—CH₂— | —N=CH— |
| 98 | 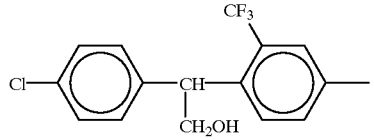 | O | —NH—CH₂— | —N=CH— |

TABLE 3-continued

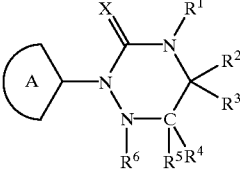

| Compound No. | A— 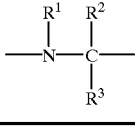 | X | $-\overset{R^1}{\underset{}{N}}-\overset{R^2}{\underset{R^3}{C}}-$ | $-\overset{}{\underset{R^6}{N}}-\overset{R^5}{\underset{R^4}{C}}-$ |
|---|---|---|---|---|
| 99 | 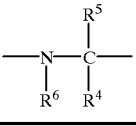 | O | —NH—CH$_2$— | —N=CH— |
| 100 | 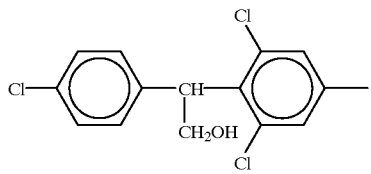 | O | —NH—CH$_2$— | —N=CH— |
| 101 | 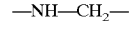 | O | —NH—CH$_2$— | —N=CH— |
| 102 | 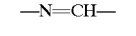 | O | —NH—CH$_2$— | —N=CH— |
| 103 | 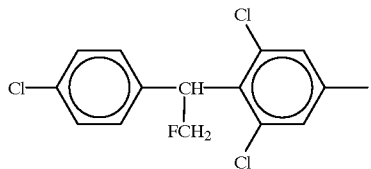 | O | —NH—CH$_2$— | —N=CH— |
| 104 | 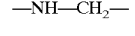 | O | —NH—CH$_2$— | —N=CH— |

FORMULATION EXAMPLE 1

2-(3,5-Dichlorophenyl)-5-methoxy-2,3-dihydro-1,2,4-triazin-3-one (Compound No. 18), 25 g, was pulverized to pass a 355 μm sieve thoroughly and evenly blended with 975 g of defatted rice bran (1:1);

FORMULATION EXAMPLE 1

2-(3,5-Dichlorophenyl)-2,3,4,5-tetrahydro-1,2,4-triazin-3-one (Compound No. 1), 5.0 g, was dissolved in 10 cc of methanol, followed by addition of 100 g of soybean. After stirring, the mixture was dried in vacuo at 50° C. for 10 hours. This mixture was crushed to pass a 500 μm sieve thoroughly and blended uniformly with 895 g of soybean meal to provide a composition.

The substituent designations of the formulae of the second embodiment are specific to the second embodiment and may be the same or different than the substituent designation according to the first embodiment.

BACKGROUND OF THE SECOND EMBODIMENT

1. Field of the Second Embodiment

This second embodiment relates to a novel method of producing triazine derivatives, and also relates to a novel semicarbazone derivative which can be employed in the method of this second embodiment. This second embodiment also relates to a novel triazine derivative.

2. Description of the Prior Art

A 1,2,4-triazine derivative having a substituent at the 2-position has been widely used as an agent for controlling pests in the fields of medicines, veterinary drugs and agricultural drugs. For example, as veterinary drugs, a report is found in JPA H2(1990)-240003 that the compound is employable for controlling parasitic worms in fish and insects, and, another report is found in JPA H5(1993)-1047 that the compound is effective for controlling parasitic protozoa, especially coccidia. And, as agricultural chemicals, the effectiveness of the compound as a herbicide is reported in WO-A-86/0072 (Jan. 3, 1986; FMC Co.).

As described thus above, 1,2,4-triazine derivatives having a substituent at 2-position, especially -3,5-dione derivatives and -3-one derivatives, are remarkably useful compounds for controlling pests. The present inventors considered that finding of a method of producing these compounds simply and conveniently would make a contribution to social welfare, and started the present research work.

As methods of synthesizing a 1,2,4-triazine-3,5-dione derivative having a substituent at the 2-position, a method which comprises allowing a hydrazone derivative to react with a keto-carboxylic acid [WO-A-86/00072] and a method which comprises allowing an active methylene compound (e.g. cyanoacetylurethane) to react with diazonium salt then subjecting the reaction mixture to ring-closure, decarboxylation reaction to produce the object compound [Journal of Medicinal Chemistry, Vol.22, p.1483, 1977] have been known. These methods, however, are-accompanied with such drawbacks as having a relatively large number of reaction steps and requiring relatively drastic reaction conditions, thus being difficult to conduct on an industrial scale.

Especially no practical method of producing a 1,2,4-triazin-3-one derivative having a substituent at the 2-position has been known.

SUMMARY OF THE SECOND EMBODIMENT

The second embodiment is to provide a method of producing simply and conveniently triazine derivatives in a high yield which can be used as medicines, veterinary drugs and agricultural chemicals. Another object of the second embodiment is to provide novel semicarbazone derivatives (II) and hydrazone derivatives (I) which can be used in the production of the triazine derivatives. Yet another object of the second embodiment is to produce novel 1,2,4-triazin-3-one derivatives which can be used as described above.

In view of the above-described technical background, the present inventors conducted extensively various studies for establishing a method of producing, for example, a 2-substituted-1,2,4-triazin-3-one derivative in which the 5-position of the triazine ring is unsubstituted. As a result, we found that a 2-substituted-1,2,4-triazine-3,5-dione derivative can be produced in a high yield by allowing a hydrazone derivative represented by the general formula (I) as defined hereinafter to react with 2,2-dialkoxyethyl isocyanate in the presence of a base, to produce a reaction mixture which contains a semicarbazone derivative. The reaction mixture is then subjected to ring-closure reaction to produce a 2-substituted-1,2,4-triazin-3-one derivative (III), followed by subjecting thus-produced 2-substituted-1,2,4-triazine-3-one derivative to oxidation to produce a 2-substituted-1,2,4-triazine-3,5-dione derivative. They have conducted further studies diligently to accomplish the second embodiment.

DETAILED DESCRIPTION OF THE SECOND EMBODIMENT

More specifically, the second embodiment is to provide a semicarbazone derivative (II) represented by the formula:

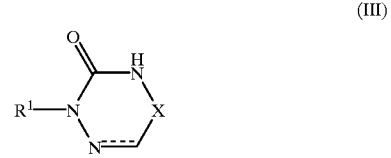

(II)

wherein $R^1$ stands for an optionally substituted hydrocarbon residual group; $R^2$ and $R^3$ independently stand for hydrogen, an optionally substituted hydrocarbon residual group or an electron withdrawing group; and $R^4$ stands for an optionally substituted alkyl group, and, a method of producing a 1,2,4-triazin-3-one derivative (III) represented by the formula

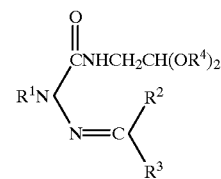

(III)

wherein $R^1$ is of the same meaning as defined above; X stands for carbonyl group, thiocarbonyi group, an optionally substituted methylene group; and dashed line means that a double bond may optionally be formed, which is characterized by subjecting the said semicarbazone derivative (II) to ring-closure reaction.

In the above-mentioned formulae, as the optionally substituted hydrocarbon residual groups shown by $R^1$, mention is made of, for example, an aromatic ring, more specifically, an optionally substituted aromatic homocyclic group and a 5- to 6-membered aromatic heterocyclic group optionally having at least one substituent.

Examples of the optionally substituted aromatic homocyclic group include $C_{6-14}$ aryl groups such as phenyl, 1- or 2-naphthyl. Among them, preferable one is a phenyl group., Particularly preferable examples are a phenyl substituted at 3- and 4-positions and a phenyl substituted at 3-, 4- and 5-positions.

Examples of the 5- to 6-membered aromatic heterocyclic groups include-an unsaturated 5- to 6-membered cyclic group containing, besides carbon atoms, 1 to 4 hetero-atoms such as oxygen atom, sulfur atom and nitrogen atom, such as a 5-membered cyclic group containing, besides carbon atoms, 1 to 4 hetero-atoms selected from oxygen atom, sulfur atom and nitrogen atom, e.g. 2- or 3-thienyl, 2- or 3-furyl, 2- or 3-pyrrolyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl and 1H- or 2H-tetrazolyl, and, a 6-membered cyclic group containing, besides carbon atoms, 1 to 4 hetero-atoms selected from oxygen atom, sulfur atom and nitrogen atom, e.g. 2-, 3- or 4-pyridyl, N-oxido-2, 3- or 4-pyridyl, 2-, 4- or 5-pyrimidinyl, N-oxido-2-, 4- or 5-pyrimidinyl, dioxotriazinyl, pyranyl, thiopyranyl, 1,3-oxazinyl, 1,4-thiazinyl, 1,3-thiazinyl, triazinyl, oxotriazinyl, 3- or 4-pyridazinyl, pyrazinyl and N-oxido-3- or 4-pyridazinyl. Among them, a 6-membered ring containing one hetero-atom is preferable, and a N-containing hetero-ring, for example, is especially preferable.

Such aromatic homocyclic or heterocyclic groups as above may optionally have, at any possible position, 1 to 5, preferably 1 to 3 substituents selected from, for example, (1) $C_{1-4}$ alkyl groups such as methyl, ethyl, propyl, isopropyl, butyl, isobutyl, sec-butyl and tert-butyl, (2) $C_{2-4}$ alkenyl groups such as vinyl, 1-methylvinyl, 1-propenyl and allyl, (3) $C_{7-11}$ aralkyl groups such as benzyl, α-methylbenzyl, α-cyanobenzyl, α-hydroxybenzyl and phenethyl, (4) phenyl group, (5) $C_{1-6}$ alkoxy groups such as methoxy, ethoxy, propoxy, iso-propoxy, n-butoxy, iso-butoxy, sec-butoxy and tert-butoxy group, (6) phenoxy group, (7) $C_{1-6}$ alkanoyl groups such as formyl, acetyl, propionyl, n-butyryl and iso-butyryl group, (8) benzoyl group, (9) carboxyl group,

(10) $C_{2-7}$ alkoxycarbonyl groups such as methoxycarbonyl, ethoxycarbonyl, n-propoxycarbonyl, iso-propoxycarbonyl, n-butoxycarbonyl, isobutoxycarbonyl and tert-butoxycarbonyl group,

(11) carbamoyl group,

(12) N-mono-$C_{1-4}$ alkylcarbamoyl groups such as N-methylcarbamoyl, N-ethylcarbamoyl, N-propylcarbamoyl, N-isopropylcarbamoyl and N-butylcarbamoyl,

(13) N,N-di-$C_{1-4}$ alkylcarbamoyl groups such as N,N-dimethylcarbamoyl, N,N-diethylcarbamoyl, N,N-dipropylcarbamoyl and N,N-dibutylcarbamoyl,

(14) halogen atoms such as fluorine, chlorine, bromine and iodine,

(15) mono-, di- or tri-halogeno-$C_{1-4}$ alkyl groups such as chloromethyl dichloromethyl, trifluoromethyl and trifluoroethyl,

(16) optionally protected amino groups,

(17) mono-$C_{1-4}$ alkylamino groups such as methylamino, ethylamino, propylamino, isopropylamino and butylamino,

(18) $C_{1-6}$ alkanoylamino groups such as formamido, acetamino, trifluoroacetamido, propionamido, butylamido and isobutylamido,

(19) benzoylamino groups such as benzamido,

(20) carbamoylamino group,

(21) N—$C_{1-4}$ alkyl carbamoylamino groups such as N-methyl carbamoylamino, N-ethyl carbamoylamino, N-propyl carbamoylamino, N-isopropyl carbamoylamino and N-butyl carbamoylamino,

(22) N,N-di-$C_{1-4}$ alkyl carbamoylamino groups such as N,N-dimethyl carbamoylamino, N,N-diethyl carbamoylamino, N,N-dipropyl carbamoylamino and N,N-dibutyl carbamoylamino,

(23) $C_{1-3}$ alkylenedioxy groups such as methylenedioxy and ethylenedioxy group,

(24) hydroxy group,

(25) nitro group,

(26) cyano group,

(27) mercapto group,

(28) sulfo group,

(29) sulfino group,

(30) phosphono group,

(31) sulfamoyl group,

(32) $C_{1-6}$ monoalkyl sulfamoyl groups such as N-methyl sulfamoyl, N-ethyl sulfamoyl, N-propyl sulfamoyl, N-isopropyl sulfamoyl and N-butyl sulfamoyl,

(33) di-$C_{1-4}$ alkyl sulfamoyl groups such as N,N-dimethyl sulfamoyl, N,N-diethyl sulfamoyl, N,N-dipropyl sulfamoyl and N,N-dibutyl sulfamoyl,

(34) $C_{1-6}$ alkylthio groups such as methylthio, ethylthio, propylthio, isopropylthio, n-butylthio, sec-butylthio and tert-butylthio group,

(35) phenylthio group,

(36) $C_{1-6}$ alkyl sulfinyl groups such as methyl sulfinyl, ethyl sulfinyl, propyl sulfinyl and butyl sulfinyl,

(37) phenyl sulfinyl group,

(38) $C_{1-6}$ alkyl sulfonyl groups such as methyl sulfonyl, ethyl sulfonyl, propyl sulfonyl and butyl sulfonyl group,

(39) phenyl sulfonyl group, and

(40) a 5- or 6-membered heterocyclic group containing, besides carbon atoms, 1 to 4 hetero-atoms selected from oxygen atom, sulfur atom and nitrogen atom, which may optionally be linked to the above-mentioned aromatic cyclic group through 1 to 4 carbon atoms, oxygen atoms, nitrogen atoms and atomic chain consisting of, for example, oxygen atom, such as 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4-pyridyl, 2-, 4- or 5-pyrimidinyl, N-oxido-2-, 4- or 5-pyrimidinyl, oxoimidazinyl, dioxotriazinyl, pyranyl, thiopyranyl, 1,4-oxazinyl, 1,4-thiazinyl, 1,3-thiazinyl, triazinyl, oxotriazinyl, 3- or 4-pyridazinyl, pyrazinyl and N-oxido-3- or 4-pyridazinyl.

Among the above-mentioned hydrocarbon residual groups shown by $R^1$, optionally substituted phenyl groups are preferable. Especially preferable examples of such substituents include an optionally substituted $C_{7-11}$ aralkyl groups (3) and/or halogen atom (14). The phenyl having substituents at 3- or/and 5-positions and 4-position, and the phenyl having substituents at 3- and/or 5-position and 4-position are especially preferable.

Among these groups, those having carbon chain or cyclic group containing two or more carbon atoms may optionally have, at any possible position, further one to four, preferably one or two substituents selected from, for example,
  (a) halogen atoms such as chlorine, fluorine, bromine and iodine,
  (b) hydroxy group,
  (c) $C_{1-4}$ alkoxy groups such as methoxy and ethoxy, or oxo group,
  (d) di-$C_{1-4}$ alkylamino groups such as dimethylamino and diethylamino,
  (e) halogeno-$C_{1-4}$ alkyl groups such as chloromethyl, 1-chloroethyl, 1-fluoroethyl, fluoromethyl, trifluoromethyl and trifluoroethyl,
  (f) $C_{1-7}$ acyl groups such as formyl, acetyl, propionyl, isopropionyl, trifluoroacetyl and benzoyl,
  (g) hydroxy-$C_{1-4}$ alkyl groups such as hydroxymethyl, 1-hydroxyethyl and 2-hydroxyethyl,
  (h) $C_{1-4}$ alkoxy-$C_{1-4}$ alkyl groups such as methoxymethyl, 1-methoxyethyl, 1-ethoxyethyl, acetoxyethyl and 2-ethoxyethyl,
  (i) $C_{1-5}$ sulfamoyl groups such as aminosulfonyl, methylaminosulfonyl, dimethylaminosulfonyl and morpholynosulfonyl,
  (j) $C_{1-7}$ carbamoyl group such as aminocarbonyl, methylaminocarbonyl, dimethylaminocarbonyl and phenylaminocarbonyl
  (k) $C_{2-4}$ alkyl groups such as ethyl and isopropyl,
  (l) carboxyl group,
  (m) $C_{1-7}$ alkoxycarbonyl group such as methoxycarbonyl, ethoxycarbonyl and phenoxycarbonyl.

For example, in the case that the $C_{7-11}$ aralkyl group (3) is benzyl, the benzyl substituted at its 4-position with the substituent (f) or (g) is preferable.

In the above formulae, as the optionally substituted hydrocarbon residual groups shown by $R^2$ or $R^3$, mention is made of, for example, optionally substituted alkyl groups and optionally substituted aromatic homocyclic groups or 5- to 6-membered aromatic heterocyclic groups.

Among them, as the alkyl group, use is preferably made of $C_{1-4}$ lower alkyl groups (e.g. methyl), as the aromatic homocyclic group, use is preferably made of phenyl group, and, as the aromatic heterocyclic groups, use is preferably made of 2-, 3- or 4-pyridyl group.

Examples of the electron withdrawing groups shown by $R^2$ or $R^3$ include cyano group, $C_{1-6}$ alkoxy-carbonyl such as methoxy carbonyl and ethoxy carbonyl, hydroxy carbonyl, $C_{6-10}$ aryloxy carbonyl groups such as phenyloxy carbonyl and naphthyloxy carbonyl, a 5- or 6-membered heterocyclic-oxycarbonyl group containing, besides carbon atoms, 1 to 4 hetero-atoms selected from nitrogen atom, sulfur atom and oxygen atom, such as pyridyloxy carbonyl and thienyloxy carbonyl, $C_{1-6}$ alkyl sulfonyl groups optionally substituted with one to three halogen atoms selected from, for example, chlorine, bromine and fluorine, such as methyl sulfonyl, trifluoromethyl sulfonyl and ethyl sulfonyl, amino sulfonyl, di-$C_{1-4}$ alkoxy phosphoryl groups such as dimethoxyphosphoryl, diethoxyphosphoryl and dipropoxyphosphoryl, $C_{1-6}$ acyl groups optionally substituted with one to three halogen atoms selected from chlorine, bromine and fluorine, such as acetyl and propionyl, carbamoyl, and $C_{1-6}$ alkyl-sulfonyl thiocarbamoyl groups such as methyl sulfonyl thiocarbamoyl and ethyl sulfonyl thiocarbamoyl group.

As the preferable example of $R^2$ and $R^3$, mention is made of hydrogen as one of $R^2$ and $R^3$ and phenyl as the other.

Further, $R^2$ and $R^3$ may optionally be combined with each other to form a 4- to 7-membered ring such as preferably cycloalkyl groups. Other 4- to 7-membered rings such as optionally substituted aryl, arylalkyl, homocyclic and heterocyclic rings are also contemplated by the present invention.

Examples of the optionally substituted alkyl groups shown by $R^4$ include $C_{1-4}$ alkyl groups, and especially methyl and ethyl are preferable. One $R^4$ and the other $R^4$ may be optionally conbined with each other to form a ring with an alkylene chain (e.g. -(CH$_2$)$_2$-).

In the production method of this invention, the intermediate compound, a semicarbazone derivative (II), can be produced by the method as shown below.

The reaction step of producing the intermediate semicarbazone derivative (II) by allowing a hydrazone derivative (I) to react with 2,2-dialkoxyethyl isocyanate, which is shown by the following reaction:

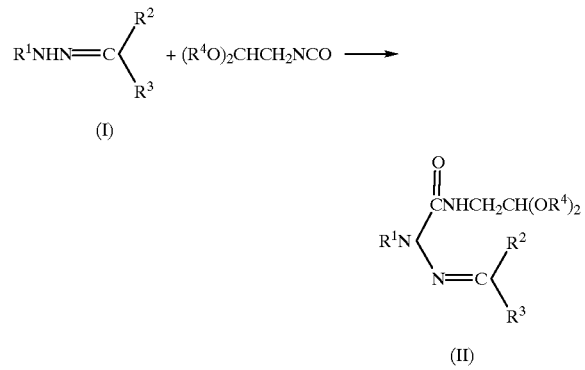

wherein $R^1$, $R^2$, $R^3$ and $R^4$ are of the same meaning as defined above, is conducted usually in an inert solvent or in the absence of solvent, optionally in the presence of a base. While the reaction temperature varies with the kinds of solvents employed, it ranges usually from about −20 to 110° C., especially preferably from about 0 to 50° C. While the reaction time varies with the kinds of solvents employed, it ranges usually from about 10 minutes to 5 hours, preferably from 30 minutes to 2 hours.

As the solvent for this reaction, almost all inert solvents can be employed, i.e. solvents commonly employed in the general chemical reactions, as exemplified by benzene, ligroin, benzine, toluene, xylene, methylene chloride, ethylene chloride, chloroform, carbon tetrachloride, dichloroethane, chlorobenzene, o-dichlorobenzene, ethers (e.g. diethyl ether, diisopropyl ether, dibutyl ether, glycol dimethyl ether, diglycol dimethyl ether, tetrahydrofuran and dioxane), ketone (e.g. acetone, methyl ethyl ketone, methyl isopropyl ketone and methyl isopropyl ketone), ester (e.g. ethyl acetate ester), nitrile (e.g. acetonitrile and propionitrile), amide (e.g. dimethylformamide, dimethylacetamide and hexamethyl phosphoric triamide), dimethyl sulfoxide and pyridine.

The amount of 2,2-dialkoxy ethyl isocyanate ranges usually from 1.0 to 3.5 mol., preferably from 1.0 to 1.5 mol., relative to the hydrazone derivative (I).

For allowing the reaction to proceed smoothly, a base may optionally be added. Examples of the base to be employed for this purpose include inorganic bases such as sodium carbonate, potassium carbonate, calcium carbonate, sodium hydroxide and potassium hydroxide, and organic bases such as triethylamine, pyridine, dimethyl aniline, picoline, 1,5-diazabicyclo[4,3,0]non-5-ene, 1,4-diazabicyclo[2,2,2]octane, 1,8-diazabicyclo[5,4,0]-7-undecene (DBU). The amount of the base to be employed ranges from 0.001 to 30.0%, weight percent preferably from 0.01 to 5.0%, relative to the starting material (I).

Among the semicarbazone derivative (II) obtained by the above method, $R^1$ is defined as the derivative (II') having a residual group:

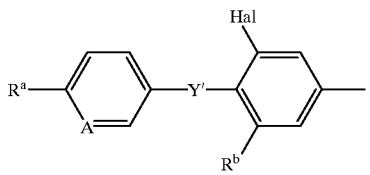

wherein $R^2$ is acyl, optionally substituted sulfamoyl, optionally substituted carbamoyl, carboxyl, alkoxycarbonyl, optionally substituted alkyl or optionally substituted amino; A is —CH— or nitrogen atom, Y' is methylene, cyanomethylene, carbonyl, hydroxymethylene, sulfur atom, sulfinyl, sulfonyl or oxygen atom; Hal is halogen (e.g. chlorine), $R^b$ hydrogen, halogen (e.g . chlorine) or lower alkyl (e.g. methyl). This derivative (II) is a novel compound and important intermediate for obtaining useful 1,2,4-triazine-3-one derivative (III).

The semicarbazone derivative (II) synthesized by the above-described reaction is subjected to a ring-closure reaction by a conventional method to convert into a 2-substituted-1,2,4-triazin-3-one derivative (III).

The derivative (III) includes the derivatives (III-a), (III-b), (III-c), (III-d) and (III-e). Each derivative can be produced by the following steps.

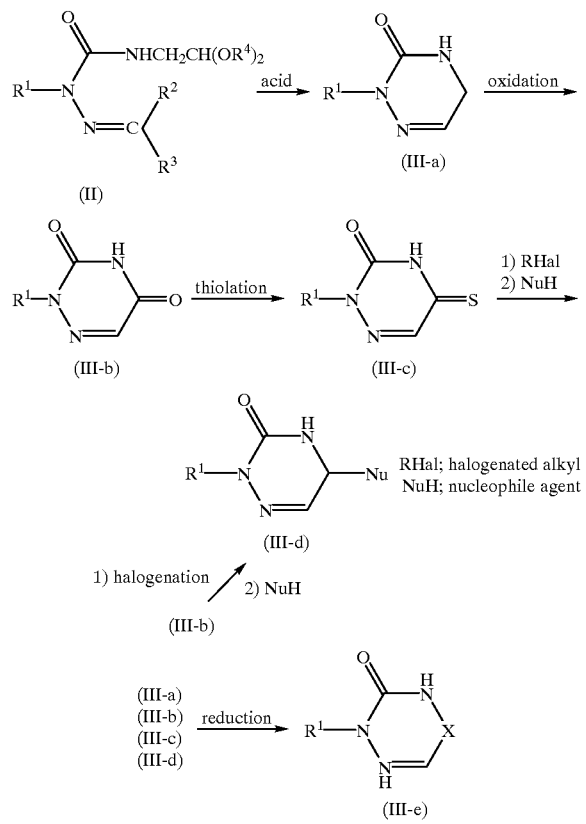

[the simbols are the same as defined before]

The 2-substituted-1,2,4-triazine-3-one derivative (III-a) is produced by ring-closure reaction of the semicarbazone derivative (II) and the 2-substituted-1,2,4-triazine-3,5-dione derivative (III-b) is produced by oxidation reaction of the derivative (III-a). The 2-substituted-1,2,4-triazine-3-one-5-thione derivative (III-c) is obtainable by thiolation reaction of the derivative (III-b). The 2-substituted-5-mono (or di) substituted-1,2,4-triazin-3-one (III-d) is producible from the derivative (III-c) or (III-b). Thus obtained derivative (III-a), (III-b), (III-c) or (III-d) is subjected to reduction reaction to obtain the derivative (III-e) in high yield.

The reaction (II)–(II-a) is conducted usually in an inert solvent or in the absence of solvent, optionally in the presence of an acid. While the reaction temperature varies with the kinds of solvents employed for the reaction, it ranges usually from about −20 to 150° C., especially from about 0 to 80° C. While the reaction time varies with the kinds of solvents employed for the reaction, it ranges usually from about 10 minutes to 5 hours, preferably from 30 minutes to 2 hours.

As the solvent for this reaction, almost all inert solvents can be employed, i.e. solvents commonly employed in the general chemical reactions, as exemplified by benzene, ligroin, benzine, toluene, xylene, methylene chloride, ethylene chloride, chloroform, carbon tetrachloride, dichloroethane, chlorobenzene, o-dichlorobenzene, ethers (e.g. diethyl ether, diisopropyl ether, dibutyl ether, glycol dimethyl ether, diglycol dimethyl ether, tetrahydrofuran and dioxane), ketone (e.g. acetone, methyl ethyl ketone and methyl isopropyl ketone), ester (e.g. ethyl acetate ester), nitrile (e.g. acetonitrile and propionitrile), amide (e.g. dimethylformamide, dimethylacetamide and hexamethyl phosphoric acid triamide), alcohol (e.g. methyl alcohol, ethyl alcohol propyl alcohol, isopropyl alcohol), pyridine and dimethyl sulfoxide.

In the reaction of converting a semicarbazone derivative (II) to a 2-substituted-1,2,4-triazin-3-one derivative by ring-closure reaction, an acid or a Lewis acid may be added for the purpose of allowing the reaction to proceed smoothly. Examples of the acid employed for this purpose include trichloroacetic acid, trifluoroacetic acid, p-toluene sulfonic acid, methane sulfonic acid, sulfuric acid, hydrochloric acid, phosphoric acid and polyphosphoric acid and example of the Lewis acid is trifluoroborane etherate.

In the production method of this invention, the object 1,2,4-triazin-3-one derivative (III) can be produced in a high yield by subjecting the reaction mixture to ring-closure reaction, without isolating the semicarbazone derivative (II) from the reaction mixture obtained by the above-mentioned reaction a). This one-pot reaction is preferably employed for producing the object compound (III) on an industrial scale.

The 1,2,4-triazin-3-one derivative (III-a) produced by the above-described reaction step can be used per se as agricultural chemicals and drugs for controlling parasitic pest. By subjecting these compounds to further reaction such as oxidation, reduction and substitution in accordance with conventional methods, various triazine derivatives such as 1,2,4-triazine-3,5-dione derivatives, 1,2,4-triazine-3-oxo-5-thione derivatives, 1,2,4-triazin-3-one-5-amino derivative and hexahydro-1,2,4-triazin-3-one derivatives can be produced conveniently and in a high yield. For example, by employing a 2-substituted-1,2,4-triazin-3-one derivative synthesized by the above-described reaction step, a 2-substituted 1,2,4-triazine-3,5-dione derivative can be produced in a high yield by a conventional oxidation reaction. This oxidation reaction can be conducted by using a oxidizing agent described in, for example, I & II of Shin Jikken Kagaku Koza Vol. 15 (compiled by The Chemical Society of Japan, Published by Maruzen Co., Ltd., 1976).

This reaction is conducted usually in an inert solvent, optionally in the presence of a base or an acid. While the reaction temperature varies with the kinds of solvents, it ranges usually from about 20 to 180° C., preferably from about 50 to 100° C. While the reaction time varies with the kinds of solvents, it ranges usually from about one hour to 15 hours, preferably from 3 hours to 8 hours. As the solvent for this reaction, almost all inert solvents can be employed, i.e. solvents commonly employed in the general chemical reactions, as exemplified by benzene, ligroin, benzine, toluene, xylene, methylene chloride, ethylene chloride, chloroform, carbon tetrachloride, dichloroethane, chlorobenzene, o-dichlorobenzene, ethers (e.g. dibutyl ether, glycol dimethyl ether, diglycol dimethyl ether, tetrahydrofuran and dioxane), ketone (e.g. methyl ethyl ketone, methyl isopropyl ketone and methyl isopropyl ketone), ester (e.g. ethyl acetate ester), nitrile (e.g. acetonitrile and propionitrile), amide (e.g. dimethylformamide, dimethylacetamide and hexamethyl phosphoric acid triamide), dimethyl sulfoxide, mercaptoacetic acid, acetic acid and pyridine.

Among the 1,2,4-triazine derivative (III) which is produced by the method of the present invention, the following derivative (III') is very effective for controlling parasitic protozoa.

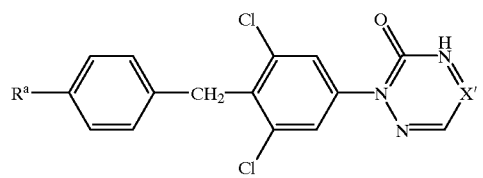

(III')

wherein $R^2$ is acyl, optionally substituted sulfamoyl, optionally substituted carbanoyl, carboxyl, alkoxycarbonyl, optionally substituted alkyl or optionally substituted amino and X' is methylene or carbonyl.

The acyl means $C_{1-7}$ acyl such as formyl, acetyl, propionyl, isopropionyl, trifluoacetyl, and benzoyl. The optionally substituted sulfamoyl means aminosulfonyl and $C_{1-5}$ sulfamoyl such as methylaminosulfonyl, dimethylaminosulfonyl and morpholinosulfonyl. The optionally substituted carbamoyl means aminocarbonyl and $C_{1-7}$ carbamoyl such as methylaminocarbonyl, dimethylaminocarbonyl, and phenylaminocarbonyl. The alkoxycarbonyl means $C_{1-7}$ alkoxycarbonyl such as methoxycarbonyl, ethoxycarbonyl and phenoxycarbonyl. The optionally substituted alkyl means $C_{2-4}$ alkyl such as ethyl and isopropyl, and halogeno-$C_{1-4}$ alkyl such as chloromethyl, 1-chloroethyl, 1-fluoroethyl, trifluoromethyl and trifluoroethyl, and hydroxy-$C_{1-4}$ alkyl such as hydroxymethyl, 1-hydroxyethyl and 2-hydroxyethyl, and $C_{1-4}$ alkoxy-$C_{1-4}$ alkyl such as methoxymethyl, 1-methoxyethyl, 1-ethoxyethyl, 1-acetoxyethyl and 2-ethoxyethyl. The optionally substituted amino means di-$C_{1-4}$ alkyl amono such as dimethylamino and diethylamino.

Especially, 2-[4-(4-acetylbenzyl)-3,5-dichlorophenyl]-4,5-dihydro-1,2,4-triazin-3(2H)-one (Example No. 6) and 2-{3,5-dichloro-4-[4-(1-hydroxyethyl)benzyl]phenyl}-4,5-dihydro-1,2,4-triazin-3(2H)-one (Example No. 16) are very useful, because these show high effectiveness for controlling parasitic protozoa and have very low residue.

WORKING EXAMPLE

Reference Example 1

Synthesis of α-(3,4-dichlorophenyl)-α-(2,6-dichloro-4-nitrophenyl)acetonitrile

To 150 ml of 20% hydrous DMSO were added 6.15 g of 3,4-dichlorobenzyl cyanide, 8.13 g of 4-bromo-3,5-dichloronitrobenzene and 1.50 g of sodium hydroxide. The reaction was allowed to proceed for one hour at temperatures ranging from 60 to 70° C. After completion of the reaction, DMSO was removed, and the residue was dissolved in 50 ml of toluene. The solution was washed with water, dried and concentrated. To the concentrate was added ethyl alcohol to cause crystallization to afford the titled compound in a yield of 67%, m.p.171–172° C.

$^1$H-NMR(CDCl$_3$); 6.21(s,1H), 7.13–7.52(m,3H), 8.29(s, 2H).

Reference Example 2

Synthesis of 3,5-dichloro-4-(3,4-dichloro-α-cyanobenzyl) aniline

In 100 ml of methanol were dissolved 7.6 g of α-(3,4-dichlorophenyl)-α-(2,6-dichloro-4-nitrophenyl)acetonitrile and 0.8 g (50%) of Raney's nickel. The solution was subjected to reduction with three times as much mol. of hydrogen gas. Insolubles were removed from the reaction mixture, then the remaining solution was concentrated to give the titled compound in a yield of 95%, m.p.191–194° C.

$^1$H-NMR(CDCl$_3$); 3.97(br,2H), 5.98(s,1H), 6.67(s,2H), 7.12–7.47(m,3H).

Reference Example 3

Synthesis of 3,5-dichloro-4-(3,4-dichloro-α-cyanobenzyl) phenylhydrazine

In 40 ml of acetic acid was dissolved 3.0 g of 3,5-dichloro-4-(3,4-dichloro-α-cyanobenzyl)aniline. To the solution was then added 3 ml of 35% hydrochloric acid. To the mixture was added dropwise, while cooling at temperatures ranging from 10 to 12° C., a solution of 0.8 g of 98.5% sodium nitrite in 3 ml of water. The reaction mixture was stirred for 40 minutes under the same conditions, to which was then added 7.0 g of stannous chloride dissolved in 10 ml of 35% hydrochloric acid. The reaction mixture was poured into ice-water, which was then made into alkaline, followed by extraction with 200 ml of ethyl acetate. The extract was washed with water, dried over anhydrous magnesium sulfate, and concentrated to afford the titled compound in a yield of 96%, m.p.183–185° C.

$^1$H-NMR(DMSO-d$_6$); 4.26(br,2H), 6.25(s,1H), 6.87(s, 2H), 7.11–7.72(m,4H).

Reference Example 4

Synthesis of 1-[3,5-dichloro-4-(3,4-dichloro-α-cyanobenzyl)phenyl]-2-benzylidenehydrazine acetic acid ethyl ester In 50 ml of acetic acid ethyl ester was dissolved 3.0 g of 3,5-dichloro-4-(3,4-dichloro-α-cyanobenzyl) phenylhydrazine. To the solution was added equimol. of benzaldehyde, and the mixture was stirred for 3 hours at room temperature. The reaction mixture was dried over anhydrous magnesium sulfate, which was then concentrated to afford the titled compound in a yield of 68%, m.p.75–90° C.

$^1$H-NMR(CDCl$_3$); 1.25(t,3H), 2.04(s,3H), 4.12(q,2H), 6.03(s,1H), 7.13(s,2H), 7.24–7.81(m,10H).

Reference Example 5
Synthesis of α-(4-chlorophenyl)-α-(2,6-dichloro-4-nitrophenyl)methane To 50 ml of 20% hydrous DMSO were added 1.9 g of 4-chlcrophenyl acetic acid methyl ester, 2.7 g of 4-bromo-3,5-dichloronitrobenzene and 0.5 g of sodium hydroxide. The reaction was allowed to proceed at temperatures ranging from 60 to 70° C. for one hour, then at temperatures ranging from 130 to 135° C. for 8 hours. After completion of the reaction, DMSO was removed. The residue was dissolved in 50 ml of toluene. The solution was washed with water, dried and concentrated. To the concentrate was added ethyl alcohol to cause crystallization to afford the titled compound in a yield of 91%, m.p.80–81° C.

$^1$H-NMR(CDCl$_3$); 4.36(s,2H), 7.17(q,4H), 8.20(s,2H).

Reference Example 6
Synthesis of α-(4-chlorophenyl)-α-(2,6-dichloro-4-aminophenyl)methane In 30 ml of methanol were dissolved 1.6 g of α-(4-chlorophenyl)-α-(2,6-dichloro-4-nitrophenyl)methane and 0.2 g (50%) of Raney's hickel. The solution was subjected to reduction with three times as much mol. of hydrogen gas. Insolubles were removed and the remaining reaction mixture was concentrated to afford the titled compound in a yield of 95%, m.p.141–142° C.

$^1$H-NMR(CDCl$_3$); 3.72(br,2H), 4.14(s,2H), 6.65(s,2H), 6.95–7.44(m,4H).

Reference Example 7
Synthesis of α-(4-chlorophenyl)-α-(2,6-dichloro-4-hydrazinophenyl)methane In 20 ml of acetic acid was dissolved 1.5 g of α-(4-chlorophenyl)-α-(2,6-dichloro-4-aminophenyl)methane. To the solution was then added 3 ml of 35% hydrochloric acid. To the mixture was added dropwise, while cooling at temperatures ranging from 10 to 12° C., 0.4 g of 98.5% sodium nitrite dissolved in 1 ml of water. The reaction mixture was stirred for 40 minutes under the same conditions, to which was then added 4.0 g of stannous chloride dissolved in 4 ml of 35% hydrochloric acid. The reaction mixture was poured into ice-water, and the pH of the solution was made alkaline, followed by extraction with 50 ml of acetic acid ethyl ester. The extract was washed with water, dried over anhydrous magnesium sulfate, and concentrated to afford the titled compound in a yield of 95%, m.p.129–130° C.

$^1$H-NMR(CDCl$_3$); 3.57(br,2H), 4.17(s,2H), 5.23(br,1H), 6.83(s,2H), 7.03–7.27(q,4H).

Reference Example 8
Synthesis of α-(4-chlorophenyl)-α-(2,6-dichloro-4-benzylidene hydrazinophenyl)methane In 50 ml of dichloromethane was dissolved 0.7 g of α-(4-chlorophenyl)-α-(2,6-dichloro-4-hydrazinophenyl)methane. To the solution was added equimol. of benzaldehyde, and the mixture was stirred for 3 hours at room temperature. The reaction mixture was dried over anhydrous magnesium sulfate, followed by concentration to afford the titled compound in a yield of 98%, m.p.149–150° C.

$^1$H-NMR(CDCl$_3$); 4.20(s,2H), 7.09–7.68(m,13H).

Reference Example 9
Synthesis of benzaldehyde 4-(4-chloro-α-cyanobenzyl)-3,5-dichlorophenyl hydrazone In 30 ml of acetic acid ethyl ester was dissolved 3.26 g of 4-(4-chloro-α-cyanobenzyl)-3,5-dichlorophenyl hydrazine. To the solution was added equimolar benzaldehyde and three times as much mol. of anhydrous magnesium sulfate, then the reaction was allowed to proceed for one hour at room temperature. After completion of the reaction, insolubles were removed, and the solution was concentrated, which was recrystallized from acetonitrile to afford 3.3 g of the titled compound as colorless crystals, m.p.162–163° C.

$^1$H-NMR(CDCl$_3$); 6.05(s,1H), 7.09(s,2H), 7.30(s,4H), 7.30–8.00(m,7H).

Reference Example 10
Synthesis of 4-(4-Acetylbenzyl)-3,5-dichloroaniline

In 11 ml of ethylacetate were dissolved 1.1 g 4-(4-Acetylbenzyl)-3,5-dichloronitrobenzene and 3.8 g Tin (11) chloride dihydrate. The solution was allowed to proceed for one hour at temperatures ranging from 40–50° C. After completion of the reaction. The reaction mixture was poured into 100 ml ice-water, followed by extraction with 150 ml ethylacetate. The extract was washed with water and 25% ammonia solution, dried over anhydrous magnesium sulfate, and concentrated to afford the titled compound in a yield of 100%, m.p.97–98° C.

$^1$H-NMR(CDCl$_3$); 2.55(s,3H), 3.75(br,2H), 4.24(s,2H), 6.67(s,2H), 7.25(d,2H), 7.85(d,2H).

Reference Example 11
Synthesis of 2-[4-(4-Acetylbenzyl)-3,5-dichlorophenyl]-1-benzylidenehydrazine In 10 ml of acetic acid was dissolved 1.0 g of 4-(4-Acetylbenzyl)-3,5-dichloroaniline. To the solution was then added 1.0 ml of 35% hydrochloric acid. To the mixture was added dropwise, while cooling at temperatures ranging from 8–10° C., a solution of 0.3 g of 98.5% sodium nitrite in 1.0 ml water. The reaction mixture was stirred for one hour under the same conditions, to which was then added 2.0 g of Tin (II) chloride dihydrate dissolved in 2.0 ml of 35% hydrochloric acid. The reaction mixture was stirred for 3 hours at room temperature. To the mixture then added 20 ml of water and 20 ml chloroform. To the mixture was added dropwise, while cooling at the temperatures ranging from 5–10° C., 0.36 g of benzaldehyde. The reaction mixture was stirred for 30 minutes under the same conditions. After completion of the reaction, followed by extraction with 20 ml of chloroform. The extract was washed with water and sturated sodium hydrogen carbonate solution, dried over an hydrous magnesium sulfate, and concentrated to provide 0.88 g of the title compound as a colorless crystals, m.p.137–139° C.

$^1$H-NMR(CDCl$_3$); 2.56(s,3H), 4.29(s,2H), 7.11–7.90(m, 13H).

Working Example 1
Synthesis of 1-benzylidene-2-[4-(4-chlorobenzyl)-3,5-dichlorophenyl]-4-(2,2-diethoxyethyl)-semicarbazide In 5 ml of acetonitrile was dissolved 0.5 g of α-(4-chlorophenyl)-α-(2,6-dichloro-4-benzylidenehydrazinophenyl)methane. To the solution were added 0.3 g of 2,2-diethoxyethylisocyanate and 0.015 g of DBU. The mixture was stirred for one hour at room temperature. The reaction mixture was cooled, then the resulting crystalline precipitate was collected by filtration to give the titled compound in a yield of 97%, m.p.138–139° C.

$^1$H-NMR(CDCl$_3$); 1.27(t,6H), 3.46–3.90(m,6H), 4.33(s, 2H), 6.92–7.63(m,13H).

Working Example 2
Synthesis of 1-benzylidene-2-[4-(4-chloro-α-cyanobenzyl)-3,5-dichlorophenyl]-4-(2,2-dimethoxyethyl)semicarbazide In 20 ml of acetonitrile was suspended 3.2 g of benzaldehyde 4-(4-chloro-α-cyanobenzyl)-3,5-dichlorophenyl hydrazone. To the suspension were added 1.5 g of 2,2-dimethoxyethyl isocyanate and 20 mg of DBU. The reaction was allowed to proceed for one hour at room temperature, then the resulting crystalline precipitate was collected by filtration, which was washed with hexane, followed by drying to afford 3.7 g of the titled compound as colorless crystals, m.p.190–191° C.

$^1$H-NMR(CDCl$_3$); 3.46(s,6H), 3.53(t,2H), 4.50(t,1H), 6.21(s,1H), 6.80–7.10(m,1H), 7.20–7.70(m,12H).

Working Example 3
Synthesis of 2-[4-(3-Acetylbenzyl)-3,5-dichlorophenyl]-1-benzylidene-4-(2,2-dimethoxyethyl)semicarbazide In 8 ml of acetonitrile was dissolved 0.8 g of 2-[4-(4-Acetylbenzyl)-3,5-dichlorophenyl]-1-benzylidenehydrazine. To the solution were added 0.4 g 2,2-dimethoxyethylisocyanate and 0.015 g of DBU. The mixture was stirred for one hour at room temperature. The reaction mixture was poured into 30 ml ice-water, followed by extraction with ethylacetate. The extract was washed with water, dried over anhydrous magnesium sulfate and concentrated. This residue was purified by column chromatography (Merck silica 60; hexane-ethylacetate=1:3) to provide 0.73 g of the title compound as a light-yellow oil.

$^1$H-NMR(CDCl$_3$); 2.58(s,3H), 3.47(s,6H), 3.53(5,2H)), 4.15(5,1H), 4.43(s,2H), 6.90–7.90(m,13H).

Working Example 4

Compounds produced by substantially the same manner as in Working Example 1–3 and their physical constants were set forth in Table 1.

TABLE 1

| No. | Compounds | m.p. (° C.) | $^1$H-NMR [Solvent] δ |
|---|---|---|---|
| 1 | (structure) | 146~147 | [CDCl$_3$] 3.48(s, 6H) 3.55(t, 2H) 4.52(t, 1H) 6.94(t, 1H) 7.15~7.87(m, 12H) |
| 2 | (structure) | 162~163 | [CDCl$_3$] 3.45(s, 6H) 3.53(t, 2H) 4.51(t, 1H) 6.92(t, 1H) 7.10~7.70(m, 12H) |
| 3 | (structure) | 139~140 | [CDCl$_3$] 3.48(s, 6H) 3.55(t, 2H) 4.11(s, 2H) 4.53(t, 1H) 6.93(br, 1H) 7.05~7.70 (m, 13H) |
| 4 | (structure) | 119~120 | [CDCl$_3$] 3.43(s, 6H) 3.51(t, 2H) 4.48(t, 1H) 7.10~7.75(m, 8H) 7.80(s, 1H) |
| 5 | (structure) | 149~150 | [CDCl$_3$] 3.45(s, 6H) 3.52(t, 2H) 4.31(s, 2H) 4.49(t, 1H) 6.91(t, 1H) 7.10~7.75 (m, 12H) |
| 6 | (structure) | 190~191 | [CDCl$_3$] 3.32(dd, 2H) 3.48(s, 6H) 3.53(t, 1H) 4.50(t, 1H) 4.92(t, 1H) 6.91(br, 1H) 7.15~7.65(m, 12H) |

TABLE 1-continued

| No. | Compounds | m.p. (° C.) | ¹H-NMR [Solvent] δ |
|---|---|---|---|
| 7 | | caramel | [CDCl$_3$] 1.71(s, 3H) 2.16(s, 3H) 3.41(s, 6H) 3.35~3.47(m, 2H) 4.22(s, 2H) 4.43(t, 1H) 5.98(br, 1H) 7.03~7.27(q, 4H) 7.32(s, 2H) |
| 8 | | 140~141 | [CDCl$_3$] 1.27(t, 6H) 3.46~3.90(m, 6H) 4.33(s, 2H) 4.64 (t, 1H) 6.92~7.63(m, 13H) |
| 9 | | 160~162 | [CDCl$_3$] 1.28(t, 6H) 3.46~3.90(m, 6H) 4.63(t, 1H) 6.20 (s, 1H) 6.99(t, 1H) 7.13~7.68 (m, 11H) |
| 10 | | caramel | [CDCl$_3$] 2.21(s, 3H) 3.49~3.62(m, 8H) 4.54(t, 1H) 6.92~7.82(m, 13H) |
| 11 | | 163~164 | [CDCl$_3$] 2.32(s, 3H) 3.47~3.60(m, 8H) 4.02(s, 2H) 4.52 (t, 1H) 6.83~7.60(m, 13H) |
| 12 | | 178~183 | [CDCl$_3$] 3.39~3.56(m, 2H) 3.47(s, 6H) 4.51(t, 1H) 6.20 (s, 1H) 7.23~7.67(m, 12H) |
| 13 | | caramel | [CDCl$_3$] 2.49(s, 3H) 2.43~3.60(m, 8H) 4.54(t, 1H) 6.93~7.58(m, 9H) |
| 14 | | caramel | [DMSO-d$_6$] 2.50(s, 3H) 3.40~3.66(m, 8H) 4.52(t, 1H) 6.18 (s, 1H) 6.90~7.73(m, 9H) |

TABLE 1-continued

| No. | Compounds | m.p. (° C.) | ¹H-NMR [Solvent] δ |
|---|---|---|---|
| 15 | | caramel | [CDCl$_3$] 2.12(s, 3H) 3.43~3.63(m, 2H) 3.49(s, 6H) 4.55 (t, 1H) 6.91~7.67(m, 13H) |
| 16 | | caramel | [CDCl$_3$] 2.21(s, 3H) 3.48~3.61(m, 2H) 3.48(s, 6H) 4.54 (t, 1H) 6.73~7.60(m, 13H) |
| 17 | | oil | [CDCl$_3$] 1.18(t, 3H) 1.35(t, 3H) 3.45(s, 6H) 3.60(t, 2H) 3.85(q, 2H) 4.40(t, 1H) 4.45 (q, 2H) 6.90~7.60(m, 4H) |
| 18 | | — | — |
| 19 | | oil | [CDCl$_3$] 3.48(S, 6H) 3.66(t, 2H) 4.52(t, 1H) 6.95(t, 1H) 7.14(q, 4H) 7.45(S, 2H) 7.20~7.82(m, 6H) |
| 20 | | 194~195 | [CDCl$_3$] 2.35(S, 3H) 3.48(S, 6H) 3.52(t, 2H) 4.51(t, 1H) 6.22(S, 1H) 6.92(br, 1H) 7.10~7.90(m, 12H) |
| 21 | | oil | [CDCl$_3$] 2.58(s, 3H) 3.47(s, 6H) 3.53(m, 2H) 4.51(t, 1H) 4.43(s, 2H) 6.90~7.90 (m, 13H) |
| 22 | | — | — |

TABLE 1-continued

| No. | Compounds | m.p. (° C.) | $^1$H-NMR [Solvent] δ |
|---|---|---|---|
| 23 | | 161~162 | [CDCl$_3$] 3.47~3.59(m, 8H) 4.51(t, 1H) 6.22(s, 1H) 6.90 (br, 1H) 7.27~7.66(m, 11H) |
| 24 | | 166~168 | [CDCl$_3$] 2.40(s, 3H) 3.47~ 3.60(m, 8H) 4.52(t, 1H) 6.08 (s, 1H) 6.93(t, 1H) 7.06~7.64 (m, 11H) |
| 25 | | 144~145 | [DMSO-d$_6$] 2.27(s, 3H) 3.32 (s, 6H) 3.27~3.66(m, 2H) 4.50(t, 1H) 6.37(s, 1H) 7.36~ 7.96(m, 12H) |
| 26 | | 185~186 | [CDCl$_3$] 3.98(s, 6H) 3.53(t, 2H) 3.91(s, 3H) 4.50(t, 1H) 6.24(s, 1H) 6.65~7.75 (m, 12H) |
| 27 | | 145~146 | [CDCl$_3$] 2.28(s, 3H) 3.48(s, 6H) 3.55(t, 2H) 4.51(t, 1H) 6.20(s, 1H) 6.75~7.80 (m, 12H) |
| 28 | | 184~185 | [CDCl$_3$] 3.48(s, 6H) 3.54(t, 2H) 4.51(t, 1H) 6.28(s, 1H) 6.95(br, 1H) 7.20~7.75 (m, 12H) |
| 29 | | 90~92 | [CDCl$_3$] 3.48(s, 6H) 3.39~ 3.60(m, 2H) 4.50(t, 1H) 5.83 (s, 1H) 6.85~7.70(m, 13H) |
| 30 | | 90~92 | [CDCl$_3$] 2.16(s, 3H) 3.53~ 3.82(m, 8H) 4.52(t, 1H) 6.28 (s, 1H) 6.80~7.67(m, 12H) |

TABLE 1-continued

| No. | Compounds | m.p. (° C.) | ¹H-NMR [Solvent] δ |
|---|---|---|---|
| 31 | | 77~78 | [CDCl₃] 3.48(s, 6H) 3.51~3.64(m, 2H) 4.49(t, 1H) 7.13~7.93(m, 14H) |
| 32 | | 62~63 | [CDCl₃] 2.44(s, 3H) 3.40~3.61(m, 8H) 4.57(t, 1H) 6.90~7.80(m, 14H) |
| 33 | | oil | [CDCl₃] 3.48(s, 6H) 3.54(t, 2H) 4.51(t, 1H) 4.57(s, 2H) 6.92(br, 1H) 7.20~7.70 (m, 8H) |
| 34 | | 133~134 | [CDCl₃] 3.47~3.58(m, 8H) 4.33(s, 2H) 4.51(t, 1H) 6.91 (t, 1H) 7.19~7.63(m, 10H) 8.37(d, 1H) |
| 35 | | 146~147 | [CDCl₃] 3.30~3.68(m, 8H) 4.51(t, 1H) 6.30(s, 1H) 6.95 (br, 1H) 7.10~7.85(m, 12H) |
| 36 | | 188~190 | [CDCl₃] 3.40~3.70(m, 8H) 4.51(t, 1H) 6.31(s, 1H) 6.98 (br, 1H) 7.20~7.90(m, 12H) |
| 37 | | resinous | [DMSO-d₆] 2.46(s, 3H) 3.19~3.43(m, 8H) 4.56(t, 1H) 6.46 (s, 1H) 7.29~7.89(m, 10H) 8.31(d, 1H) |
| 38 | | — | — |

TABLE 1-continued

| No. | Compounds | m.p. (° C.) | ¹H-NMR [Solvent] δ |
|---|---|---|---|
| 39 | | 132~134 | [CDCl₃] 3.47~3.58(m, 8H) 4.33(s, 2H) 4.51(t, 1H) 6.91 (t, 1H) 7.19~7.63(m, 10H) 8.37(d, 1H) |
| 40 | | oil | [CDCl₃] 3.47~3.56(m, 8H) 4.50(t, 1H) 6.25(s, 1H) 6.79~ 6.97(m, 2H) 7.30~7.58 (m, 9H) |
| 41 | | 199~201 | [CDCl₃] 2.30(s, 3H) 3.47~ 3.60(m, 8H) 4.52(t, 1H) 6.15 (s, 1H) 6.93(t, 1H) 7.04~ 7.66(m, 12H) |
| 42 | | caramel | [CDCl₃] 2.17(s, 3H) 3.33~ 3.68(m, 4H) 3.48(s, 6H) 4.52 (t, 1H) 6.49(s, 1H) 6.94(t, 1H) 7.17~7.60(m, 12H) |
| 43 | | 149~151 | [CDCl₃] 1.96(s, 3H) 3.48~ 3.60(m, 8H) 3.72(q, 2H) 4.52 (t, 1H) 6.09(s, 1H) 6.94(t, 1H) 7.19~7.65(m, 12H) |
| 44 | | 121~122 | [CDCl₃] 1.22(t, 3H) 2.97(q, 2H) 3.47~3.59(m, 8H) 4.42~ 4.58(m, 3H) 6.91~7.94 (m, 13H) |
| 45 | | caramel | [CDCl₃] 1.21(d, 6H) 3.47~ 3.60(m, 8H) 4.12(m, 1H) 4.43 (s, 2H) 4.52(t, 1H) 6.91(t, 1H) 7.25~7.94(m, 12H) |
| 46 | | 158~160 | [CDCl₃] 3.47~3.60(m, 8H) 4.46(s, 2H) 4.52(t, 1H) 6.92(t, 1H) 7.29~7.80(m, 16H) |

Working Example 5
Synthesis of 2-[3,5-dichloro-4-(4-chlorobenzyl)phenyl]-4,5-dihydro-1,2,4-triazin-3(2H)-one In 5 ml of acetonitrile was dissolved 0.4 g of 1-benzylidene-2-[4-(4-chlorobenzyl)-3,5-dichlorophenyl]-4-(2,2-diethoxyethyl)-semicarbazide. To the solution was added one drop of 35% hydrochloric acid. The mixture was stirred for one hour at room temperature. The reaction mixture was cooled, then resulting crystalline precipitate of the titled compound was collected by filtration. The yield was 95%. m.p.199–200° C.

$^1$H-NMR(CDCl$_3$); 4.05(t,2H), 4.25(s,2H), 6.50(br,1H), 7.05(t,1H), 7.19(s,4H), 7.60(s,2H).

Working Example 6
Synthesis of 2-[4-(4-acetylbenzyl)-3,5-dichlorophenyl]-4,5-dihydro-1,2,4-triazin-3(2H)-one In 7 ml of ethyl acetate was dissolved 0.7 g of 2-[4-(4-acetylbenzyl)-3,5-dichlorophenyl]-1-benzylidene-4-(2,2-dimethoxyethyl)semicarbazide. To the solution was added 0.27 g of 35% hydrochloric acid. The mixture was stirred for one hour at room temperature. The reaction mixture was washed with water, dried and concentrated. The residue was purified by column chromatography (Merck Silica Gel 60; normalhexane-ethylacetate=1:3) to provide 0.24 g of the title compound. m.p.189–190° C.

$^1$H-NMR(CDCl$_3$); 2.56(s.3H), 4.14(5,2H), 4.35(s,2H), 5.60(br,1H), 7.11(m,1H), 7.28(d,2H), 7.62(s,2H), 7.85(d, 2H).

Working Example 7
Compounds produced by substantially the same manner as in Working Example 5 and their physical constants were set forth in Table 2.

TABLE 2

| No. | Compounds | m.p. (° C.) | $^1$H-NMR [Solvent] δ |
|---|---|---|---|
| 1 | | 109~110 | [CDCl$_3$] 4.15(t, 2H) 6.52(br, 1H) 7.10(q, 4H) 7.23(br, 1H) 7.86(s, 2H) |
| 2 | | 222~223 | [CDCl$_3$] 4.14(m, 2H) 4.28(s, 2H) 5.85(br, 1H) 7.00~7.30(m, 5H) 7.50(d, 1H) |
| 3 | | 210~211 | [CDCl$_3$] 2.38(s, 3H) 4.10~4.13 (m, 2H) 5.92(br, 1H) 6.02(s, 1H) 7.11~7.61(m, 6H) |
| 4 | | 221~222 | [CDCl$_3$] 4.12~4.17(m, 2H) 5.67 (br, 1H) 6.14(s, 1H) 7.12~7.57(m, 4H) 7.73(s, 2H) |
| 5 | | 215~216 | [CDCl$_3$] 2.30(s, 3H) 4.16(m, 2H) 5.80(br, 1H) 6.23(s, 1H) 7.06~7.46 (m, 6H) |
| 6 | | 197~198 | [CDCl$_3$] 3.99(m, 2H) 6.40~6.76 (m, 2H) 6.92~7.33(m, 6H) 7.63(s, 2H) |

TABLE 2-continued

| No. | Compounds | m.p. (° C.) | ¹H-NMR [Solvent] δ |
|---|---|---|---|
| 7 | | 146~147 | [CDCl$_3$] 4.07(s, 2H) 4.14(m, 2H) 6.04(br, 1H) 6.88~7.36(m, 7H) |
| 8 | | 97~99 | [CDCl$_3$] 4.08~4.19(m, 2H) 5.75 (s, 1H) 5.95(s, 1H) 7.15~7.39 (m, 5H) 8.00(m, 2H) |
| 9 | | 212~213 | [CDCl$_3$] 2.33(s, 3H) 4.10(m, 2H) 6.12(s, 1H) 6.34(br, 1H) 7.11(t, 1H) 7.19(s, 4H) 7.70(s, 2H) |
| 10 | | 213~214 | [CDCl$_3$] 2.28(s, 3H) 4.14(m, 2H) 5.76 (s, 1H) 5.98(s, 1H) 7.12~7.37(m, 4H) 7.74(s, 2H) |
| 11 | | 220~221 | [CDCl$_3$] 2.56(s, 3H) 4.17(m, 2H) 5.40(br, 1H) 6.90(d, 2H) 7.14(m, 1H) 7.69(s, 2H) 7.93(d, 2H) |
| 12 | | 189~190 | [CDCl$_3$] 2.56(s, 3H) 4.14(m, 2H) 4.35(s, 2H) 5.60(br, 1H) 7.11(m, 1H) 7.28(d, 2H) 7.62(s, 2H) 7.85(d, 2H) |
| 13 | | 205~206 | [CDCl$_3$] 4.01(t, 2H) 4.24(s, 2H) 6.98(s, 1H) 6.90~7.45(m, 4H) 8.30(s, 1H) |
| 14 | | 161~162 | [CDCl$_3$] 3.28(s, 3H) 4.12~4.17(m, 2H) 4.44(q, 2H) 5.55(br, 1H) 6.00(s, 1H) 7.09~7.17(m, 1H) 7.28(q, 4H) 7.64(d, 1H) 7.70(d, 1H) |

TABLE 2-continued
| No. | Compounds | m.p. (° C.) | ¹H-NMR [Solvent] δ |
|---|---|---|---|
| 15 | 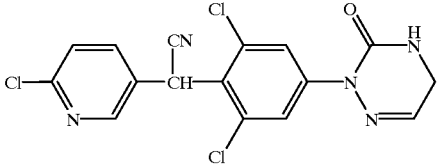 | 170~171 | [CDCl₃] 4.13~4.18(m, 2H) 5.64(br, 1H) 6.15(s, 1H) 7.13~7.21(m, 1H) 7.33(d, 1H) 7.67(ddd, 1H) 7.77(S, 2H) 8.40(dd, 1H) |
| 16 | 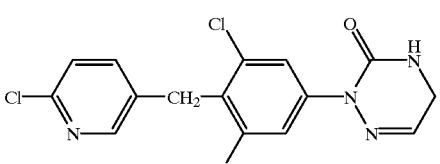 | 187~188 | [CDCl₃] 4.11~4.16(m, 2H) 4.25(s, 2H) 5.66(br, 1H) 7.07~7.14(m, 1H) 7.19(d, 1H) 7.46(dd, 1H) 7.62(s, 2H) 8.32(dd, 1H) |
| 17 | 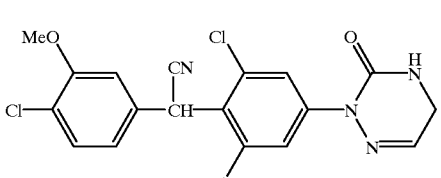 | 211~212 | [CDCl₃] 3.85(s, 3H) 4.02(m, 2H) 6.40(s, 1H) 6.79(d, 1H) 7.04(br, 1H) 7.39(br, 1H) 7.46(d, 1H) 7.79(s, 3H) |
| 18 | 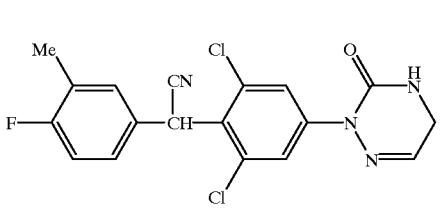 | 185~186 | [CDCl₃] 2.23(d, 3H) 4.09(m, 2H) 6.10(s, 1H) 6.54(br, 1H) 6.75~7.30 (m, 4H) 7.70(s, 2H) |
| 19 | 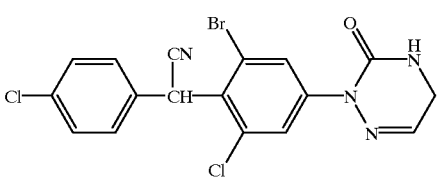 | 174~175 | [CDCl₃] 4.10(m, 2H) 6.18(s, 1H) 6.55(br, 1H) 7.13(t, 1H) 7.30(s, 4H) 7.74(d, 1H) 7.91(d, 1H) |
| 20 | 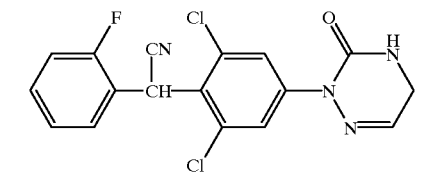 | 217~218 | [CDCl₃] 4.01(t, 2H) 6.48(s, 1H) 7.00~7.90(m, 6H) 7.85(s, 2H) |
| 21 | 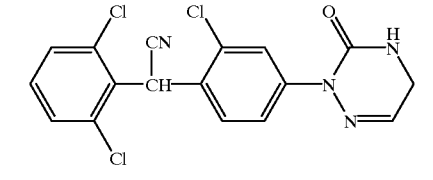 | 220~221 | [DMSO-d₆] 4.02(t, 2H) 6.36(s, 1H) 7.19~7.87(m, 7H) 8.28(s, 1H) |
| 22 | 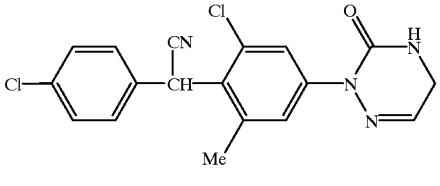 | 211~212 | [CDCl₃] 2.26(s, 3H) 4.10(t, 2H) 6.06(s, 1H) 7.00~7.70(m, 8H) |

TABLE 2-continued

| No. | Compounds | m.p. (° C.) | ¹H-NMR [Solvent] δ |
|---|---|---|---|
| 23 | 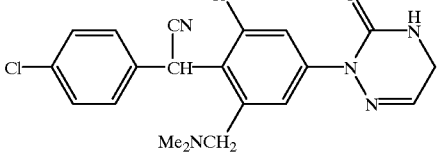 | caramel | [CDCl₃] 2.16(s, 6H) 3.44(q, 2H) 4.12~4.17(m, 2H) 5.41(br, 1H) 6.44(s, 1H) 7.08~7.36(m, 5H) 7.53(d, 1H) 7.64(d, 1H) |
| 24 | 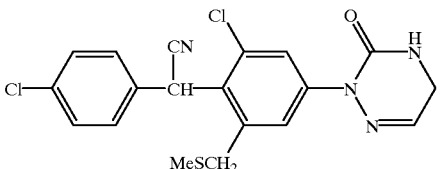 | caramel | [CDCl₃] 1.96(s, 3H) 3.71(q, 2H) 4.13~4.16(m, 2H) 5.88(br, 1H) 6.01(s, 1H) 7.10~7.39(m, 5H) 7.66(s, 2H) |
| 25 | 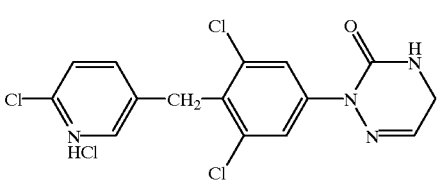 | 186~187 | [DMSO-d₆] 3.96~4.01(m, 2H) 4.25 (s, 2H) 7.29~7.75(m, 3H) 7.65(s, 2H) 8.26(d, 1H) 9.39(br, 2H) |
| 26 | 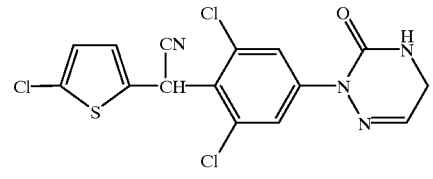 | 171~172 | [CDCl₃] 4.13(m, 2H) 6.03(br, 1H) 6.17(d, 1H) 6.78(d, 1H) 6.94(dd, 1H) 7.15(t, 1H) 7.74(s, 2H) |
| 27 | 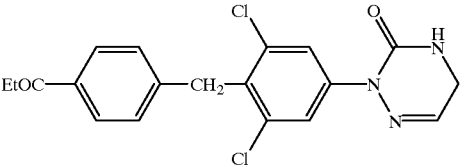 | 187~188 | [CDCl₃] 1.20(t, 3H) 2.95(q, 2H) 4.11~4.16(m, 2H) 4.35(s, 2H) 5.50(br, 1H) 7.07~7.31(m, 3H) 7.62(s, 2H) 7.85(d, 2H) |
| 28 | 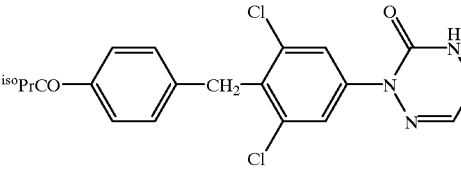 | 150~151 | [CDCl₃] 1.19(d, 6H) 3.51(m, 1H) 4.35(s, 2H) 5.75(br, 1H) 7.07~7.15(m, 1H) 7.27(d, 2H) 7.62(d, 2H) 7.85(d, 2H) |
| 29 | 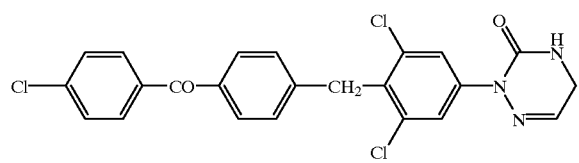 | 205~206 | [CDCl₃] 4.11~4.16(m, 2H) 4.38(s, 2H) 5.67(br, 1H) 7.05~7.15(m, 1H) 7.25~7.78(m, 10H) |

Working Example 8

Synthesis of 2-[3,5-dichloro-4-(4-chlorobenzyl)phenyl]-1,2,4-triazine-3,5(2H,4H)-dione In 2 ml of acetic acid were dissolved 0.2 g of 2-[3,5-dichloro-4-(4-chlorobenzyl)phenyl]-4,5-dihydro-1,2,4-triazine-3(2H)-one and 0.2 ml of hydrogenperoxide (30%). The reaction was allowed to proceed for 3 hours at temperatures ranging from 100 to 110° C. To the reaction mixture was added 20 ml of water to cause precipitation of the titled compound as crystalline product. The product was collected by filtration. The yield was 85%. m.p.175–176° C.

¹H-NMR(DMSO-d₆); 4.30(s,2H), 7.25(q,4H), 7.70(s, 1H), 7.74(s,2H), 12.46(br,1H).

Working Example 9

Compounds produced by substantially the same manner as in Working Example 8 and their physical constants were set forth in Table 3.

TABLE 3

| No. | Compounds | m.p. (° C.) | ¹H-NMR [Solvent] δ |
|---|---|---|---|
| 1 | | 183~184 | [CDCl₃] 2.57(s, 3H) 4.40(s, 2H) 7.27(d, 2H) 7.59(s, 1H) 7.66(s, 2H) 7.88(d, 2H) 9.35(br, 1H) |
| 2 | | 224~225 | [CDCl₃] 4.33(s, 2H) 7.19(q, 4H) 7.45(d, 1H) 7.56(s, 1H) 9.10(br, 1H) |
| 3 | | 234~235 | [DMSO-d₆] 7.27(q, 4H) 7.78(s, 1H) 8.03(s, 2H) 12.60(s, 1H) |
| 4 | | 294~295 | [DMSO-d₆] 6.49(br, 2H) 7.28(q, 4H) 7.71(s, 1H) 7.80(s, 2H) 12.50(s, 1H) |
| 5 | | 172~173 | [DMSO-d₆] 7.25(q, 4H) 7.72(s, 1H) 7.88(s, 2H) 12.50(s, 1H) |
| 6 | | 175~176 | [DMSO-d₆] 4.28(s, 2H) 7.25(q, 4H) 7.69(s, 1H) 7.73(s, 2H) 12.50(br, 1H) |
| 7 | | 106~107 | [DMSO-d₆] 7.28(d, 1H) 7.39(q, 4H) 7.72(s, 1H) 7.80(s, 2H) 12.50(br, 1H) |
| 8 | | 161~162 | [CDCl₃] 2.26(d, 3H) 7.19(d, 1H) 7.14~7.59(m, 7H) 8.95(br, 1H) |

TABLE 3-continued

| No. | Compounds | m.p. (° C.) | ¹H-NMR [Solvent] δ |
|-----|-----------|-------------|---------------------|
| 9 | (structure) | 221~222 | [DMSO-d$_6$] 2.18(s, 3H) 7.75(q, 4H) 7.89(s, 2H) 12.40(br, 1H) |
| 10 | (structure) | 261~262 | [CDCl$_3$] 2.32(s, 3H) 6.11(s, 1H) 7.17~7.42(m, 5H) 7.60(s, 1H) 7.66(d, 1H) |
| 11 | (structure) | 178~179 | [CDCl$_3$] 4.31(s, 2H) 7.26(s, 1H) 7.48 (dd, 1H) 7.63(d, 1H) 7.67(s, 2H) 8.33 (d, 1H) 8.78(br, 1H) |

Working Example 10
Production of 2-[4-(4-chloro-α-cyanobenzyl)-3,5-dichlorophenyl]-4,5-dihydro-1,2,4-triazin-3(2H)-one In 30 ml of acetonitrile was suspended 3.5 g of 1-benzylidene-2-[4-(4-chloro-α-cyanobenzyl)-3,5-dichlorophenyl]-4-(2,2-dimethoxyethyl)semicarbazide produced in Working Example 2. To the suspension was added 0.7 g of 35% hydrochloric acid, and the reaction was allowed to proceed for one hour at room temperature. After completion of the reaction, the reaction mixture was cooled for 30 minutes at temperatures ranging from 0 to 10° C., then resulting crystalline precipitate was collected by filtration to afford 2.3 g of the titled compound as colorless crystals, m.p.166–167° C.

¹H-NMR(CDCl$_3$); 4.09(t,2H), 6.11(s,1H), 6.52(br,1H), 7.12(t,1H), 7.30(s,4H), 7.70(s,2H).

Working Example 11
Production of 2-[4-(4-chloro-α-cyanobenzyl)-3,5-dichlorophenyl]-1,2,4-triazine-3,5(2H,4H)-dione In 20 ml of acetic acid was dissolved 2.0 g of 2-[4-(4-chloro-α-cyanobenzyl)-3,5-dichlorophenyl]-4,5-dihydro-1,2,4-triazin-3(2H)-one. To the solution was added three times as much mol. of 30% hydrogen peroxide. The reaction was allowed to proceed for 3 hours at 100° C. After completion of the reaction, the reaction mixture was poured into ice-water. Resulting crystalline precipitate was collected by filtration to afford 1.8 g of the titled compound as colorless crystals, m.p.290–292° C.

¹H-NMR(DMSO-d$_6$); 6.53(s,1H), 7.40(q,4H), 7.72(s, 1H), 7.85(s,2H), 12.50(s,1H).

Working Example 12
Synthesis of 2-[4-(4-chlorobenzyl)-3,5-dichlorophenyl]-1,2,4-triazine-3(2H)-oxo-5(4H)-thione In 50 ml of toluene was suspended 1.9 g of 2-[4-(4-chlorobenzyl)-3,5-dichlorophenyl]-1,2,4-triazine-3,5(2H,4H)-dione. To the suspension was added 1.2 g of 2,4-Bis(4-methoxyphenyl)-1,3-dithia-2,4-diphosphetane-2,4-disulfide and refluxed for one hour. After completion of the reaction, insolubles were removed and the solution was concentrated. After the concentrate was added diethylether, 1.8 g of the title compound was filtlated as crystals. m.p.173–175° C.

Working Example 13
Compounds produced by substantially the same manner as in Working Example 12 and their physical constants were set forth in Table 4.

TABLE 4

| No. | Compounds | m.p. (° C.) | ¹H-NMR [Solvent] δ |
|-----|-----------|-------------|---------------------|
| 1 | (structure) | 173~175 | [DMSO-d$_6$] 4.29(s, 2H) 7.25(q, 4H) 7.79(s, 2H) 7.89(s, 1H) 13.90(br, 1H) |

TABLE 4-continued

| No. | Compounds | m.p. (° C.) | ¹H-NMR [Solvent] δ |
|---|---|---|---|
| 2 | 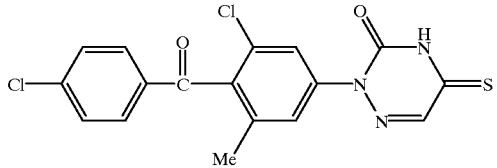 | 104~106 | [DMSO-d$_6$] 2.16(s, 3H) 7.60~7.89(s, 7H) 13.89(br, 1H) |
| 3 | 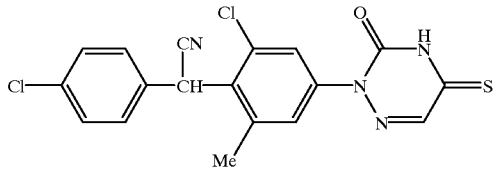 | 234~235 | [DMSO-d$_6$] 2.41(s, 3H) 6.36(s, 1H) 7.17~7.70(m, 6H) 7.87(s, 1H) 13.36(br, 1H) |
| 4 | 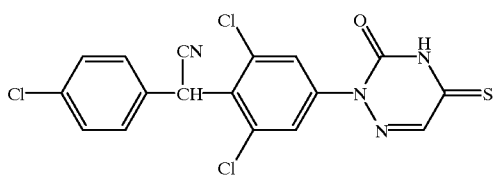 | 249~250 | [DMSO-d$_6$] 6.25(s, 1H) 7.41(q, 4H) 7.88(s, 1H) 7.90(s, 2H) 13.90(br, 1H) |

Working Example 14

Synthesis of 2-[4-(4-chlorobenzyl)-3,5-dichlorophenyl]-hexahydro-1,2,4-triazine-3,5(3H,4H)-dione In 100 ml of acetic acid was dissolved 2.3 g of 2-[4-(4-chlorobenzyl)-3,5-dichlorophenyl]-1,2,4-triazine-3,5(2H,4H)-dione and refluxed with 3.1 g zinc powder for 3 hours. After completion of the reaction, insolubles were removed, and the solution was concentrated. After concentrating was added 20 ml iced water, then the resulting crystalline precipitate was collected by filtration, which was washed with methanol, followed by drying to afford 2.1 g of the title compound as colorless crystals, m.p.267–268° C.

Working Example 15

Compounds produced by substantially the same manner as in Working Example 14 and their physical constants were set forth in Table 5.

TABLE 5

| No. | Compounds | m.p. (° C.) | ¹H-NMR [Solvent] δ |
|---|---|---|---|
| 1 | 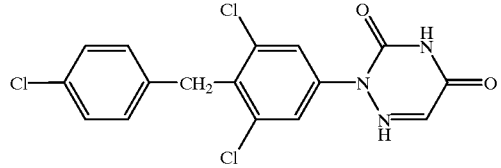 | 267~268 | [DMSO-d$_6$] 3.70(d, 2H) 4.20(s, 2H) 6.50(t, 1H) 7.23(q, 4H) 7.85(s, 1H) 10.80(s, 1H) |
| 2 | 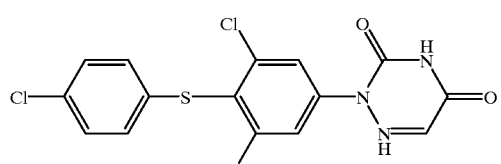 | 270~271 | [DMSO-d$_6$] 3.72(d, 1H) 6.52(t, 2H) 7.20(q, 4H) 8.03(s, 2H) 10.90(s, 1H) |
| 3 | 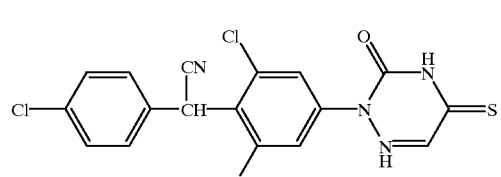 | 215~216 | [DMSO-d$_6$] 4.00(d, 2H) 6.42(s, 1H) 6.64(t, 1H) 7.35(q, 4H) 7.95(s, 2H) 12.50(s, 1H) |

TABLE 5-continued

| No. | Compounds | m.p. (° C.) | $^1$H-NMR [Solvent] δ |
|---|---|---|---|
| 4 | | 217~218 | [DMSO-d$_6$] 2.34(s, 3H) 3.99(d, 2H) 6.26(s, 1H) 6.62(s, 1H) 7.14~7.53 (m, 4H) 7.63(d, 1H) 7.77(d, 1H) 12.41(s, 1H) |
| 5 | | caramel | [CDCl$_3$] 2.26(s, 3H) 3.81(d, 2H) 4.87(t, 1H) 6.05(s, 1H) 7.14~7.39 (m, 4H) 7.59(d, 1H) 7.81(d, 1H) 8.34(s, 1H) |

Working Example 16
Synthesis of 2-{4-[4-(1-hydroxyethyl)benzyl]-3,5-dichlorophenyl}-4,5-dihydro-1,2,4-triazin-3(2H)-one In 1.5 ml of ethanol was suspended 0.15 g of 2-[4-(4-acetylbenzyl)-3,5-dichlorophenyl]-4,5-dihydra-1,2,4-triazin-3(2H)-one. To the suspension was added 0.1 g of sodium borohydride. The mixture was stirred for one hour at room temperature. The reaction mixture was poured into 10 ml ice-water, followed by extraction with 10 ml of ethylacetate. The extract was dried over anhydrous magnesium sulfate, and concentrated. This residue was purified by column chromatography (Merck Silica Gel 60; hexane-acetone=1:1) to provide 0.13 g of the title compound as colorless crystals, m.p.119–120° C.

$^1$H-NMR(CDCl$_3$); 1.52(d,3H), 2.58(br,1H), 4.12(m,2H), 4.29(s,2H), 4.81–4.96(m,1H), 5.29(br,1H), 7.05–7.33(m, 5H), 7.59(s,2H).

Working Example 17
Synthesis of 2-{4-[4-(1-hydroxypropyl)benzyl]-3,5-dichlorophenyl}-4,5-dihydro-1,2,4-triazin-3(2H)-one The title compound was synthesized in otherwise a similar manner as Example 16, m.p.148–149° C.

$^1$H-MMR(CDCl$_3$); 0.89(t,3H), 1.57–1.84(m,2H), 2.56(br, 1H), 4.11(m,2H), 4.29(s,2H), 4.54(m,1H), 5.56(br,1H), 7.05–7.20(n,5H), 7.59(s,2H).

Working Example 18
Synthesis of 2-[4-(4-chlorobenzyl)-3,5-dichlorophenyl]-1,2,4-triazine-3,5(2H,4H)-dione In 30 ml of tetrahydrofuran was dissolved 2.6 g of 2-[4-(4-chlorobenzyl)-3,5-dichlorophenyl]-4,5-dihydra-1,2,4-triazin-3(2H)-one. To the solution was added 4.5 g of pyridinium chlorochromate. The mixture was stirred at room temperature overnight, after which the insoluble matter was filtered off. The filtrate was concentrated. The residue was purified by column chromatography (Merck Silica Gel 60; chloroform-ethanol=20:1) to provide 2.2 g of the title compound as colorless crystals, m.p.175–176° C.

The production method of this second embodiment is to produce various 2-substituted-1,2,4-triazin-3-one derivatives, which are useful as, for example, herbicides and agents of controlling parasitic pest, conveniently and in a high yield. These useful compounds have come to be produced on an industrial scale, which makes a great contribution to the introduction of triazine derivatives, which are useful as, for example, medicine, veterinary drugs and agricultural chemicals, into market less expensively. Besides, the second embodiment contributes a great deal to the creation and development of useful and novel 2-substituted-1,2,4-triazin-3-one derivatives.

What is claimed is:

1. A compound or a salt thereof wherein said compound has a structure of the formula:

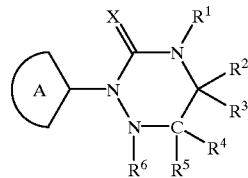

wherein ring A is an aromatic group which may be substituted with 1 to 5 substituents selected from the group consisting of (1) $C_{1-4}$ alkyl, (2) $C_{2-4}$ alkenyl, (3) $C_{2-4}$ alkynyl, (4) $C_{3-5}$ cycloalkyl, (5) $C_{5-7}$ cycloalkenyl, (6) $C_{7-11}$ aralkyl, (7) phenyl, (8) $C_{1-6}$ alkoxy, (9) phenoxy, (10) $C_{1-6}$ alkanoyl, (11) benzoyl, (12) $C_{1-6}$ alkanoyloxy, (13) carboxyl, (14) $C_{2-7}$ alkoxycarbonyl, (15) carbamoyl, (16) N-mono-$C_{1-6}$ alkylcarbamoyl, (17) N-di-$C_{1-4}$ alkylcarbamoyl, (18) cycloaminocarbonyl, (19) halogen, (20) mono-, di- or tri-halo-$C_{1-4}$ alkyl, (21) oxo, (22) amidino, (23) imino, (24) amino which may be protected with a group selected from (i) formyl, (ii) $C_{1-6}$ alkylcarbonyl which may be substituted with halogen atoms, (iii) $C_{6-10}$ aryl-carbonyl which may be substituted with 1 to 3 halogen atoms, $C_{1-6}$ alkylcarbonyl or nitro group, (iv) $C_{1-6}$ alkyloxycarbonyl which may be substituted with 1 to 3 halogen atoms, $C_{1-6}$ alkylcarbonyl or nitro group, (v) $C_{6-10}$ aryloxycarbonyl which may be substituted with 1 to 3 halogen atoms, $C_{1-6}$ alkylcarbonyl or nitro group, (vi) $C_{7-12}$ aralkyl-carbonyl which may be substituted with 1 to 3 halogen atoms, $C_{1-6}$ alkylcarbonyl or nitro group, (vii) trityl which may be substituted with 1 to 3 halogen atoms, $C_{1-6}$ alkylcarbonyl or nitro group and (viii) phthaloyl which may be substituted with 1 to 3 halogen atoms, $C_{1-6}$ alkylcarbonyl or nitro group, (25) mono-$C_{1-4}$ alkylamino, (26) di-$C_{1-4}$ alkylamino, (27) 3- to 6-membered cycloamino which may contain 1 to 3 hetero atoms selected from oxygen, sulfur and nitrogen, (28) $C_{1-6}$ alkanamido, (29) benzamido, (30) carbamoylamino, (31) N—$C_{1-4}$ alkylcarbamoylamino, (32) N,N-di-$C_{1-4}$ alkylcarbamoylamino, (33) $C_{1-3}$ alkylenedioxy,

(34) —B(OH)$_2$, (35) hydroxy, (36) epoxy, (37) nitro, (38) cyano, (39) mercapto, (40) sulfo, (41) sulfino, (42) phosphono, (43) dihydroxypolyol, (44) sulfamoyl, (45) mono-C$_{1-6}$ alkylsulfamoyl, (46) di-C$_{1-4}$ alkylsulfamoyl, (47) C$_{1-6}$ alkylthio, (48) phenylthio, (49) C$_{1-6}$ alkylsulfinyl, (50) phenylsulfinyl, (51) C$_{1-6}$ alkylsulfonyl, (52) phenylsulfonyl and (53) 5- or 6-membered heterocyclic group containing 1 to 4 hetero atoms selected from oxygen, sulfur and nitrogen, which may bound through one or two atomic chain containing oxygen, sulfur, nitrogen and carbon, in which any group having a carbon chain of 2 or more carbon atoms or a cyclic group may be further substituted with one or two substituents selected from the group consisting of (a) halogen, (b) hydroxy, (c) oxo, (d) C$_{1-4}$ alkoxy, (e) di-C$_{1-4}$ alkylamino, (f) halo-C$_{1-4}$ alkyl, (g) C$_{1-4}$ acyl, (h) hydroxy-C$_{1-4}$ alkyl, (i) C$_{1-4}$ alkoxy-C$_{1-4}$ alkyl, (j) cyano, (k) thioxo and (l) C$_{1-4}$ alkylthio, and in which when the substituent mentioned above exists on two ring-forming atoms adjacent to each other, they may bind together to form a ring:

X is oxygen or sulfur;

R$^1$ is hydrogen, C$_{1-7}$ acyl, C$_{1-7}$ alkyloxycarbonyl, C$_{1-4}$ alkyl, mono-, di- or trihalo-C$_{1-4}$ alkyl, or C$_{1-4}$ alkylcarbonyl;

R$^2$ and R$^3$ are independently selected from the group consisting of a hydrogen atom, a halogen atom, cyano, carboxy, carbamoyl, mercapto, hydroxy, C$_{1-4}$ alkyl, C$_{1-6}$ alkylthio, C$_{7-11}$ aralkylthio, C$_{2-4}$ alkenyl, C$_{2-4}$ alkynyl, C$_{1-6}$ alkoxy, C$_{3-6}$ cycloalkyl, C$_{6-10}$ aryl and a 5- to 7-membered heterocyclic group containing one to four hetero-atoms selected from group consisting of nitrogen, sulfur and oxygen, wherein the alkyl, alkylthio, aralkylthio, alkenyl, alkynyl, alkoxy, cycloalkyl, aryl or heterocyclic group may have one or two substituents selected from the group consisting of (a) halogen, (b) hydroxy, (c) oxo, (d) C$_{1-4}$ alkoxy, (e) di-C$_{1-4}$ alkylamino, (f) halo-C$_{1-4}$ alkyl, (g) C$_{1-4}$ acyl, (h) hydroxy-C$_{1-4}$ alkyl, (i) C$_{1-4}$ alkoxy-C$_{1-4}$ alkyl, (j) thioxo, (k) sulfide, (l) C$_{3-6}$ cycloalkyl and (m) mercapto, or when taken together, R$^2$ and R$^3$ represent =S;

R$^4$ and R$^5$ are independently selected from the group consisting of a hydrogen atom, a halogen atom, cyano, carboxy, carbamoyl, amino, nitro, hydroxy, mercapto, C$_{1-4}$ alkyl, C$_{2-4}$ alkenyl, C$_{2-4}$ alkynyl, C$_{3-6}$ cycloalkyl, C$_{6-10}$ aryl and a 5- to 7-membered heterocyclic group containing one to four hetero-atoms selected from the group consisting of nitrogen, sulfur and oxygen, wherein the alkyl, alkenyl, alkynyl, cycloalkyl, aryl or heterocyclic group may have one or two substituent groups selected from the group consisting of (a) halogen, (b) hydroxy, (c) oxo, (d) C$_{1-4}$ alkoxy, (e) di-C$_{1-4}$ alkylamino, (f) halo-C$_{1-4}$ alkyl, (g) C$_{1-4}$ acyl, (h) hydroxy-C$_{1-4}$ alkyl and (i) C$_{1-4}$ alkoxy-C$_{1-4}$ alkyl;

R$^6$ is selected from the group consisting of
  (1) a hydrogen atom,
  (2) a hydrocarbon residue selected from the group consisting of C$_{1-15}$ alkyl, C$_{3-8}$ cycloalkyl, C$_{2-10}$ alkenyl, C$_{2-10}$ alkynyl, C$_{3-10}$ cycloalkenyl, C$_{6-14}$ aryl and C$_{7-16}$ aralkyl, each of which may have one to five substituent groups selected from the group consisting of (1) nitro, (2) hydroxy, (3) oxo, (4) thioxo, (5) cyano, (6) carbamoyl, (7) carboxyl, (8) C$_{1-4}$ alkoxycarbonyl, (9) sulfo, (10) halogen, (11) C$_{1-4}$ alkoxy, (12) phenoxy, (13) halophenoxy, (14) C$_{1-4}$ alkylthio, (15) phenylthio, (16) C$_{1-4}$ alkylsulfinyl, (17) C$_{1-4}$ alkylsulfonyl, (18) amino, (19) C$_{1-6}$ acylamino, (20) mono- or di-C$_{1-4}$ alkylamino, (21) C$_{1-4}$ acyl, (22) benzoyl, (23) 5- or 6-membered heterocyclic group containing one to four heteroatoms selected from the group consisting of oxygen, sulfur and nitrogen, which may be substituted by one to four substituents selected from the group consisting of (a) halogen, (b) C$_{1-4}$ alkyl and (c) halophenoxy, and (24) C$_{1-10}$ haloalkyl, and where the hydrocarbon group is cycloalkyl, cycloalkenyl, aryl or aralkyl, each of which may have one to four C$_{1-4}$ alkyl group,
  (3) an acyl group selected from the group consisting of —COR$^a$, —CONHR$^a$, —CSR$^a$ and —CSNHR$^a$ wherein R$^a$ represents hydrogen or a hydrocarbon group selected from the group consisting of C$_{1-15}$ alkyl, C$_{3-8}$ cycloalkyl, C$_{2-10}$ alkenyl, C$_{2-10}$ alkynyl, C$_{3-10}$ cycloalkenyl, C$_{6-14}$ aryl and C$_{7-16}$ aralkyl, wherein each hydrocarbon group may be substituted with one or two substituent groups selected from the group consisting of (1) nitro, (2) hydroxy, (3) oxo, (4) thioxo, (5) cyano, (6) carbamoyl, (7) carboxyl, (8) C$_{1-4}$ alkoxycarbonyl, (9) sulfo, (10) halogen, (11) C$_{1-4}$ alkoxy, (12) phenoxy, (13) halophenoxy, (14) C$_{1-4}$ alkylthio, (15) phenylthio, (16) C$_{1-4}$ alkylsulfinyl, (17) C$_{1-4}$ alkylsulfonyl, (18) amino, (19) C$_{1-6}$ acylamino, (20) mono- or di-C$_{1-4}$ alkylamino, (21) C$_{1-4}$ acylt (22) benzoyl, and (23) 5- or 6-membered heterocyclic group containing one to four hetero-atoms selected from the group consisting of oxygen, sulfur and nitrogen, which may be substituted by one to four substituents selected from the group consisting of (a) halogen, (b) C$_{1-4}$ alkyl and (c) halophenoxy, and when the hydrocarbon group is cycloalkyl, cycloalkenyl, aryl or aralkyl, each may have one to four C$_{1-4}$ alkyl groups,
  (4) an oxycarbonyl group of the formula —COOR$^a$ wherein R$^a$ is as defined above, and
  (5) a 5- to 8-membered heterocyclic group or condensed heterocyclic group derived therefrom containing one to four hetero-atoms selected from the group consisting of oxygen sulfur and nitrogen, which may have one to five substituent groups selected from the group consisting of (1) C$_{1-4}$ alkyl, (2) C$_{2-4}$ alkeyl, (3) C$_{2-4}$ alkynyl, (4) C$_{3-6}$ cycloalkyl, (5) C$_{5-7}$ cycloalkenyl, (6) C$_{7-11}$ aralkyl, (7) phenyl, (8) C$_{1-6}$ alkoxy, (9) phenoxy, (10) C$_{1-6}$ alkanoyl, (11) benzoyl, (12) C$_{1-6}$ alkanoyloxy, (13) carboxyl, (14) C$_{2-7}$ alkoxycarbonyl, (15) carbamoyl (16) N-mono-C$_{1-4}$ alkylcarbamoyl, (17) N,N-di-C$_{1-4}$ alkylcarbamoyl, (18) cycloaminocarbonyl, (19) halogen, (20) mono-, di- or trihalo-C$_{1-4}$ alkyl, (21) oxo, (22) amidino, (23) imino, (24) amino, (25) mono-C$_{1-4}$ alkylamino, (26) di-C$_{1-4}$ alkylamino, (27) 3- to 6-membered cycloamino containing 1 to 3 hetero-atoms selected from oxygen, sulfur, and nitrogen, (28) C$_{1-6}$ alkanoylamido, (29) benzamido, (30) carbamoylamino, (31) N—C$_{1-4}$ alkylcarbamoylamino, (32) N,N-di-C$_{1-4}$ alkylcarbamoylamino, (33) C$_{1-3}$ alkylenedioxy, (34) —B(OH)$_2$, (35) hydroxy, (36) epoxy, (37) nitro, (38) cyano, (39) mercapto, (40) sulfo, (41) sulfino, (42) phosphono, (43) dihydroxypolyol, (44) sulfamoyl, (45) mono-C$_{1-6}$ alkylsulfamoyl (46) di-C$_{1-4}$ alkylsulfamoyl, (47) C$_{1-6}$ alkylthio (48) phenylthio, (49) C$_{1-6}$ alkylsulfinyl, (50) phenylsulfinyl, (51) C$_{1-6}$ alkylsulfonyl and (52) phenylsulfonyl, and wherein the hydrocarbon group, 5- to 8-membered heterocyclic group and condensed heterocyclic group may be bound through a hetero-atom selected from the group consisting of a nitrogen atom of an amino, $C_{1-4}$ alkylamino, hydroxyamino or hydrazino group, a sulfur atom of a thiocarbonyl or sulfino group and an oxygen atom, $R^1$ and $R^2$ or $R^5$ and $R^6$ when taken together can form a chemical bond;

provided that where ring A is a phenyl group having at least a halogen atom in position 2 or 4 and X is an oxygen atom, then $R^5$ and $R^6$ do not bind together to form a chemical bond.

2. A compound or a salt thereof as claimed in claim 1, wherein ring A is a phenyl group which may be substituted with 1 to 5 substituents selected from the group consisting of (1) $C_{1-4}$ alkyl, (2) $C_{2-4}$ alkenyl, (3) $C_{1-4}$ alkynyl, (4) $C_{3-6}$ cycloalkyl, (5) $C_{5-7}$ cycloalkenyl, (6) $C_{7-11}$ aralkyl, (7) phenyl, (8) $C_{1-6}$ alkoxy, (9) phenoxy, (10) $C_{1-6}$ alkanoyl, (11) benzoyl, (12) $C_{1-6}$ alkanoyloxy, (13) carboxyl, (14) $C_{2-7}$ alkoxycarbonyl, (15) carbamoyl, (16) N-mono-$C_{1-4}$ alkylcarbamoyl, (17) N-di-$C_{1-4}$ alkylcarbamoyl (18) cycloaminocarbonyl, (19) halogen, (20) mono-, di- or tri-halo-$C_{1-4}$ alkyl, (21) oxo, (22) amidino, (23) imino, (24) amino which may be protected with a group selected from (i) formyl, (ii) $C_{1-6}$ alkyl-carbonyl which may be substituted with halogen atoms, (iii) $C_{6-10}$ aryl-carbonyl which may be substituted with 1 to 3 halogen atoms, $C_{1-6}$ alkylcarbonyl or nitro group, (iv) $C_{1-6}$ alkyloxycarbonyl which may be substituted with 1 to 3 halogen atoms, $C_{1-6}$ alkyloxycarbonyl which may be substituted with 1 to 3 halogen atoms, $C_{1-6}$ alkylcarbonyl or nitro group, (v) $C_{6-10}$ aryloxycarbonyl which may be substituted with 1 to 3 haloaen atoms, $C_{1-6}$ alkylcarbonyl or nitro group, (vi) $C_{7-12}$ aralkylcarbonyl which may be substituted with 1 to 3 halogen atoms, $C_{1-6}$ alkylcarbonyl or nitro group, (vii) trityl which may be substituted with 1 to 3 halogen atoms, $C_{1-6}$ alkylcarbonyl or nitro group and (viii) phthaloyl which may be substituted with 1 to 3 halogen atoms, $C_{1-6}$ alkylcarbonyl or nitro group, (25) mon-$C_{1-4}$ alkylamino, (26) di-$C_{1-4}$ alkylamino, (27) 3- to 6-membered cycloamino which may contain 1 to 3 hetero atoms selected from oxygen, sulfur and nitrogen, (28) $C_{1-6}$ alkanamido, (29) benzamido, (30) carbamoylamino, (31) N—$C_{1-4}$ alkylcarbamoylamino, (32) N,N-di-$C_{1-4}$ alkylcarbamoylamino, (33) $C_{1-3}$ alkylenedioxy, (34) —$B(OH)_2$, (35) hydroxy, (36) epoxy, (37) nitro, (38) cyano, (39) mercapto, (40) sulfo, (41) sulfino, (42) phosphono, (43) dihydroxypolyol, (44) sulfamoyl, (45) mono-$C_{1-6}$ alkylsulfamoyl, (46) di-$C_{1-4}$ alkylsulfamoyl, (47) $C_{1-6}$ alkylthio, (48) phenylthio, (49) $C_{1-6}$ alkylsulfinyl, (50) phenylsulfinyl, (51) $C_{1-6}$ alkylsulfonyl, (52) phenylsulfonyl and (53) 5- or 6-membered heterocyclic group containing 1 to 4 hetero atoms selected from oxygen, sulfur and nitrogen, which may bound through one or two atomic chain containing oxygen, sulfur, nitrogen and carbon, in which any group having a carbon chain of 2 or more carbon atoms or a cyclic group may be further substituted with one or two substituents selected from the group consisting of (a) halogen, (b) hydroxy, (c) oxo, (d) $C_{1-4}$ alkoxy, (e) di-$C_{1-4}$ alkylamino, (f) halo-$C_{1-4}$ alkyl, (a) $C_{1-4}$ acyl, (h) hydroxy-$C_{1-4}$ alkyl, (i) $C_{1-4}$ alkoxy-$C_{1-4}$ alkyl, (j) cyano, (k) thioxo and (l) $C_{1-4}$ alkylthio, and in which when the substituent mentioned above exists on two ring-forming atoms adjacent to each other, they may bind together to form a ring.

3. A compound or a salt thereof as claimed in claim 1, wherein ring A is a 5- or 6-membered unsaturated heterocyclic group comprising 1 to 4 hetero-atoms selected from oxygen, sulfur or nitrogen, which may be substituted with 1 to 5 substituents selected from the group consisting of (1) $C_{1-4}$ alkyl, (2) $C_{2-4}$ alkenyl, (3) $C_{2-4}$ alkynyl, (4) $C_{3-6}$ cycloalkyl, (5) $C_{5-7}$ cycloalkenyl, (6) $C_{7-11}$ aralkyl, (7) phenyl, (8) $C_{1-6}$ alkoxy, (9) phenoxy, (10) $C_{1-6}$ alkanoyl, (11) benzoyl, (12) $C_{1-6}$ alkanoyloxy, (13) carboxyl, (14) $C_{2-7}$ alkoxycarbonyl, (15) carbamoyl, (16) N-mono-$C_{1-4}$ alkylcarbamoyl, (17) N-di-$C_{1-4}$ alkylcarbamoyl, (18) cycloaminocarbonyl, (19) halogen, (20) mono-, di- or tri-halo-$C_{1-4}$ alkyl, (21) oxo, (22) amidino, (23) imino, (24) amino which may be protected with a group selected from (i) formyl, (ii) $C_{1-6}$ alkyl-carbonyl which may be substituted with halogen atoms, (iii) $C_{6-10}$ aryl-carbonyl which may be substituted with 1 to 3 halogen atoms, $C_{1-6}$ alkylcarbonyl or nitro group, (iv) $C_{1-6}$ alkyloxycarbonyl which may be substituted with 1 to 3 halogen atoms, $C_{1-6}$ alkylcarbonyl or nitro group, (v) $C_{6-10}$ aryloxycarbonyl which may be substituted with 1 to 3 halogen atoms, $C_{1-6}$ alkylcarbonyl or nitro group, (vi) $C_{7-12}$ aralkyl-carbonyl which may be substituted with 1 to 3 halogen atoms $C_{1-6}$ alkylcarbonyl or nitro group, (vii) trityl which may be substituted with 1 to 3 halogen atoms, $C_{1-6}$ alkylcarbonyl or nitro group and (viii) phthaloyl which may be substituted with 1 to 3 halogen atoms, $C_{1-6}$ alkylcarbonyl or nitro group, (25) mono-$C_{1-4}$ alkylamino, (26) di-$C_{1-4}$ alkylamino, (27) 3- to 6-membered cycloamino which may contain 1 to 3 hetero atoms selected from oxygen, sulfur and nitrogen, (28) $C_{1-6}$ alkanamido, (29) benzamido, (30) carbamoylamino, (31) N—$C_{1-4}$ alkylcarbamoylamino, (32) N,N-di-$C_{1-4}$ alkylcarbamoylamino, (33) $C_{1-3}$ alkylenedioxy, (34) —$B(OH)_2$, (35) hydroxy, (36) epoxy, (37) nitro, (38) cyano, (39) mercapto, (40) sulfo, (41) sulfino, (42) phosphono, (43) dihydroxypolyol, (44) sulfamoyl, (45) mono-$C_{1-6}$ alkylsufamoyl, (46) di-$C_{1-4}$ alkylsulfamoyl, (47) $C_{1-6}$ alkylthio, (48) phenylthio, (49) $C_{1-6}$ alkylsulfinyl, (50) phenylsulfinyl, (51) $C_{1-6}$ alkylsulfonyl (52) phenylsulfonyl and (53) 5- or 6-membered heterocyclic group containing 1 to 4 hetero atoms selected from oxygen, sulfur and nitrogen, which may bound through one or two atomic chain containing oxygen, sulfur, nitrogen and carbon, in which any group having a carbon chain of 2 or more carbon atoms or a cyclic group may be further substituted with one or two substituents selected from the group consisting of (a) halogen, (b) hydroxy, (c) oxo, (d) $C_{1-4}$ alkoxy, (e) di-$C_{1-4}$ alkylamino, (f) halo-$C_{1-4}$ alkyl, (g) $C_{1-4}$ acyl, (h) hydroxy-$C_{1-4}$ alkyl, (i) $C_{1-4}$ alkoxy-$C_{1-4}$ alkyl, (j) cyano, (k) thioxo and (l) $C_{1-4}$ alkylthio, and in which when the substituent mentioned above exists on two-ring forming atoms adjacent to each other, they may bind together to form a ring.

4. A compound or a salt thereof as claimed in claim 3, wherein said 5- or 6-membered unsaturated heterocyclic group is a monocyclic 5- or 6-membered unsaturated heterocyclic group comprising 1 to 4 hetero-atoms selected from oxygen, sulfur or nitrogen.

5. A compound or a salt thereof as claimed in claim 3, wherein said 5- or 6-membered unsaturated heterocyclic group is a pyridyl group.

6. A compound or a salt thereof as claimed in claim 1, wherein $R^1$ is a hydrogen atom.

7. A compound or a salt thereof as claimed in claim 6, wherein $R^1$ is a $C_{1-4}$ alkyl group, or mono-, di- or trihalo-$C_{1-4}$ alkyl group.

8. A compound or a salt thereof as claimed in claim 7, wherein $R^1$ is a $C_{1-4}$ alkyl group.

9. A compound or a salt thereof as claimed in claim 1, wherein $R^2$ and $R^3$ are independently selected from the group consisting of a hydrogen atom, a halogen atom, a $C_{1-4}$ alkyl, a $C_{1-4}$ alkoxy, phenoxy, $C_{1-4}$ alkylthio or phenylthio group, wherein the alkyl, alkoxy or alkylthio may have one or two substituents selected from the group consisting of (a) halogen, (b) hydroxy, (c) oxo, (d) $C_{1-4}$ alkoxy, (e) di-$C_{1-4}$ alkylamino, (f) halo-$C_{1-4}$ alkyl, (g) $C_{1-4}$ acyl, (h) hydroxy-$C_{1-4}$ alkyl, (i) $C_{1-4}$ alkoxy-$C_{1-4}$ alkyl, (j) thioxo, (k) sulfide, (l) $C_{3-6}$ cycloalkyl and (m) mercapto, or when taken together, $R^2$ and $R^3$ represent =S.

10. A compound or a salt thereof as claimed in claim 9, wherein $R^2$ and $R^3$ are independently selected from the group consisting of a hydrogen atom or a $C_{1-4}$ alkyl which may have one or two substituents selected from the group consisting of (a) halogen, (b) hydroxy, (c) oxo, (d) $C_{1-4}$ alkoxy, (e) di-$C_{1-4}$ alkylamino, (f) halo-$C_{1-4}$ alkyl, (g) $C_{1-4}$ acyl, (h) hydroxy-$C_{1-4}$ alkyl, (i) $C_{1-4}$ alkoxy-$C_{1-4}$ alkyl, (j) thioxo, (k) sulfide, (l) $C_{3-6}$ cycloalkyl and (m) mercapto.

11. A compound or a salt thereof as claimed in claim 9, wherein $R^2$ and $R^3$ taken together represent =S.

12. A compound or a salt thereof as claimed in claim 1, wherein $R^4$ and $R^5$ are independently selected from the group consisting of a hydrogen atom, a halogen atom, $C_{1-4}$ alkyl or $C_{6-10}$ aryl group wherein the alkyl or aryl may have one or two substituent groups selected from the group consisting of (a) halogen, (b) hydroxy, (c) oxo, (d) $C_{1-4}$ alkoxy, (e) di-$C_{1-4}$ alkylamino, (f) halo-$C_{1-4}$ alkyl, (g) $C_{1-4}$ acyl, (h) hydroxy-$C_{1-4}$ alkyl and (i) $C_{1-4}$ alkoxy-$C_{1-4}$ alkyl.

13. A compound or a salt thereof as claimed in claim 12, wherein $R^4$ and $R^5$ are each a hydrogen atom, halogen atom or $C_{1-4}$ alkyl.

14. A compound or a salt thereof as claimed in claim 1, wherein $R^6$ is a hydrogen atom or a hydrocarbon residue selected from the group consisting of $C_{1-15}$ alkyl, $C_{6-14}$ aryl and $C_{7-16}$ aralkyl, each of which may have one to five substituent groups selected from the group consisting of (1) nitro, (2) hydroxy, (3) oxo, (4) thioxo, (5) cyano, (6) carbamoyl, (7) carboxyl, (8) $C_{1-4}$ alkoxycarbonyl, (9) sulfo, (10) halogen, (11) $C_{1-4}$ alkoxy, (12) phenoxy, (13) halophenoxy, (14) $C_{1-4}$ alkylthio, (15) phenylthio, (16) $C_{1-4}$ alkylsulfinyl, (17) $C_{1-4}$ alkylsulfonyl, (18) amino, (19) $C_{1-6}$ acylamino, (20) mono- or di-$C_{1-4}$ alkylamino, (21) $C_{1-4}$ acyl, (22) benzoyl, (23) 5- or 6-membered heterocyclic group containing one to four hetero-atoms selected from the group consisting of oxygen, sulfur and nitrogen, which may be substituted by one to four substituents selected from the group consisting of (a) halogen, (b) $C_{1-4}$ alkyl and (c) halophenoxy, and (24) $C_{1-10}$ haloalkyl, and where the hydrocarbon group is aryl or aralkyl, each of which may have one to four $C_{1-4}$ alkyl group.

15. A method for preparing a compound of the formula:

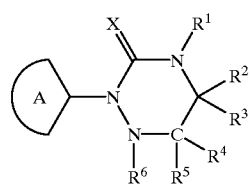

wherein A, X and $R^1$–$R^6$ are as defined in claim 1, said method comprises cyclizing the compound of the formula:

a) 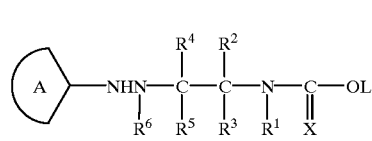

b) 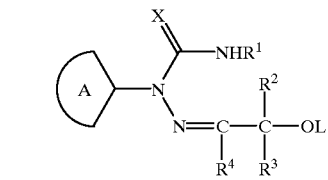

or c) 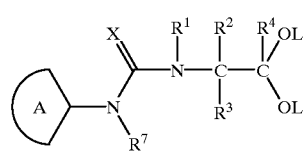

wherein $R^7$ is optionally protected amino group and L is an alkyl or acyl.

16. An antiprotozoal composition comprising an effective amount of a compound according to claim 1 or a pharmaceutically acceptable salt thereof and a pharmaceutically acceptable carrier, excipient or diluent.

17. The composition as claimed in claim 16, wherein said protozoa is coccidia.

18. An animal feed additive premix comprising a compound according to claim 1 or a physiologically acceptable salt thereof.

19. A method for inhibiting protozoa in an animal which comprises administering an effective amount of the compound according to claim 1 or a physiologically acceptable salt thereof to said animal.

20. The method as claimed in claim 19, wherein said animal is a bird.

21. A method for breeding an animal which comprises administering the compound according to claim 1 or a physiologically acceptable salt thereof to said animal.

* * * * *